United States Patent [19]

Magnusson et al.

[11] Patent Number: 4,868,289

[45] Date of Patent: Sep. 19, 1989

[54] GLYCOSIDIC DERIVATIVES

[75] Inventors: Hans G. Magnusson, Lund; Torbjörn Frejd, Södra Sandby, both of Sweden

[73] Assignee: Symbicom Aktiebolag, Umea, Sweden

[21] Appl. No.: 907,690

[22] PCT Filed: Jan. 13, 1986

[86] PCT No.: PCT/DK86/00006

§ 371 Date: Sep. 3, 1986

§ 102(e) Date: Sep. 3, 1986

[87] PCT Pub. No.: WO86/04065

PCT Pub. Date: Jul. 17, 1986

[30] Foreign Application Priority Data

Jan. 14, 1985 [DK] Denmark ................................ 176/85

[51] Int. Cl.$^4$ .................. C07H 15/04; C07H 15/18; A61K 31/70; A61K 31/705

[52] U.S. Cl. .................................. 536/4.1; 536/5; 536/17.2; 536/17.5; 536/17.6; 536/17.7; 536/17.8; 536/17.9; 536/18.2; 536/18.4

[58] Field of Search ...................... 536/4.1, 17.2, 17.5, 536/17.6, 17.7, 17.8, 17.9, 18.2, 18.4, 5; 514/25, 26

[56] References Cited

U.S. PATENT DOCUMENTS

| 2,252,706 | 8/1941 | Coles et al. | 536/18.4 |
| 3,843,626 | 10/1974 | Sutton | 536/17.5 X |
| 3,939,145 | 2/1976 | Gordon | 536/17.9 |
| 3,939,146 | 2/1976 | Gordon | 536/17.9 |
| 3,965,262 | 6/1976 | Gordon | 536/17.9 X |
| 4,016,261 | 4/1977 | Gordon | 536/18.7 X |
| 4,017,608 | 4/1977 | Gordon | 536/120 X |
| 4,056,322 | 11/1977 | Gordon et al. | 536/17.9 |
| 4,238,473 | 12/1980 | Lemieux et al. | 424/11 |
| 4,557,931 | 12/1985 | Irie et al. | 424/88 |
| 4,675,392 | 6/1987 | Dahmen et al. | 536/17.5 X |

OTHER PUBLICATIONS

Hood et al., *Immunology, Second Edition*, p. 6, (1984).
S. Hakomori, Ann. Rev. Bio. Chem., 50:733, (1981).
N. Sharon and H. Lis, Chem. Eng. News, 21, (Mar. 30, 1981).
R. U. Lemieux, Chem. Soc., Rev., 423, (1978).
N. Sharon and H. Lis, Science, 177:949, (1972).
E. H. Beachey, J. Infect. Diseases, 143:325, (1981).
J. S. Slama and R. R. Rando, Biochemistry, 19:4595, (1980).
E. A. Kabat, Methods Enz., 70:3, (1972).
J. Dahmen, T. Frejd, G. Magnusson, G. Noori, and A. S. Carlstrom, Carbohydr. Res., 127:27, (1984).
R. U. Lemieux, D. R. Bundle, and D. A. Baker, J. Am., Chem. Soc., 97:14, (1975).
J. Dahmen, T. Frejd, G. Magnusson, G. Norri, and A. S. Carlstrom, Carbohydr. Res., 129:63, (1984).
J. N. Isrealachvili, S. Marcelja, and R. G. Horn, Quarterly Reviews of Biophysics, 13:121, (1980).
J. Dahmen, T. Frejd, G. Gronberg, T. Lave, G. Magnusson, G. Noori, Carbohydr. Res., 116:303, (1983).
M. A. Nashad and L. Anderson, J. Am. Chem. Soc., 104:7282, (1982).

Primary Examiner—John W. Rollins
Assistant Examiner—W. Catchpole
Attorney, Agent, or Firm—Iver P. Cooper

[57] ABSTRACT

O-glycosidic compounds useful for therapy or prophylaxis of a wide variety of diseases, for diagnostic use or as research chemicals. Another object of the present invention is to provide a method for preparing the O-glycosidic compounds.

27 Claims, 2 Drawing Sheets

Fig. 1.

Binding of Sendai virus to synthetic glycolipids

- ● Galβ1→4Glcβ OCH$_2$CH(CH$_2$SO$_2$(CH$_2$)$_{15}$ CH$_3$)$_2$
- ▲ Glc "
- ○ Galβ1→4Glcβ OCH$_2$CH(CH$_2$S(CH$_2$)$_{15}$ CH$_3$)$_2$
- △ Glc "

$A_{492}$ = activity ng/well

Fig. 2.

Neo-glycoprotein-mediated inhibition of binding of Sendai virus to natural glycolipids ▲ Galactosyl-β-ceramide
o Globotetraosyl-β-ceramide $A_{492}$ = activity mg neo-glycoprotein

GLYCOSIDIC DERIVATIVES

BACKGROUND OF THE INVENTION

1. Field of the Invention

The present invention relates to novel glycosides and glycoconjugates useful as i.a. synthetic biological receptors.

2. Description of the Prior Art

Natural glycoconjugates consist of a carbohydrate portion, which is, in most cases, coupled to a lipid or a protein (cf. Hakomori (1981) and Sharon & Lis (1981)). In most of the glycolipids, the sugar is coupled to either the fatty amino alcohol sphingosine or to glycerol, which in turn are transformed into fatty acid derivatives. The general structures of these two types of glycolipids are shown below.

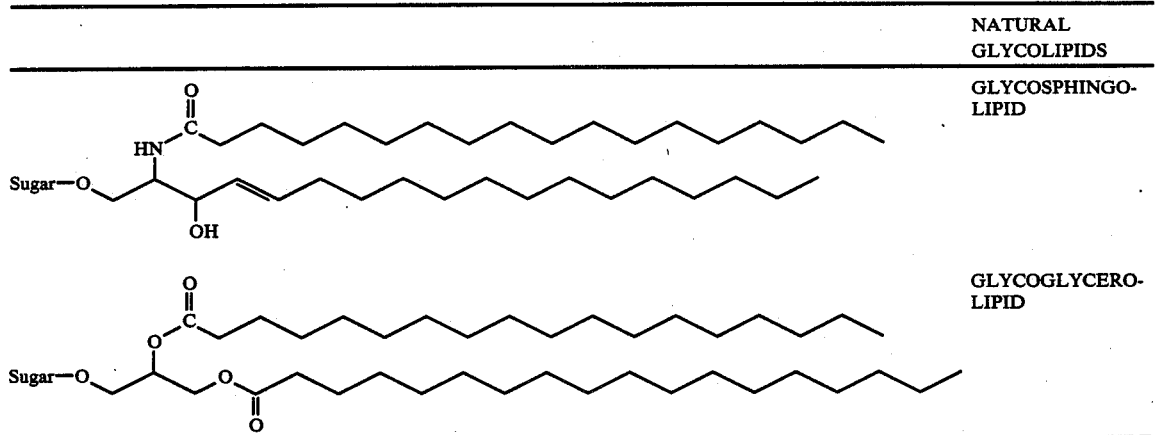

| | NATURAL GLYCOLIPIDS |
|---|---|
| (structure) | GLYCOSPHINGO-LIPID |
| (structure) | GLYCOGLYCERO-LIPID |

In the glycoproteins, the sugar moiety is coupled directly onto an amino acid in a protein. Glycolipids and glycoproteins are integral parts of the plasma membranes of mammalian cells. Some of these glycoconjugates function i.a. as specific receptors towards a variety of biological entities. The carbohydrate part of the glycoconjugate is exposed on the outside of the plasma membrane, and it may consequently exhibit antigenic properties. This is the basis for the various blood-group systems (cf. Lemieux (1978)). It has recently been shown that membrane-carbohydrates of the above type are important as receptors for proteins (cf. Sharon & Lis (1972) and Kabat (1980)) like lectins, antibodies and hormones and for anchoring microorganisms to cell surfaces (cf. Beachey (1981)).

Unnatural glycoconjugates (so-called neo-glycoconjugates) have been prepared both as neo-glycolipids (cf. Slama & Rando (1980) and Dahmen et al. (Carbohydr. Res., 127, 1984)) and neo-glycoproteins (cf. Lemieux et al. (1975) and Dahmen et al. (Carbohydr. Res., 129, 1984)). No neo-glycolipids having a close molecular similarity to the natural compound have, however, yet been prepared. It is known (cf. Israelachvili et al. (1980)) that the chemical structure of the hydrophobic part of lipids determines the type of aggregates that can be formed (micelles, liposomes, etc.) and also the kind of influence that a lipid will have when it is incorporated into e.g. a cellular membrane. In view of the high receptor specificity and biological importance of carbohydrate complexes it is obvious that there is a great need for molecularly well defined, easily prepared glycoconjugates for use in therapy, prophylaxis, and diagnosis as well as in biochemical research.

SUMMARY OF THE INVENTION

One object of the present invention is to provide novel O-glycosidic compounds useful for therapy or prophylaxis of a wide variety of diseases, for diagnostic use or as research chemicals.

Another object of the present invention is to provide a method for preparing the novel O-glycosidic compounds.

Thus, the invention relates to O-glycosidic compounds of the formula I

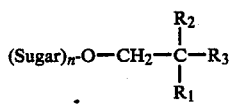

I wherein n is an integer from 1 to 10, inclusive, and Sugar is selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galactose, D-glucuronic acid, D-galacturonic acid, D-mannuronic acid, 2-deoxy-2-phthalimido-D-glucose, 2-deoxy-2-phthalimido-D-galactose and sialic acid, and derivatives thereof whereby, when $n>1$, the Sugar units may be the same or different; and $R_3$ is H and $R_1$ and $R_2$ which may be the same or different are
  a group $CH_2X$, wherein X is a leaving group,
  a group of the formula II

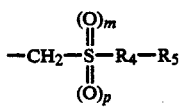

II wherein
  m and p independently are 0 or 1 and $m+p$ is 0, 1 or 2, $R_4$ is a saturated or unsaturated, branched or unbranched alkyl chain of 1–25 carbon atoms, aryl or a steroid group, and $R_5$ is H, CHO, $NO_2$, $NH_2$, OH, SH, COOH, $COOR_{10}$ wherein $R_{10}$ is $C_{1-4}$-alkyl or a carrier, $CONHNH_2$, $CON_3$, $CH(OR_{10})_2$ wherein $R_{10}$ is as defined above, or a carrier, a group of the formula III

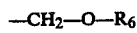
$$-CH_2-O-R_6 \quad\quad III$$

wherein
$R_6$ is H or the group $-R_4-R_5$, wherein $R_4$ and $R_5$ are as defined above,
or a group of the formula IIIa

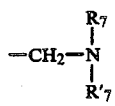
$$\begin{array}{c} R_7 \\ | \\ =CH_2-N \\ | \\ R'_7 \end{array} \quad\quad IIIa$$

wherein
$R_7$ and $R'_7$, which may be the same or different, are the same as $R_6$ defined above; or
$R_2$ and $R_3$ together form $=CH_2$, and
$R_1$ is
$CH_2X$, wherein X is as defined above,
a group of the formula II defined above, wherein $R_4$, $R_5$, m and p are as defined above,
a group of the formula III defined above, wherein $R_6$ is as defined above,
a group of the formula IIIa defined above, wherein $R_7$ and $R'_7$ are as defined above,
or a group of the formula IV

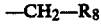
$$-CH_2-R_8 \quad\quad IV$$

wherein
$R_8$ is a carrier; as well as polymers formed from monomers of the formula I, the polymers having
(1) the formula XX

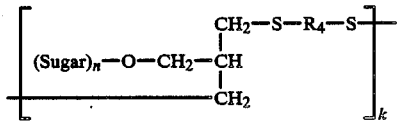
$$\left[ \begin{array}{c} (Sugar)_n-O-CH_2-CH \begin{array}{c} CH_2-S-R_4-S \\ | \\ CH_2 \end{array} \end{array} \right]_k \quad XX$$

wherein Sugar, n, and $R_4$ are as defined above, and k is an integer from 2 to 1000; or
(2) the formula XXI

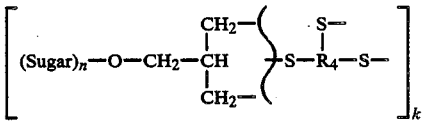
$$\left[ (Sugar)_n-O-CH_2-\begin{array}{c} CH_2-\\ | \\ CH \\ | \\ CH_2- \end{array} \begin{array}{c} S-\\ | \\ S-R_4-S- \end{array} \right]_k \quad XXI$$

wherein Sugar, n, k, and $R_4$ are as defined above.

In the formula I, the carbohydrate moiety "(Sugar)$_n$" is attached to the rest of the molecular through an α-or β-bond to the 1-carbon atom (the anomeric carbon) in one of the Sugar units. The carbohydrate unit, to which the rest of the molecule is bonded, is usually the terminal carbohydrate unit at the reducing end of an unbranched or branched chain of pentose or hexose units.

It will be seen that the monomers covered by Formula I include O-glycosidic compounds of the formula

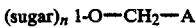
$$(sugar)_n\text{ }1\text{-}O-CH_2-A \quad\quad (Ix)$$

where A is $-C(CH_2)-B_x$ or

$$\begin{array}{c} B_x \\ | \\ -CH \\ | \\ B_y \end{array}$$

$B_x$ ($R_1$) and $B_y$ ($R_2$), which may be the same, or different, are groups of the formula II,

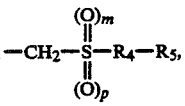
$$\begin{array}{c} (O)_m \\ \| \\ -CH_2-S-R_4-R_5, \\ \| \\ (O)_p \end{array} \quad\quad (II)$$

and where "sugar," n, m, p, $R_4$ and $R_5$ are as defined above.

The compounds set forth in Tables 2, 3, 4 and 5 below all fall within Ix as set forth above.

In the present context, the term "or derivatives thereof" with reference to the Sugar units designates that some or all of the free hydroxy groups in the carbohydrate moiety are derivatised or replaced by such groups as alkyl (such as methyl, ethyl or propyl), amino, fluoro or other groups. Such groups may in turn be substituted with various functional groups. The hydroxy groups in the sugar ring may be derivatised with acyl such as acetyl or benzyl, $C_{1-4}$ lower alkyl (in particular methyl or ethyl), or tetrahydropyranyl as well as a wide variety of other groups. Such derivative groups are capable of changing the properties (e.g. hydrophilicity, hydrophobicity, polarity, overall shape, etc.) of the carbohydrate moiety.

In the present context, the term "leaving group" designates any group that is easily split off when the carbon atom, to which it is attached, is subjected to a nucleophilic attack. Typical examples of leaving groups are halogens such as chlorine, bromine and iodine, in particular bromine, p-toluenesulfonyl, mesyl, as well as ester functions such as lower alkyl ester functions, e.g. methylcarbonyloxy, ethylcarbonyloxy, propylcarbonyloxy, etc., and aryl ester functions such as phenyl carbonyloxy, wherein the phenyl group may also carry substituents.

The term "carrier" for $R_5$ designates any organic or inorganic, polymeric or macromolecular structure to which the aglycon part of the O-glycosidic compound of the formula I is attached. Examples of such carriers are residues of proteins, polysaccharides, plastic polymers and inorganic materials. Residues of proteins are preferably bonded through nucleophilic groups in the proteins, e.g. such groups as amino, hydroxy and mercapto groups. The proteins themselves may be any of a wide variety of proteins, in particular biologically compatible proteins such as globulins, albumins such as bovine serum albumin, fibrins, polylysin, "key-hole" limpet hemocyanine (KLH), etc. The polysaccharides, to which the O-glycosidic compounds are attached, may be any of a wide variety of polysaccharides. The aglycon part of the compound of formula I may be bonded through hydroxy groups on ordinary polysaccharides such as cellulose, starch or glycogen, through amino groups on amino saccharides such as chitosan or aminated sepharose, and through mercapto groups of thio-modified polysaccharides. Examples of plastics to which the aglycon part of the compounds of the formula I may be attached are aminated latex, thiolated, aminated, or hydroxylated polystyrene, and polyvinyl alcohol. The plastics in question may be in the form of e.g. beads or film. Examples of inorganic material, to which the aglycon part of the compounds of the formula I may be attached are silicon oxide materials such as silica gel, zeolite, diatomaceous earth, or the surface of various glass or silicagel types such as thiolated or aminated glass, where the silica gel or the glass may be in the form of e.g. beads. Another example of an inorganic material is aluminium oxide.

Examples of saturated or unsaturated, branched or unbranched alkyl chains of 1-25 carbon atoms for $R_4$ are methylene, dimethylene, tetramethylene, octamethylene, hexadecanmethylene, octadecanmethylene and octadec-9-enylene, preferably unbranched saturated alkyl chains such as octamethylene, hexadecamethylene, and octadecamethylene when $R_5$ is H. Preferred groups $—R_4—R_5$, when $R_5$ is different from H. are $(CH_2)_2—COOR_{10}$ and $(CH_2)_{10}—COOR_{10}$, where $R_{10}$ is as defined above. Examples of the group $—R_4-R_5$, where $R_4$ is aryl, is a phenyl group carrying as substituent any of the groups $R_5$ defined above and in any of the available positions.

The term "steroid group" may designate any commonly occurring biological steroid group such as the types of steroids, which, themselves or the form of derivatives thereof, are incorporated into biological membranes. Examples of such steroid units are cholesterol and lanosterol.

Examples of $C_{1-4}$ alkyl are methyl, ethyl, propyl, i-propyl, n-butyl, i-butyl and tert.butyl.

The polymers of the formula XX form a linear polymer in that the carbohydrate moiety with the 4-carbon aglycon unit attached alternates with a dithio unit in the fashion of a copolymer.

The polymers of the formula XXI are composed in a similar manner in that the carbohydrate moiety with the 4-carbon aglycon unit attached alternates in a copolymer manner with a trithio unit. Since the 4-carbon aglycon unit has only two bonding sites whereas the trithio unit has three bonding sites, the resulting structure is a 3-dimensional network in which a bonding site of the 4-carbon aglycon unit is always bonded to the sulphur atom of a trithio unit, whereas the 4-carbon aglycon unit is never bonded to another 4-carbon unit, and a trithio unit is never bonded to another trithio unit. This complicated spatial relationship is indicated through the vertical wavy line in the formula XXI.

DETAILED DESCRIPTION OF THE INVENTION

With respect to the compounds of the formula I in which $R_3$ is H, those in which $R_1$ and $R_2$ are identical are attractive since they are simpler to prepare than those in which $R_1$ and $R_2$ are non-identical. However, compounds in which $R_1$ and $R_2$ are dissimilar have a greater potential for having a wider spectrum of functionalities combined in a single compound, thereby rendering such compounds able to function in additional ways, e.g. in biological system.

Among compounds in which $R_1$ and $R_2$ are identical, preferred compounds are those in which $R_1$ and $R_2$ are $CH_2X$, wherein X is halogen, alkylcarbonyloxy, arylcarbonyloxy, alkylsulfonyloxy or arylsulfonyloxy. The alkyl moieties are preferably $C_{1-4}$ alkyl, and the aryl moiety is preferably an optionally substituted phenyl group, in particular tolyl. A preferred halogen is Br.

Another preferred class of compounds in which $R_1$ and $R_2$ are identical are compounds in which $R_1$ and $R_2$ are a group of formula II, wherein m and p are as defined above, $R_4$ is an unbranched alkyl chain of 2-17 carbon atoms, and $R_5$ is $CH_3$, $COOCH_3$ or a carrier. Examples of unbranched alkyl chains of 2-17 carbon atoms are dimethylene, heptamethylene, decamethylene, pentadecamethylene, and heptadecamethylene. In a particularly preferred subclass of compounds, m+p is 0 or 2.

Among the compounds in which $R_1$ and $R_2$ are different, interesting compounds are those in which one of $R_1$ and $R_2$ contains a long-chain hydrocarbon moiety terminated by a hydrocarbon chain, optionally with a shorter chain length than the first substituent.

Among the compounds in which $R_2$ and $R_3$ together form $=CH_2$ a preferred class of compounds are those in which $R_1$ is $CH_2X$, wherein X is halogen, alkylcarbonyloxy, arylcarbonyloxy, alkylsulfonyloxy or arylsulfonylox. X is preferably Br.

Another preferred class of compounds in which $R_2$ and $R_3$ together form $=CH_2$ are those in which $R_1$ is a group of the formula II defined above, wherein $R_4$ is an unbranched alkyl chain of 2-17 carbon atoms, $R_5$ is $CH_3$, $COOCH_3$ or a carrier, and m+p is 0.

A further preferred subclass of compounds in which $R_2$ and $R_3$ together form $=CH_2$ are those in which $R_1$ is a group of the formula III defined above, wherein $R_6$ is a group $—R_4—R_5$, wherein $R_4$ is an unbranched alkyl chain of 2-17 carbon atoms, $R_5$ is $CH_3$, $COOCH_3$ or a carrier.

Yet another preferred class of compounds in which $R_2$ and $R_3$ together form $=CH_2$ are those in which $R_1$ is a group of a formula IIIa, wherein $R_7$ and $R'_7$ are identical and are unbranched alkyl chains of 8-18 carbon atoms, e.g. octyl, hexadecyl or octadecyl.

Examples of important carbohydrate moieties $(Sugar)_n$ are listed below. In the list the various saccharide units are written according to the commonly used short-hand within the field in which the bonding between each saccharide unit (given as an abbreviation) is specified with respect to between which carbon atom in either saccharide unit the bond exists, and whether the bond is in an α-or β-configuration. The designation "NAc" or "NPhth" means that the saccharide unit in question carries an acetylamino or a phthalimido group, respectively, in the 2-position. The symbol "A" means the corresponding acid. Thus, "GlcA" is glucuronic acid. The notation "3Me" means that the hydroxyl group normally present in the 3-position has been replaced by a methyl group. Analogously, "3CH$_2$OH" refers to a hydroxymethyl group. Although the saccharide units may be present in both furanosidic and pyranosidic forms, pyranosidic units are normally preferred.

Examples of the carbohydrate moieties are:

Gal
Glc
Man
Fuc
Xyl
Rib
Ara
GlcNAc
  GalNAc
  GlcA
GalA
ManA
GlcNPhth
GalNPhth

NeuNAc
Manα1→3Man
Manα1→2Man
Manα1→6Man
Manβ1→4GlcNAc
Galβ1→4GlcNAc
GlcNAcβ1→4Man
GlcNAcβ1→2Man
Galβ1→6GlcNAc
Fucα1→6GlcNAc
Manα1→6GlcNAc
Galβ1→2Man
Fucα1→3GlcNAc
Fucα1→2Gal
Fucα1→3Gal
Fucα1→6Gal
Galβ1→3GlcNAc
Galβ1→2Gal
Galβ1→6Gal
Galβ1→3Gal
GalNAcα1→3Gal
GlcNAcβ1→3Gal
Galβ1→4Glc
Galα1→4Gal
GalNAcβ1→3Gal
GalNAcα1→3GalNAc
GalNAcβ1→4Gal
Galβ1→3GalNAc
Galα1→3Gal
Glcα1→6Glcα1→4Glcα1→4Glc
Glcα1→4Glc
Glcβ1→4Glc
NeuNAcα2→3Gal
NeuNAcα2→6Gal
NeuNAcα2→3GalNAc
NeuNAcα2→6GlcNAc
NeuNAcα2→8NeuNAc
Glcβ1→4Glcβ1→4Glc
Glcα1→4Glcα1→4Glc
Manα1→3(Manα1→6)Man
Galβ1→3GalNAcβ1→4Galβ1-4Glc
GalNAcβ1→4Galβ1→3GalNAcβ1→4Galβ1→4Glc
GalNAcβ1→3Galα1→4Galβ1→4Glc
GalNAcβ1→3Galα1→3Galβ1→4Glc
Galβ1→4GlcNAcβ1→3Galβ1→4Glc
Galβ1→3GlcNAcβ1→3Galβ1→3Galβ1→4Glc
Galβ1→4GlcNAcβ1→3Galβ1→4GlcNAcβ1→3Galβ1→4Glc

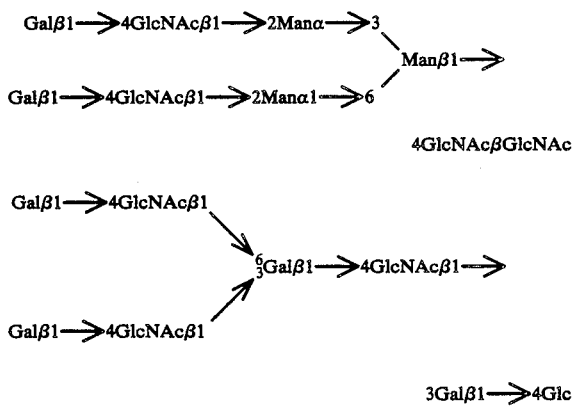

Galβ1→3Galβ1→4Glc

Galβ1→3Galβ1→3Galβ1→4Glc
GlcNAcβ1→3Gal
Galβ1→4Glc3Me
Galα1→4Gal3Me
Galβ1→4Glc3CH₂OH
Galα1→4Gal3CH₂OH
Galα1→4Galβ1→4Glc
Galα1→4Galβ1→4GlcNAc
Glcα1→6Glcα1→4Glc

Examples of important aglycon moieties are:
CH₂—CH—[CH₂S—(CH₂)₁₅—CH₃]₂
CH—CH—[CH₂S—(CH₂)₈—CH=CH—(CH₂)₇—CH₃]₂
CH₂—CH—[CH₂—S—(CH₂)₂—COOCH₃]₂
CH₂—CH—[CH₂—S—(CH₂)₁₀—COOCH₃]₂
CH₂—CH—[CH₂—S—(CH₂)₆—NH₂]₂
CH₂—CH—[CH₂—SO—(CH₂)₁₅—CH₃]₂
CH₂—CH—[CH₂—SO—(CH₂)₈—CH=CH—(CH₂)₇—CH₃]₂
CH₂—CH—[CH₂—SO—(CH₂)₂—COOCH₃]₂
CH₂—CH—[CH₂—SO—(CH₂)₁₀—COOCH₃]₂
CH₂—CH—[CH₂—SO—(CH₂)₆—NH₂]₂
—CH₂—CH(CH₂—SO₂—(CH₂)₁₅—CH₃)₂
—CH₂—CH(CH₂—SO₂—(CH₂)₈—CH=CH—(CH₂)₇—CH₃)₂
—CH₂—CH(CH₂—SO₂—(CH₂)₂—COOCH₃)₂
—CH₂—CH(CH₂(SO₂—(CH₂)₁₀—COOCH₃)₂
—CH₂—CH(CH₂—SO₂—(CH₂)₆—NH₂)₂
—CH₂C(=CH₂)—CH₂—S—(CH₂)₁₅—CH₃
—CH₂—C(=CH₂)—CH₂—S—(CH₂)₂—COOCH₃
—CH₂—C(=CH₂)—CH₂—S—(CH₂)₁₀—COOCH₃
—CH₂—C(=CH₂)—CH₂—S—(CH₂)₆—NH₂
—CH₂—C(=CH₂)—CH₂—N—((CH₂)₁₅—CH₃)₂
—CH₂—C(=CH₂)—CH₂—O—Cholesteryl
CH₂—CH—[CH₂—S—(CH₂)₁₀—COOCH₃]CH₂—S—(CH₂)₇CH₃
CH₂—CH—[CH₂—SO₂—(CH₂)₁₀—COOCH₃]CH₂—S—(CH₂)₇—CH₃
CH₂—CH—[CH₂—SO₂—(CH₂)₁₀—COOCH₃]CH₂—SO₂—(CH₂)₇—CH₃
—CH₂—CH(CH₂—SO₂—CH₂—CH₃)₂
—CH₂—CH(CH₂—SO₂—(CH₂)₂—COOH)₂

It is to be understood, that each and every one of the above-mentioned carbohydrate moieties may be combined with each and every one of the above-mentioned aglycon moieties, and that the listing should be understood as a practical way of representing each and every one of the resulting glycosidic compounds.

Examples of preferred glycosidic compounds of the formula I are:
GalO—CH₂—CH(CH₂—S—(CH₂)₁₅—CH₃)₂
GalO—CH₂—CH(CH₂—SO₂—(CH₂)₁₅—CH₃)₂
GalO—CH₂—CH(CH₂—SO₂—(CH₂)₁₀—COOCH₃)—CH₂—SO₂—(CH₂)₇—CH₃
GalO—CH₂—CH(CH₂—SO₂—CH₂—CH₃)₂
GalO—CH₂—C(=CH₂)—CH₂—S—(CH₂)₂—COOCH₃
GalO—CH₂—C(=CH₂)—CH₂—S—(CH₂)₁₀—COOCH₃
GlcO—CH₂—CH(CH₂—S—(CH₂)₁₅—CH₃)₂
GlcO—CH₂—CH(CH₂—SO₂—(CH₂)₁₅—CH₃)₂
GlcO—CH₂—CH(CH₂—SO₂—(CH₂)₁₀—COOCH₃)—CH₂—SO₂—(CH₂)₇—CH₃

GlcO—CH$_2$—CH(CH$_2$—SO$_2$—CH$_2$—CH$_3$)$_2$
GlcO—CH$_2$—C(=CH$_2$)—CH$_2$—S—(CH$_2$)$_2$—COOCH$_3$
GlcO—CH$_2$—C(=CH$_2$)—CH$_2$—S—(CH$_2$)$_{10}$—COOCH$_3$
ManO—CH$_2$—CH(CH$_2$—S—(CH$_2$)$_{15}$—CH$_3$)$_2$
ManO—CH$_2$—CH(CH$_2$—SO$_2$—(CH$_2$)$_{15}$—CH$_3$)$_2$
ManO—CH$_2$—CH(CH$_2$—SO$_2$—(CH$_2$)$_{10}$—COOCH$_3$)—CH$_2$—SO$_2$—(CH$_2$)$_7$—CH$_3$
ManO—CH$_2$—CH(CH$_2$—SO$_2$—CH$_2$—CH$_3$)$_2$
ManO—CH$_2$—C(=CH$_2$)—CH$_2$—S—(CH$_2$)$_2$—COOCH$_3$
ManO—CH$_2$—C(=CH$_2$)—CH$_2$—S—(CH$_2$)$_{10}$—COOCH$_3$
FucO—CH$_2$—CH(CH$_2$—S—(CH$_2$)$_{15}$—CH$_3$)$_2$
FucO—CH$_2$—CH(CH$_2$—SO$_2$—(CH$_2$)$_{15}$—CH$_3$)$_2$
FucO—CH$_2$—CH(CH$_2$—SO$_2$—(CH$_2$)$_{10}$—COOCH$_3$)—CH$_2$—SO$_2$—(CH$_2$)$_7$—CH$_3$
FucO—CH$_2$—CH(CH$_2$—SO$_2$—CH$_2$—CH$_3$)$_2$
FucO—CH$_2$—C(=CH$_2$)—CH$_2$—S—(CH$_2$)$_2$—COOCH$_3$
FucO—CH$_2$—C(=CH$_2$)—CH$_2$—S—(CH$_2$)$_{10}$—COOCH$_3$
XylO—CH$_2$—CH(CH$_2$—S—(CH$_2$)$_{15}$—CH$_3$)$_2$
XylO—CH$_2$—CH(CH$_2$—SO$_2$—(CH$_2$)$_{15}$—CH$_3$)$_2$
XylO—CH$_2$—CH(CH$_2$—SO$_2$—(CH$_2$)$_{10}$—COOCH$_3$)—CH$_2$—SO$_2$—(CH$_2$)$_7$—CH$_3$
XylO—CH$_2$—CH(CH$_2$—SO$_2$—CH$_2$—CH$_3$)$_2$
XylO—CH$_2$—C(=CH$_2$)—CH$_2$—S—(CH$_2$)$_2$—COOCH$_3$
XylO—CH$_2$—C(=CH$_2$)—CH$_2$—S—(CH$_2$)$_{10}$—COOCH$_3$
RibO—CH$_2$—CH(CH$_2$—S—(CH$_2$)$_{15}$—CH$_3$)$_2$
RibO—CH$_2$—CH(CH$_2$—SO$_2$—(CH$_2$)$_{15}$—CH$_3$)$_2$
RibO—CH$_2$—CH(CH$_2$—SO$_2$—(CH$_2$)$_{10}$—COOCH$_3$)—CH$_2$—SO$_2$—(CH$_2$)$_7$—CH$_3$
RibO—CH$_2$—CH(CH$_2$—SO$_2$—CH$_2$—CH$_3$)$_2$
RibO—CH$_2$—C(=CH$_2$)—CH$_2$—S—(CH$_2$)$_2$—COOCH$_3$
RibO—CH$_2$—C(=CH$_2$)—CH$_2$—S—(CH$_2$)$_{10}$—COOCH$_3$
AraO—CH$_2$—CH(CH$_2$—S—(CH$_2$)$_{15}$—CH$_3$)$_2$
AraO—CH$_2$—CH(CH$_2$—SO$_2$—(CH$_2$)$_{15}$—CH$_3$)$_2$
AraO—CH$_2$—CH(CH$_2$—SO$_2$—(CH$_2$)$_{10}$—COOCH$_3$)—CH$_2$—SO$_2$—(CH$_2$)$_7$—CH$_3$
AraO—CH$_2$—CH(CH$_2$—SO$_2$—CH$_2$—CH$_3$)$_2$
AraO—CH$_2$—C(=CH$_2$)—CH$_2$—S—(CH$_2$)$_2$—COOCH$_3$
AraO—CH$_2$—C(=CH$_2$)—CH$_2$—S—(CH$_2$)$_{10}$—COOCH$_3$
GlcNAcO—CH$_2$—CH(CH$_2$—S—(CH$_2$)$_{15}$—CH$_3$)$_2$
GlcNAcO—CH$_2$—CH(CH$_2$—SO$_2$—(CH$_2$)$_{15}$—CH$_3$)$_2$
GlcNAcO—CH$_2$—CH(CH$_2$—SO$_2$—(CH$_2$)$_{10}$—COOCH$_3$)—CH$_2$—SO$_2$—(CH$_2$)$_7$—CH$_3$
GlcNAcO—CH$_2$—CH(CH$_2$—SO$_2$—CH$_2$—CH$_3$)$_2$
GlcNAcO—CH$_2$—C(=CH$_2$)—CH$_2$—S—(CH$_2$)$_2$—COOCH$_3$
GlcNAcO—CH$_2$—C(=CH$_2$)—CH$_2$—S—(CH$_2$)$_{10$}—COOCH$_3$
GalNAcO—CH$_2$—CH(CH$_2$—S—(CH$_2$)$_{15}$—CH$_3$)$_2$
GalNAcO—CH$_2$—CH(CH$_2$—SO$_2$—(CH$_2$)$_{15}$—CH$_3$)$_2$
GalNAcO—CH$_2$—CH(CH$_2$—SO$_2$—(CH$_2$)$_{10}$—COOCH$_3$)—CH$_2$—SO$_2$—(CH$_2$)$_7$—CH$_3$
GalNAcO—CH$_2$—CH(CH$_2$—SO$_2$—CH$_2$—CH$_3$)$_2$
GalNAcO—CH$_2$—C(=CH$_2$)—CH$_2$—S—(CH$_2$)$_2$—COOCH$_3$
GalNAcO—CH$_2$—C(=CH$_2$)—CH$_2$—S—(CH$_2$)$_{10}$—COOCH$_3$
GlcAO—CH$_2$—CH(CH$_2$—S—(CH$_2$)$_{15}$—CH$_3$)$_2$
GlcAO—CH$_2$—CH(CH$_2$—SO$_2$—(CH$_2$)$_{15}$—CH$_3$)$_2$
GlcAO—CH$_2$—CH(CH$_2$—SO$_2$—(CH$_2$)$_{10}$—COOCH$_3$)—CH$_2$—SO$_2$—(CH$_2$)$_7$—CH$_3$
GlcAO—CH$_2$—CH(CH$_2$—SO$_2$—CH$_2$—CH$_3$)$_2$
GlcAO—CH$_2$—C(=CH$_2$)—CH$_2$—S—(CH$_2$)$_2$—COOCH$_3$
GlcAO—CH$_2$—C(=CH$_2$)—CH$_2$—S—(CH$_2$)$_{10}$—COOCH$_3$
GalAO—CH$_2$—CH(CH$_2$—S—(CH$_2$)$_{15}$—CH$_3$)$_2$
GalAO—CH$_2$—CH(CH$_2$—SO$_2$—(CH$_2$)$_{15}$—CH$_3$)$_2$
GalAO—CH$_2$—CH(CH$_2$—SO$_2$—(CH$_2$)$_{10}$—COOCH$_3$)—CH$_2$—SO$_2$—(CH$_2$)$_7$—CH$_3$
GalAO—CH$_2$—CH(CH$_2$—SO$_2$—CH$_2$—CH$_3$)$_2$
GalAO—CH$_2$—C(=CH$_2$)—CH$_2$—S—(CH$_2$)$_2$—COOCH$_3$
GalAO—CH$_2$—C(=CH$_2$)—CH$_2$—S—(CH$_2$)$_{10}$—COOCH$_3$
ManAO—CH$_2$—CH(CH$_2$—S—(CH$_2$)$_{15}$—CH$_3$)$_2$
ManAO—CH$_2$—CH(CH$_2$—SO$_2$—(CH$_2$)$_{15}$—CH$_3$)$_2$
ManAO—CH$_2$—CH(CH$_2$—SO$_2$—(CH$_2$)$_{10}$—COOCH$_3$)—CH$_2$—SO$_2$—(CH$_2$)$_7$—CH$_3$
ManAO—CH$_2$—CH(CH$_2$—SO$_2$—CH$_2$—CH$_3$)$_2$
ManAO—CH$_2$—C(=CH$_2$)—CH$_2$—S—(CH$_2$)$_2$—COOCH$_3$
ManAO—CH$_2$—C(=CH$_2$)—CH$_2$—S—(CH$_2$)$_{10}$—COOCH$_3$
GlcNPhthO—CH$_2$—CH(CH$_2$—S—(CH$_2$)$_{15}$—CH$_3$)$_2$
GlcNPhthO—CH$_2$—CH(CH$_2$—SO$_2$—(CH$_2$)$_{15}$—CH$_3$)$_2$
GlcNPhthO—CH$_2$—CH(CH$_2$—SO$_2$—(CH$_2$)$_{10}$—COOCH$_3$)—CH$_2$—SO$_2$—(CH$_2$)$_7$—CH$_3$
GlcNPhthO—CH$_2$—CH(CH$_2$—SO$_2$—CH$_2$—CH$_3$)$_2$
GlcNPhthO—CH$_2$—C(=CH$_2$)—CH$_2$—S—(CH$_2$)$_2$—COOCH$_3$
GlcNPhthO—CH$_2$—C(=CH$_2$)—CH$_2$—S—(CH$_2$)$_{10}$—COOCH$_3$
GalNPhthO—CH$_2$—CH(CH$_2$—S—(CH$_2$)$_{15}$—CH$_3$)$_2$
GalNPhthO—CH$_2$—CH(CH$_2$—SO$_2$—(CH$_2$)$_{15}$—CH$_3$)$_2$
GalNPhthO—CH$_2$—CH(CH$_2$—SO$_2$—(CH$_2$)$_{10}$—COOCH$_3$)—CH$_2$—SO$_2$—(CH$_2$)$_7$—CH$_3$
GalNPhthO—CH$_2$—CH(CH$_2$—SO$_2$—CH$_2$—CH$_3$)$_2$
GalNPhthO—CH$_2$—C(=CH$_2$)—CH$_2$—S—(CH$_2$)$_2$—COOCH$_3$
GalNPhthO—CH$_2$—C(=CH$_2$)—CH$_2$—S—(CH$_2$)$_{10}$—COOCH$_3$
NeuNAcO—CH$_2$—CH(CH$_2$—S—(CH$_2$)$_{15}$—CH$_3$)$_2$
NeuNAcO—CH$_2$—CH(CH$_2$—SO$_2$—(CH$_2$)$_{15}$—CH$_3$)$_2$
NeuNAcO—CH$_2$—CH(CH$_2$—SO$_2$—(CH$_2$)$_{10}$—COOCH$_3$)—CH$_2$—SO$_2$—(CH$_2$)$_7$—CH$_3$
NeuNAcO—CH$_2$—CH(CH$_2$—SO$_2$—CH$_2$—CH$_3$)$_2$
NeuNAcO—CH$_2$—C(=CH$_2$)—CH$_2$—S—(CH$_2$)$_2$—COOCH$_3$
NeuNAcO—CH$_2$—C(=CH$_2$)—CH$_2$—S—(CH$_2$)$_{10}$—COOCH$_3$
Manα1→3ManO—CH$_2$—CH(CH$_2$—S—(CH$_2$)$_{15}$—CH$_3$)$_2$ Manα1→3ManO—CH₂—CH(CH₂—SO₂—(CH₂)₁₅—CH₃)₂
Manα1→3ManO—CH₂—CH(CH₂—SO₂—(CH₂)₁₀—COOCH₃)—CH₂—SO₂—(CH₂)₇—CH₃
Manα1→3ManO—CH₂—CH(CH₂—SO₂—CH₂—CH₃)₂
Manα1→3ManO—CH₂—C(=CH₂)—CH₂—S—(CH₂)₂—COOCH₃
Manα1→3ManO—CH₂—C(=CH₂)—CH₂—S—(CH₂)₁₀—COOCH₃
Manα1→2ManO—CH₂—CH(CH₂—S—(CH₂)₁₅—CH₃)₂
Manα1→2ManO—CH₂—CH(CH₂—SO₂—(CH₂)₁₅—CH₃)₂
Manα1→2ManO—CH₂—CH(CH₂—SO₂—(CH₂)₁₀—COOCH₃)—CH₂—SO₂—(CH₂)₇—CH₃
Manα1→2ManO—CH₂—CH(CH₂—SO₂—CH₂—CH₃)₂
Manα1→2ManO—CH₂—C(=CH₂)—CH₂—S—(CH₂)₂—COOCH₃
Manα1→2ManO—CH₂—C(=CH₂)—CH₂—S—(CH₂)₁₀—COOCH₃
Manα1→6ManO—CH₂—CH(CH₂—S—(CH₂)₁₅—CH₃)₂
Manα1→6ManO—CH₂—CH(CH₂—SO₂—(CH₂)₁₅—CH₃)₂
Manα1→6ManO—CH₂—CH(CH₂—SO₂—(CH₂)₁₀—COOCH₃)—CH₂—SO₂—(CH₂)₇—CH₃
Manα1→6ManO—CH₂—CH(CH₂—SO₂—CH₂—CH₃)₂
Manα1→6ManO—CH₂—C(=CH₂)—CH₂—S—(CH₂)₂—COOCH₃
Manα1→6ManO—CH₂—C(=CH₂)—CH₂—S—(CH₂)₁₀—COOCH₃
Manβ1→4GlcNAcO—CH₂—CH(CH₂—S—(CH₂)₁₅—CH₃)₂
Manβ1→4GlcNAcO—CH₂—CH(CH₂—SO₂—(CH₂)₁₅—CH₃)₂
Manβ1→4GlcNAcO—CH₂—CH(CH₂—SO₂—(CH₂)₁₀—COOCH₃)—CH₂—SO₂—(CH₂)₇—CH₃
Manβ1→4GlcNAcO—CH₂—CH(CH₂—SO₂—CH₂—CH₃)₂
Manβ1→4GlcNAcO—CH₂—C(=CH₂)—CH₂—S—(CH₂)₂—COOCH₃
Manβ1→4GlcNAcO—CH₂—C(=CH₂)—CH₂—S—(CH₂)₁₀—COOCH₃
Galβ1→4GlcNAcO—CH₂—CH(CH₂—S—(CH₂)₁₅—CH₃)₂
Galβ1→4GlcNAcO—CH₂—CH(CH₂—SO₂—(CH₂)₁₅—CH₃)₂
Galβ1→4GlcNAcO—CH₂—CH(CH₂—SO₂—(CH₂)₁₀—COOCH₃)—CH₂—SO₂—(CH₂)₇—CH₃
Galβ1→4GlcNAcO—CH₂—CH(CH₂—SO₂—CH₂—CH₃)₂
Galβ1→4GlcNAcO—CH₂—C(=CH₂)—CH₂—S—(CH₂)₂—COOCH₃
Galβ1→4GlcNAcO—CH₂—C(=CH₂)—CH₂—S—(CH₂)₁₀—COOCH₃
GlcNAcβ1→4ManO—CH₂—CH(CH₂—S—(CH₂)₁₅—CH₃)₂
GlcNAcβ1→4ManO—CH₂—CH(CH₂—SO₂—(CH₂)₁₅—CH₃)₂
GlcNAcβ1→4ManO—CH₂—CH(CH₂—SO₂—(CH₂)₁₀—COOCH₃)—CH₂—SO₂—(CH₂)₇—CH₃
GlcNAcβ1→4ManO—CH₂—CH(CH₂—SO₂—CH₂—CH₃)₂
GlcNAcβ1→4ManO—CH₂—C(=CH₂)—CH₂—S—(CH₂)₂—COOCH₃
GlcNAcβ1→4ManO—CH₂—C(=CH₂)—CH₂—S—(CH₂)₁₀—COOCH₃
GlcNAcβ1→2ManO—CH₂—CH(CH₂—S—(CH₂)₁₅—CH₃)₂
GlcNAcβ1→2ManO—CH₂—CH(CH₂—SO₂—(CH₂)₁₅—CH₃)₂
GlcNAcβ1→2ManO—CH₂—CH(CH₂—SO₂—(CH₂)₁₀—COOCH₃)—CH₂—SO₂—(CH₂)₇—CH₃
GlcNAcβ1→2ManO—CH₂—CH(CH₂—SO₂—CH₂—CH₃)₂
GlcNAcβ1→2ManO—CH₂—C(=CH₂)—CH₂—S—(CH₂)₂—COOCH₃
GlcNAcβ1→2ManO—CH₂—C(=CH₂)—CH₂—S—(CH₂)₁₀—COOCH₃
Galβ1→6GlcNAcO—CH₂—CH(CH₂—S—(CH₂)₁₅—CH₃)₂
Galβ1→6GlcNAcO—CH₂—CH(CH₂—SO₂—(CH₂)₁₅—CH₃)₂
Galβ1→6GlcNAcO—CH₂—CH(CH₂—SO₂—(CH₂)₁₀—COOCH₃)—CH₂—SO₂—(CH₂)₇—CH₃
Galβ1→6GlcNAcO—CH₂—CH(CH₂—SO₂—CH₂—CH₃)₂
Galβ1→6GlcNAcO—CH₂—C(=CH₂)—CH₂—S—(CH₂)₂—COOCH₃
Galβ1→6GlcNAcO—CH₂—C(=CH₂)—CH₂—S—(CH₂)₁₀—COOCH₃
Fucα1→6GlcNAcO—CH₂—CH(CH₂—S—(CH₂)₁₅—CH₃)₂
Fucα1→6GlcNAcO—CH₂—CH(CH₂—SO₂—(CH₂)₁₅—CH₃)₂
Fucα1→6GlcNAcO—CH₂—CH(CH₂—SO₂—(CH₂)₁₀—COOCH₃)—CH₂—SO₂—(CH₂)₇—CH₃
Fucα1→6GlcNAcO—CH₂—CH(CH₂—SO₂—CH₂—C₃)₂
Fucα1→6GlcNAcO—CH₂—C(=CH₂)—CH₂—S—(CH₂)₂—COOCH₃
Fucα1→6GlcNAcO—CH₂—C(=CH₂)—CH₂—S—(CH₂)₁₀—COOCH₃
Manα1→6GlcNAcO—CH₂—CH(CH₂—S—(CH₂)₁₅—CH₃)₂
Manα1→6GlcNAcO—CH₂—CH(CH₂—SO₂—(CH₂)₁₅—CH₃)₂
Manα1→6GlcNAcO—CH₂—CH(CH₂—SO₂—(CH₂)₁₀—COOCH₃)—CH₂—SO₂—(CH₂)₇—CH₃
Manα1→6GlcNAcO—CH₂—CH(CH₂—SO₂—CH₂—CH₃)₂
Manα1→6GlcNAcO—CH₂—C(=CH₂)—CH₂—S—(CH₂)₂—COOCH₃
Manα1→6GlcNAcO—CH₂—C(=CH₂)—CH₂—S—(CH₂)₁₀—COOCH₃
Galβ1→2ManO—CH₂—CH(CH₂—S—(CH₂)₁₅—CH₃)₂
Galβ1→2ManO—CH₂—CH(CH₂—SO₂—(CH₂)₁₅—CH₃)₂
Galβ1→2ManO—CH₂—CH(CH₂—SO₂—(CH₂)₁₀—COOCH₃)—CH₂—SO₂—(CH₂)₇—CH₃
Galβ1→2ManO—CH₂—CH(CH₂—SO₂—CH₂—CH₃)₂
Galβ1→2ManO—CH₂—C(=CH₂)—CH₂—S—(CH₂)₂—COOCH₃

Galβ1→2ManO—CH$_2$—C(=CH$_2$)—CH$_2$—S—(CH$_2$)$_{10}$—COOCH$_3$
Fucα1→3GlcNAcO—CH$_2$—CH(CH$_2$—S—(CH$_2$)$_{15}$—CH$_3$)$_2$
Fucα1→3GlcNAcO—CH$_2$—CH(CH$_2$—SO$_2$—(CH$_2$)$_{15}$—CH$_3$)$_2$
Fucα1→3GlcNAcO—CH$_2$—CH(CH$_2$—SO$_2$—(CH$_2$)$_{10}$—COOCH$_3$)—CH$_2$—SO$_2$—(CH$_2$)$_7$—CH$_3$
Fucα1→3GlcNAcO—CH$_2$—CH(CH$_2$—SO$_2$—CH$_2$—CH$_3$)$_2$
Fucα1→3GlcNAcO—CH$_2$—C(=CH$_2$)—CH$_2$—S—(CH$_2$)$_2$—COOCH$_3$
Fucα1→3GlcNAcO—CH$_2$—C(=CH$_2$)—CH$_2$—S—(CH$_2$)$_{10}$—COOCH$_3$
Fucα1→2GalO—CH$_2$—CH(CH$_2$—S—(CH$_2$)$_{15}$—CH$_3$)$_2$
Fucα1→2GalO—CH$_2$—CH(CH$_2$—SO$_2$—(CH$_2$)$_{15}$—CH$_3$)$_2$
Fucα1→2GalO—CH$_2$—CH(CH$_2$—SO$_2$—(CH$_2$)$_{10}$—COOCH$_3$)—CH$_2$—SO$_2$—(CH$_2$)$_7$—CH$_3$
Fucα1→2GalO—CH$_2$—CH(CH$_2$—SO$_2$—CH$_2$—CH$_3$)$_2$
Fucα1→2GalO—CH$_2$—C(=CH$_2$)—CH$_2$—S—(CH$_2$)$_2$—COOCH$_3$
Fucα1→2GalO—CH$_2$—C(=CH$_2$)—CH$_2$—S—(CH$_2$)$_{10}$—COOCH$_3$
Fucα1→3GalO—CH$_2$—CH(CH$_2$—S—(CH$_2$)$_{15}$—CH$_3$)$_2$
Fucα1→3GalO—CH$_2$—CH(CH$_2$—SO$_2$—(CH$_2$)$_{15}$—CH$_3$)$_2$
Fucα1→3GalO—CH$_2$—CH(CH$_2$—SO$_2$—(CH$_2$)$_{10}$—COOCH$_3$)—CH$_2$—SO$_2$—(CH$_2$)$_7$—CH$_3$
Fucα1→3GalO—CH$_2$—CH(CH$_2$—SO$_2$—CH$_2$—CH$_3$)$_2$
Fucα1→3GalO—CH$_2$—C(=CH$_2$)—CH$_2$—S—(CH$_2$)$_2$—COOCH$_3$
Fucα1→3GalO—CH$_2$—C(=CH$_2$)—CH$_2$—S—(CH$_2$)$_{10}$—COOCH$_3$
Fucα1→6GalO—CH$_2$—CH(CH$_2$—S—(CH$_2$)$_{15}$—CH$_3$)$_2$
Fucα1→6GalO—CH$_2$—CH(CH$_2$—SO$_2$—(CH$_2$)$_{15}$—CH$_3$)$_2$
Fucα1→6GalO—CH$_2$—CH(CH$_2$—SO$_2$—(CH$_2$)$_{10}$—COOCH$_3$)—CH$_2$—SO$_2$—(CH$_2$)$_7$—CH$_3$
Fucα1→6GalO—CH$_2$—CH(CH$_2$—SO$_2$—CH$_2$—CH$_3$)$_2$
Fucα1→6GalO—CH$_2$—C(=CH$_2$)—CH$_2$—S—(CH$_2$)$_2$—COOCH$_3$
Fucα1→6GalO—CH$_2$—C(=CH$_2$)—CH$_2$—S—(CH$_2$)$_{10}$—COOCH$_3$
Galβ1→3GlcNAcO—CH$_2$—CH(CH$_2$—S—(CH$_2$)$_{15}$—CH$_3$)$_2$
Galβ1→3GlcNAcO—CH$_2$—CH(CH$_2$—SO$_2$—(CH$_2$)$_{15}$—CH$_3$)$_2$
Galβ1→3GlcNAcO—CH$_2$—CH(CH$_2$—SO$_2$—(CH$_2$)$_{10}$—COOCH$_3$)—CH$_2$—SO$_2$—(CH$_2$)$_7$—CH$_3$
Galβ1→3GlcNAcO—CH$_2$—CH(CH$_2$—SO$_2$—CH$_2$—CH$_3$)$_2$
Galβ1→3GlcNAcO—CH$_2$—C(=CH$_2$)—CH$_2$—S—(CH$_2$)$_2$—COOCH$_3$
Galβ1→3GlcNAcO—CH$_2$—C(=CH$_2$)—CH$_2$—S—(CH$_2$)$_{10}$—COOCH$_3$
Galβ1→2GalO—CH$_2$—CH(CH$_2$—S—(CH$_2$)$_{15}$—CH$_3$)$_2$
Galβ1→2GalO—CH$_2$—CH(CH$_2$—SO$_2$—(CH$_2$)$_{15}$—CH$_3$)$_2$
Galβ1→2GalO—CH$_2$—CH(CH$_2$—SO$_2$—(CH$_2$)$_{10}$—COOCH$_3$)—CH$_2$—SO$_2$—(CH$_2$)$_7$—CH$_3$
Galβ1→2GalO—CH$_2$—CH(CH$_2$—SO$_2$—CH$_2$—CH$_3$)$_2$
Galβ1→2GalO—CH$_2$—C(=CH$_2$)—CH$_2$—S—(CH$_2$)$_2$—COOCH$_3$
Galβ1→2GalO—CH$_2$—C(=CH$_2$)—CH$_2$—S—(CH$_2$)$_{10}$—COOCH$_3$
Galβ1→6GalO—CH$_2$—CH(CH$_2$—S—(CH$_2$)$_{15}$—CH$_3$)$_2$
Galβ1→6GalO—CH$_2$—CH(CH$_2$—SO$_2$—(CH$_2$)$_{15}$—CH$_3$)$_2$
Galβ1→6GalO—CH$_2$—CH(CH$_2$—SO$_2$—(CH$_2$)$_{10}$—COOCH$_3$)—CH$_2$—SO$_2$—(CH$_2$)$_7$—CH$_3$
Galβ1→6GalO—CH$_2$—CH(CH$_2$—SO$_2$—CH$_2$—CH$_3$)$_2$
Galβ1→6GalO—CH$_2$—C(=CH$_2$)—CH$_2$—S—(CH$_2$)$_2$—COOCH$_3$
Galβ1→6GalO—CH$_2$—C(=CH$_2$)—CH$_2$—S—(CH$_2$)$_{10}$—COOCH$_3$
Galβ1→3GalO—CH$_2$—CH(CH$_2$—S—(CH$_2$)$_{15}$—CH$_3$)$_2$
Galβ1→3GalO—CH$_2$—CH(CH$_2$—SO$_2$—(CH$_2$)$_{15}$—CH$_3$)$_2$
Galβ1→3GalO—CH$_2$—CH(CH$_2$—SO$_2$—(CH$_2$)$_{10}$—COOCH$_3$)—CH$_2$—SO$_2$—(CH$_2$)$_7$—CH$_3$
Galβ1→3GalO—CH$_2$—CH(CH$_2$—SO$_2$—CH$_2$—CH$_3$)$_2$
Galβ1→3GalO—CH$_2$—C(=CH$_2$)—CH$_2$—S—(CH$_2$)$_2$—COOCH$_3$
Galβ1→3GalO—CH$_2$—C(=CH$_2$)—CH$_2$—S—(CH$_2$)$_{10}$—COOCH$_3$
GalNAcα1→3GalO—CH$_2$—CH(CH$_2$—S—(CH$_2$)$_{15}$—CH$_3$)$_2$
GalNAcα1→3GalO—CH$_2$—CH(CH$_2$—SO$_2$—(CH$_2$)$_{15}$—CH$_3$)$_2$
GalNAcα1→3GalO—CH$_2$—CH(CH$_2$—SO$_2$—(CH$_2$)$_{10}$—COOCH$_3$)—CH$_2$—SO$_2$—(CH$_2$)$_7$—CH$_3$
GalNAcα1→3GalO—CH$_2$—CH(CH$_2$—SO$_2$—CH$_2$—CH$_3$)$_2$
GalNAcα1→3GalO—CH$_2$—C(=CH$_2$)—CH$_2$—S—(CH$_2$)$_2$—COOCH$_3$
GalNAcα1→3GalO—CH$_2$—C(=CH$_2$)—CH$_2$—S—(CH$_2$)$_{10}$—COOCH$_3$
GlcNAcβ1→3GalO—CH$_2$—CH(CH$_2$—S—(CH$_2$)$_{15}$—CH$_3$)$_2$
GlcNAcβ1→3GalO—CH$_2$—CH(CH$_2$—SO$_2$—(CH$_2$)$_{15}$—CH$_3$)$_2$
GlcNAcβ1→3GalO—CH$_2$—CH(CH$_2$—SO$_2$—(CH$_2$)$_{10}$—COOCH$_3$)—CH$_2$—SO$_2$—(CH$_2$)$_7$—CH$_3$
GlcNAcβ1→3GalO—CH$_2$—CH(CH$_2$—SO$_2$—CH$_2$—CH$_3$)$_2$
GlcNAcβ1→3GalO—CH$_2$—C(=CH$_2$)—CH$_2$—S—(CH$_2$)$_2$—COOCH$_3$
GlcNAcβ1→3GalO—CH$_2$—C(=CH$_2$)—CH$_2$—S—(CH$_2$)$_{10}$—COOCH$_3$
Galβ1→4GlcO—CH$_2$—CH(CH$_2$—S—(CH$_2$)$_{15}$—CH$_3$)$_2$
Galβ1→4GlcO—CH$_2$—CH(CH$_2$—SO$_2$—(CH$_2$)$_{15}$—CH$_3$)$_2$
Galβ1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
Galβ1→4GlcO—CH$_2$—CH(CH$_2$—SO$_2$—CH$_2$—CH$_3$)$_2$
Galβ1→4GlcO—CH$_2$—C(=CH$_2$)—CH$_2$—S—(CH$_2$)$_2$—COOCH$_3$

Galβ1→4GlcO—CH$_2$—C(=CH$_2$)—CH$_2$—S—(CH$_2$)$_{10}$—COOCH$_3$
Galα1→4GalO—CH$_2$—CH(CH$_2$—S—(CH$_2$)$_{15}$—CH$_3$)$_2$
Galα1→4GalO—CH$_2$—CH(CH$_2$—SO$_2$—(CH$_2$)$_{15}$—CH$_3$)$_2$
Galα1→4GalO—CH$_2$—CH(CH$_2$—SO$_2$—(CH$_2$)$_{10}$—COOCH$_3$)—CH$_2$—SO$_2$—(CH$_2$)$_7$—CH$_3$
Galα1→4GalO—CH$_2$—CH(CH$_2$—SO$_2$—CH$_2$—CH$_3$)$_2$
Galα1→4GalO—CH$_2$—C(=CH$_2$)—CH$_2$—S—(CH$_2$)$_2$—COOCH$_3$
Galα1→4GalO—CH$_2$—C(=CH$_2$)—CH$_2$—S—(CH$_2$)$_{10}$—COOCH$_3$
GalNAcβ1→3GalO—CH$_2$—CH(CH$_2$—S—(CH$_2$)$_{15}$—CH$_3$)$_2$
GalNAcβ1→3GalO—CH$_2$—CH(CH$_2$—SO$_2$—(CH$_2$)$_{15}$—CH$_3$)$_2$
GalNAcβ1→3GalO—CH$_2$—CH(CH$_2$—SO$_2$—(CH$_2$)$_{10}$—COOCH$_3$)—CH$_2$—SO$_2$—(CH$_2$)$_7$—CH$_3$
GalNAcβ1→3GalO—CH$_2$—CH(CH$_2$—SO$_2$—CH$_2$—CH$_3$)$_2$
GalNAcβ1→3GalO—CH$_2$—C(=CH$_2$)—CH$_2$—S—(CH$_2$)$_2$—COOCH$_3$
GalNAcβ1→3GalO—CH$_2$—C(=CH$_2$)—CH$_2$—S—(CH$_2$)$_{10}$—COOCH$_3$
GalNAcα1→3GalNAcO—CH$_2$—CH(CH$_2$—S—(CH$_2$)$_{15}$—CH$_3$)$_2$
GalNAcα1→3GalNAcO—CH$_2$—CH(CH$_2$—SO$_2$—(CH$_2$)$_{15}$—CH$_3$)$_2$
GalNAcα1→3GalNAcO—CH$_2$—CH(CH$_2$—SO$_2$—(CH$_2$)$_{10}$—COOCH$_3$)—CH$_2$—SO$_2$—(CH$_2$)$_7$—CH$_3$
GalNAcα1→3GalNAcO—CH$_2$—CH(CH$_2$—SO$_2$—CH$_2$—CH$_3$)$_2$
GalNAcα1→3GalNAcO—CH$_2$—C(=CH$_2$)—CH$_2$—S—(CH$_2$)$_2$—COOCH$_3$
GalNAcα1→3GalNAcO—CH$_2$—C(=CH$_2$)—CH$_2$—S—(CH$_2$)$_{10}$—COOCH$_3$
GalNAcβ1→4GalO—CH$_2$—CH(CH$_2$—S—(CH$_2$)$_{15}$—CH$_3$)$_2$
GalNAcβ1→4GalO—CH$_2$—CH(CH$_2$—SO$_2$—(CH$_2$)$_{15}$—CH$_3$)$_2$
GalNAcβ1→4GalO—CH$_2$—CH(CH$_2$—SO$_2$—(CH$_2$)$_{10}$—COOCH$_3$)—CH$_2$—SO$_2$—(CH$_2$)$_7$—CH$_3$
GalNAcβ1→4GalO—CH$_2$—CH(CH$_2$—SO$_2$—CH$_2$—CH$_3$)$_2$
GalNAcβ1→4GalO—CH$_2$—C(=CH$_2$)—CH$_2$—S—(CH$_2$)$_2$—COOCH$_3$
GalNAcβ1→4GalO—CH$_2$—C(=CH$_2$)—CH$_2$—S—(CH$_2$)$_{10}$—COOCH$_3$
Galβ1→3GalNAcO—CH$_2$—CH(CH$_2$—S—(CH$_2$)$_{15}$—CH$_3$)$_2$
Galβ1→3GalNAcO—CH$_2$—CH(CH$_2$—SO$_2$—(CH$_2$)$_{15}$—CH$_3$)$_2$
Galβ1→3GalNAcO—CH$_2$—CH(CH$_2$—SO$_2$—(CH$_2$)$_{10}$—COOCH$_3$)—CH$_2$—SO$_2$—(CH$_2$)$_7$—CH$_3$
Galβ1→3GalNAcO—CH$_2$—CH(CH$_2$—SO$_2$—CH$_2$—CH$_3$)$_2$
Galβ1→3GalNAcO—CH$_2$—C(=CH$_2$)—CH$_2$—S—(CH$_2$)$_2$—COOCH$_3$
Galβ1→3GalNAcO—CH$_2$—C(=CH$_2$)—CH$_2$—S—(CH$_2$)$_{10}$—COOCH$_3$
Galα1→3GalO—CH$_2$—CH(CH$_2$—S—(CH$_2$)$_{15}$—CH$_3$)$_2$
Galα1→3GalO—CH$_2$—CH(CH$_2$—SO$_2$—(CH$_2$)$_{15}$—CH$_3$)$_2$
Galα1→3GalO—CH$_2$—CH(CH$_2$—SO$_2$—(CH$_2$)$_{10}$—COOCH$_3$)—CH$_2$—SO$_2$—(CH$_2$)$_7$—CH$_3$
Galα1→3GalO—CH$_2$—CH(CH$_2$—SO$_2$—CH$_2$—CH$_3$)$_2$
Galα1→3GalO—CH$_2$—C(=CH$_2$)—CH$_2$—S—(CH$_2$)$_2$—COOCH$_3$
Galα1→3GalO—CH$_2$—C(=CH$_2$)—CH$_2$—S—(CH$_2$)$_{10}$—COOCH$_3$
Glcα1→6Glcα1→4Glcα1→4GlcO—CH$_2$—CH(CH$_2$—S—(CH$_2$)$_{15}$—CH$_3$)$_2$
Glcα1→6Glcα1→4Glcα1→4GlcO—CH$_2$—CH(CH$_2$—SO$_2$—(CH$_2$)$_{15}$—CH$_3$)$_2$
Glcα1→6Glcα1→4Glcα1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
Glcα1→6Glcα1→4Glcα1→4GlcO—CH$_2$—CH(CH$_2$—SO$_2$—CH$_2$—CH$_3$)$_2$
Glcα1→6Glcα1→4Glcα1→4GlcO—CH$_2$—C(=CH$_2$)—CH$_2$—S—(CH$_2$)$_2$—COOCH$_3$
Glcα1→6Glcα1→4Glcα1→4GlcO—CH$_2$—C(=CH$_2$)—CH$_2$—S—(CH$_2$)$_{10}$—COOCH$_3$
Glcα1→4GlcO—CH$_2$—CH(CH$_2$—S—(CH$_2$)$_{15}$—CH$_3$)$_2$
Glcα1→4GlcO—CH$_2$—CH(CH$_2$—SO$_2$—(CH$_2$)$_{15}$—CH$_3$)$_2$
Glcα1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
Glcα1→4GlcO—CH$_2$—CH(CH$_2$—SO$_2$—CH$_2$—CH$_3$)$_2$
Glcα1→4GlcO—CH$_2$—C(=CH$_2$)—CH$_2$—S—(CH$_2$)$_2$—COOCH$_3$
Glcα1→4GlcO—CH$_2$—C(=CH$_2$)—CH$_2$—S—(CH$_2$)$_{10}$—COOCH$_3$
Glcβ1→4GlcO—CH$_2$—CH(CH$_2$—S—(CH$_2$)$_{15}$—CH$_3$)$_2$
Glcβ1→4GlcO—CH$_2$—CH(CH$_2$—SO$_2$—(CH$_2$)$_{15}$—CH$_3$)$_2$
Glcβ1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
Glcβ1→4GlcO—CH$_2$—CH(CH$_2$—SO$_2$—CH$_2$—CH$_3$)$_2$
Glcβ1→4GlcO—CH$_2$—C(=CH$_2$)—CH$_2$—S—(CH$_2$)$_2$—COOCH$_3$
Glcβ1→4GlcO—CH$_2$—C(=CH$_2$)—CH$_2$—S—(CH$_2$)$_{10}$—COOCH$_3$
NeuNAcα2→3GalO—CH$_2$—CH(CH$_2$—S—(CH$_2$)$_{15}$—CH$_3$)$_2$
NeuNAcα2→3GalO—CH$_2$—CH(CH$_2$—SO$_2$—(CH$_2$)$_{15}$—CH$_3$)$_2$
NeuNAcα2→3GalO—CH$_2$—CH(CH$_2$—SO$_2$—(CH$_2$)$_{10}$—COOCH$_3$)—CH$_2$—SO$_2$—(CH$_2$)$_7$—CH$_3$
NeuNAcα2→3GalO—CH$_2$—CH(CH$_2$—SO$_2$—CH$_2$—CH$_3$)$_2$
NeuNAcα2→3GalO—CH$_2$—C(=CH$_2$)—CH$_2$—S—(CH$_2$)$_2$—COOCH$_3$
NeuNAcα2→3GalO—CH$_2$—C(=CH$_2$)—CH$_2$—S—(CH$_2$)$_{10}$—COOCH$_3$
NeuNAcα2→6GalO—CH$_2$—CH(CH$_2$—S—(CH$_2$)$_{15}$—CH$_3$)$_2$
NeuNAcα2→6GalO—CH$_2$—CH(CH$_2$—SO$_2$—(CH$_2$)$_{15}$—CH$_3$)$_2$
NeuNAcα2→6GalO—CH$_2$—CH(CH$_2$—SO$_2$—(CH$_2$)$_{10}$—COOCH$_3$)—CH$_2$—SO$_2$—(CH$_2$)$_7$—CH$_3$
NeuNAcα2→6GalO—CH$_2$—CH(CH$_2$—SO$_2$—CH$_2$—CH$_3$)$_2$

NeuNAcα2→6GalO—CH$_2$—C(=CH$_2$)—CH$_2$—S—(CH$_2$)$_2$—COOCH$_3$
NeuNAcα2→6GalO—CH$_2$—C(=CH$_2$)—CH$_2$—S—(CH$_2$)$_{10}$—COOCH$_3$
NeuNAcα2→3GalNAcO—CH$_2$—CH(CH$_2$—S—(CH$_2$)$_{15}$—CH$_3$)$_2$
NeuNAcα2→3GalNAcO—CH$_2$—CH(CH$_2$—SO$_2$—(CH$_2$)$_{15}$—CH$_3$)$_2$
NeuNAcα2→3GalNAcO—CH$_2$—CH(CH$_2$—SO$_2$—(CH$_2$)$_{10}$—COOCH$_3$)—CH$_2$—SO$_2$—(CH$_2$)$_7$—CH$_3$
NeuNAcα2→3GalNAcO—CH$_2$—CH(CH$_2$—SO$_2$—CH$_2$—CH$_3$)$_2$
NeuNAcα2→3GalNAcO—CH$_2$—C(=CH$_2$)—CH$_2$—S—(CH$_2$)$_2$—COOCH$_3$
NeuNAcα2→3GalNAcO—CH$_2$—C(=CH$_2$)—S—(CH$_2$)$_{10}$—COOCH$_3$
NeuNAcα2→6GlcNAcO—CH$_2$—CH(CH$_2$—S—(CH$_2$)$_{15}$—CH$_3$)$_2$
NeuNAcα2→6GlcNAcO—CH$_2$—CH(CH$_2$—SO$_2$—(CH$_2$)$_{15}$—CH$_3$)$_2$
NeuNAcα2→6GlcNAcO—CH$_2$—CH(CH$_2$—SO$_2$—(CH$_2$)$_{10}$—COOCH$_3$)—CH$_2$—SO$_2$—(CH$_2$)$_7$—CH$_3$
NeuNAcα2→6GlcNAcO—CH$_2$—CH(CH$_2$—SO$_2$—CH$_2$—CH$_3$)$_2$
NeuNAcα2→6GlcNAcO—CH$_2$—C(=CH$_2$)—CH$_2$—S—(CH$_2$)$_2$—COOCH$_3$
NeuNAcα2→6GlcNAcO—CH$_2$—C(=CH$_2$)—CH$_2$—S—(CH$_2$)$_{10}$—COOCH$_3$
NeuNAcα2→8NeuNAcO—CH$_2$—CH(CH$_2$—S—(CH$_2$)$_{15}$—CH$_3$)$_2$
NeuNAcα2→8NeuNAcO—CH$_2$—CH(CH$_2$—SO$_2$—(CH$_2$)$_{15}$—CH$_3$)$_2$
NeuNAcα2→8NeuNAcO—CH$_2$—CH(CH$_2$—SO$_2$—(CH$_2$)$_{10}$—COOCH$_3$)—CH$_2$—SO$_2$—(CH$_2$)$_7$—CH$_3$
NeuNAcα2→8NeuNAcO—CH$_2$—CH(CH$_2$—SO$_2$—CH$_2$—CH$_3$)$_2$
NeuNAcα2→8NeuNAcO—CH$_2$—C(=CH$_2$)—CH$_2$—S—(CH$_2$)$_2$—COOCH$_3$
NeuNAcα2→8NeuNAcO—CH—C(=CH$_2$)—S—(CH$_2$)$_{10}$—COOCH$_3$
Glcβ1→4Glcβ1→4GlcO—CH$_2$—CH(CH$_2$—S—(CH$_2$)$_{15}$—CH$_3$)$_2$
Glcβ1→4Glcβ1→4GlcO—CH$_2$—CH(CH$_2$—SO$_2$—(CH$_2$)$_{15}$—CH$_3$)$_2$
Glcβ1→4Glcβ1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
Glcβ1→4Glcβ1→4GlcO—CH$_2$—CH(CH$_2$—SO$_2$—CH$_2$—CH$_3$)$_2$
Glcβ1→4Glcβ1→4GlcO—CH$_2$—C(=CH$_2$)—CH$_2$—S—(CH$_2$)$_2$—COOCH$_3$
Glcβ1→4Glcβ1→4GlcO—CH$_2$—C(=CH$_2$)—CH$_2$—S—(CH$_2$)$_{10}$—COOCH$_3$
Glcα1→4Glcα1→4GlcO—CH$_2$—CH(CH$_2$—S—(CH$_2$)$_{15}$—CH$_3$)$_2$
Glcα1→4Glcα1→4GlcO—CH$_2$—CH(CH$_2$—SO$_2$—(CH$_2$)$_{15}$—CH$_3$)$_2$
Glcα1→4Glcα1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
Glcα1→4Glcα1→4GlcO—CH$_2$—CH(CH$_2$—SO$_2$—CH$_2$—CH$_3$)$_2$
Glcα1→4Glcα1→4GlcO—CH$_2$—C(=CH$_2$)—CH$_2$—S—(CH$_2$)$_2$—COOCH$_3$
Glcα1→4Glcα1→4GlcO—CH$_2$—C(=CH$_2$)—CH$_2$—S—(CH$_2$)$_{10}$—COOCH$_3$
Manα1→3(Manα1→6)ManO—CH$_2$—CH(CH$_2$—S—(CH$_2$)$_{15}$—CH$_3$)$_2$
Manα1→3(Manα1→6)ManO—CH$_2$—CH(CH$_2$—SO$_2$—(CH$_2$)$_{15}$—CH$_3$)$_2$
Manα1→3(Manα1→6)ManO—CH$_2$—CH(CH$_2$—SO$_2$—(CH$_2$)$_{10}$—COOCH$_3$)—CH$_2$—SO$_2$—(CH$_2$)$_7$—CH$_3$
Manα1→3(Manα1→6)ManO—CH$_2$—CH(CH$_2$—SO$_2$CH$_2$—CH$_3$)$_2$
Manα1→3(Manα1→6)ManO—CH$_2$—C(=CH$_2$)—CH$_2$—S—(CH$_2$)$_2$—COOCH$_3$
Manα1→3(Manα1→6)ManO—CH$_2$—C(=CH$_2$)—CH$_2$—S—(CH$_2$)$_{10}$—COOCH$_3$
Galβ1→3GalNAcβ1→4Galβ1-4GlcO—CH$_2$—CH(CH$_2$—S—(CH$_2$)$_{15}$—CH$_3$)$_2$
Galβ1→3GalNAcβ1→4Galβ1-4GlcO—CH$_2$—CH(CH$_2$—SO$_2$—(CH$_2$)$_{15}$—CH$_3$)$_2$
Galβ1→3GalNAcβ1→4Galβ1-4GlcO—CH$_2$—CH(CH$_2$—SO$_2$—(CH$_2$)$_{10}$—COOCH$_3$)—CH$_2$—SO$_2$—(CH$_2$)$_7$—Ch$_3$
Galβ1→3GalNAcβ1→4Galβ1-4GlcO—CH$_2$—CH(CH$_2$—SO$_2$—CH$_2$—CH$_3$)$_2$
Galβ1→3GalNAcβ1→4Galβ1-4GlcO—CH$_2$C(=CH$_2$)—CH$_2$—S—(CH$_2$)$_2$—COOCH$_3$
Galβ1→3GalNAcβ1→4Galβ1-4GlcO—CH$_2$C(=CH$_2$)—CH$_2$S—(CH$_2$)$_{10}$—COOCH$_3$
GalNAcβ1→4Galβ1→3GalNAcβ1→4Galβ1→4GlcO—CH$_2$—CH(CH$_2$—S—(CH$_2$)$_{15}$—CH$_3$)$_2$
GalNAcβ1→4Galβ1→3GalNAcβ1→4Galβ1→4GlcO—CH$_2$—CH(CH$_2$—SO$_2$—(CH$_2$)$_{15}$—CH$_3$)$_2$
GalNAcβ1→4Galβ1→3GalNAcβ1→4Galβ1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
GalNAcβ1→4Galβ1→3GalNAcβ1→4Galβ1→4GlcO—CH$_2$—CH(CH$_2$—SO$_2$—CH$_2$—CH$_3$)$_2$
GalNAcβ1→4Galβ1→3GalNAcβ1→4Galβ1→4GlcO—CH$_2$—C(=CH$_2$)—CH$_2$—S—(CH$_2$)$_2$—COOCH$_3$
GalNAcβ1→4Galβ1→3GalNAcβ1→4Galβ1→4GlcO—CH$_2$—C(=CH$_2$)—CH$_2$—S—(CH$_2$)$_{10}$—COOCH$_3$
GalNAcβ1→3Galα1→4galβ1→4GlcO—CH$_2$—CH(CH$_2$—S—(CH$_2$)$_{15}$—CH$_3$)$_2$
GalNAcβ1→3Galα1→4Galβ1→4GlcO—CH$_2$—CH(CH$_2$—SO$_2$—(CH$_2$)$_{15}$—CH$_3$)$_2$
GalNAcβ1→3Galα1→4Galβ1→4GlcO—CH$_2$—CH(CH$_2$—SO$_2$—(CH$_2$)$_{10}$—COOCH$_3$)—CH$_2$SO$_2$—(CH$_2$)$_7$—CH$_3$
GalNAcβ1→3Galα1→4Galβ1→4GlcO—CH$_2$—CH(CH$_2$—SO$_2$—CH$_2$—CH$_3$)$_2$
GalNAcβ1→3Galα1→4Galβ1→4GlcO—CH$_2$—C(=CH$_2$)—CH$_2$—S—(CH$_2$)$_2$—COOCH$_3$
GalNAcβ1→3Galα1→4Galβ1→4GlcO—CH$_2$—C(=CH$_2$—S—(CH$_2$)$_{10}$—COOCH$_3$
GalNAcβ1→3Galα1→3Galβ1→4GlcO—CH$_2$—CH(CH$_2$—S—(CH$_2$)$_{15}$—CH$_3$)$_2$
GalNAcβ1→3Galα1→3Galβ1→4GlcO—CH$_2$—CH(CH$_2$—SO$_2$—(CH$_2$)$_{15}$—CH$_3$)$_2$ GalNAcβ1→3Galα1→3Galβ1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$ GalNAcβ1→3Galα1→3Galβ1→4GlcO—CH$_2$—CH(CH$_2$—SO$_2$—CH$_2$—CH$_3$)$_2$ GalNAcβ1→3Galα1→3Galβ1→4GlcO—CH$_2$—C(=CH$_2$)—CH$_2$—S—(CH$_2$)$_2$—COOCH$_3$ GalNAcβ1→3Galα1→3Galβ1→4GlcO—CH$_2$—C(=CH$_2$)—CH$_2$—S—(CH$_2$)$_{10}$—COOCH$_3$ Galβ1→4GlcNAcβ1→3Galβ1→4GlcO—CH$_2$—CH(CH$_2$S—(CH$_2$)$_{15}$—CH$_3$)$_2$ Galβ1→4GlcNAcβ1→3Galβ1→4GlcO—CH$_2$—CH(CH$_2$—SO$_2$—(CH$_2$)$_{15}$—CH$_3$)$_2$ Galβ1→4GlcNAcβ1→3Galβ1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$ Galβ1→4GlcNAcβ1→3Galβ1→4GlcO—CH$_2$—CH(CH$_2$—SO$_2$—CH$_2$—CH$_3$)$_2$ Galβ1→4GlcNAcβ1→3Galβ1→4GlcO—CH$_2$—C(=CH$_2$)—CH$_2$—S—(CH$_2$)$_2$—COOCH$_3$ Galβ1→4GlcNAcβ1→3Galβ1→4GlcO—CH$_2$—C(=CH$_2$)—CH$_2$—S—(CH$_2$)$_{10}$—COOCH$_3$ Galβ1→3GlcNAcβ1→3Galβ1→3Galβ1→4GlcO—CH$_2$—CH(CH$_2$—S—(CH$_2$)$_{15}$—CH$_3$)$_2$ Galβ1→3GlcNAcβ1→3Galβ1→3Galβ1→4GlcO—CH$_2$—CH(CH$_2$—SO$_2$—(CH$_2$)$_{15}$—CH$_3$)$_2$ Galβ1→3GlcNAcβ1→3Galβ1→3Galβ1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$ Galβ1→3GlcNAcβ1→3Galβ1→3Galβ1→4GlcO—CH$_2$—CH(CH$_2$—SO$_2$—CH$_2$—CH$_3$)$_2$ Galβ1→3GlcNAcβ1→3Galβ1→3Galβ1→4GlcO—CH$_2$—C(=CH$_2$)—CH$_2$—S—(CH$_2$)$_2$—COOCH$_3$ Galβ1→3GlcNAcβ1→3Galβ1→3Galβ1→4GlcO—CH$_2$—C(=CH$_2$)—CH$_2$—S—(CH$_2$)$_{10}$—COOCH$_3$ Galβ1→4GlcNAcβ1→3Galβ1→4GlcNAcβ1→3Galβ1→4GlcO—CH$_2$—CH(CH$_2$—S—(CH$_2$)$_{15}$—CH$_3$)$_2$ Galβ1→4GlcNAcβ1→3Galβ1→4GlcNAcβ1→Galβ1→4GlcO—CH$_2$—CH(CH$_2$SO$_2$—(CH$_2$)$_{15}$—CH$_3$)$_2$ Galβ1→4GlcNAcβ1→3-Galβ1→4GlcNAcβ1→3Galβ1→4GlcO—CH$_2$—CH(CH$_2$—(CH$_2$—SO$_2$—(CH$_2$)$_{10}$—COOCH$_3$)—CH$_2$—SO$_2$—(CH$_2$)$_7$CH$_3$ Galβ1→4GlcNAcβ1→3GlcNAcβ1→3Galβ1→4GlcO—CH$_2$—CH(CH$_2$—SO$_2$—CH$_2$—CH$_3$)$_2$ Galβ1→4GlcNAcβ1→3Galβ1→4GlcNAcβ1→3Galβ1→4GlcO—CH$_2$—C(=CH$_2$)—CH$_2$—S—(CH$_2$)—*COOCH3*

Galβ1→4GlcNAcβ1→3Galβ1→4GlcNAcβ1→3Galβ1→4GlcO—CH$_2$—C(=CH$_2$)—CH$_2$—S—(CH$_2$)$_{10}$—COOCH$_3$

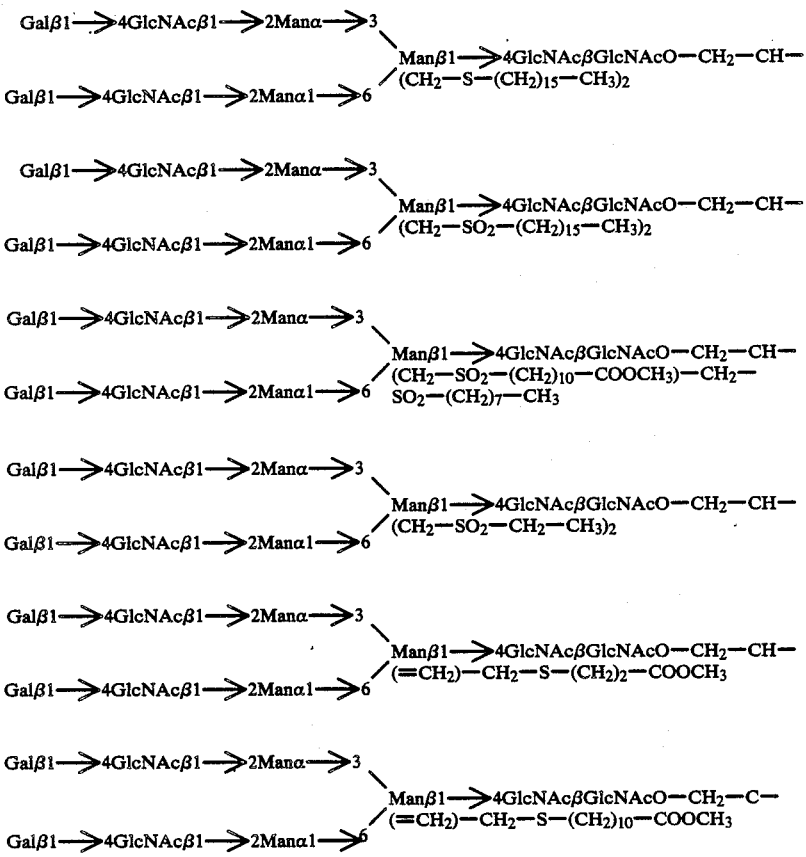

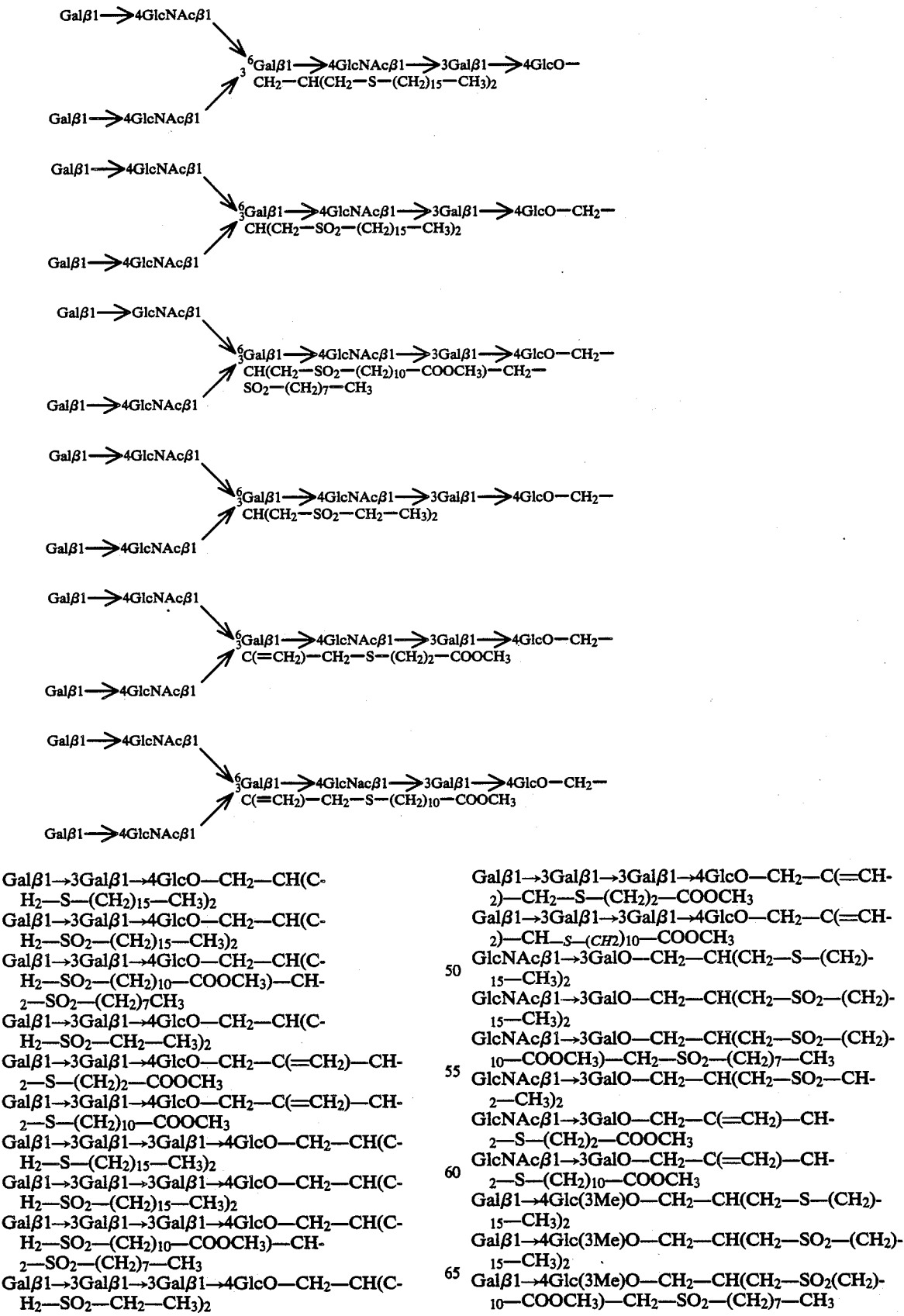

Galβ1→4Glc(3Me)O—CH$_2$—CH(CH$_2$—SO$_2$—CH$_2$—CH$_3$)$_2$
Galβ1→4Glc(3Me)O—CH$_2$—C(=CH$_2$)—CH$_2$—S—(CH$_2$)$_2$—COOCH$_3$
Galβ1→4Glc(3Me)O—CH$_2$C(=CH$_2$)—CH$_2$—S—(CH$_2$)$_{10}$—COOCH$_3$
Galα1→4Gal(3Me)O—CH$_2$—CH(CH$_2$—S—(CH$_2$)$_{15}$—CH$_3$)$_2$
Galα1→4Gal(3Me)O—CH$_2$—CH(CH$_2$—SO$_2$—(CH$_2$)$_{15}$—CH$_3$)$_2$
Galα1→4Gal(3Me)O—CH$_2$—CH(CH$_2$—SO$_2$—(CH$_2$)$_{10}$—COOCH$_3$)—CH$_2$—SO$_2$—(CH$_2$)$_7$—CH$_3$
Galα1→4Gal(3Me)O—CH$_2$—CH(CH$_2$—SO$_2$—CH$_2$CH$_3$)$_2$
Galα1→4Gal(3Me)O—CH$_2$—C(=CH$_2$)—CH$_2$—S—(CH$_2$)$_2$—COOCH$_3$
Galα1→4Gal(3Me)O—CH$_2$—C(=CH$_2$)—CH$_2$—S—(CH$_2$)$_{10}$—COOCH$_3$
Galβ1→4Glc(3CH$_2$OH)O—CH$_2$—CH(CH$_2$—S—(CH$_2$)$_{15}$—CH$_3$)$_2$
Galβ1→4Glc(3CH$_2$OH)O—CH$_2$—CH(CH$_2$—SO$_2$—(CH$_2$)$_{15}$—CH$_3$)$_2$
Galβ1→4Glc(3CH$_2$OH)O—CH$_2$—(CH$_2$—SO$_2$—(CH$_2$)$_{10}$—COOCH$_3$)—CH$_2$—SO$_2$—(CH$_2$)$_7$CH$_3$
Galβ1→4Glc(3CH$_2$OH)O—CH$_2$—CH(CH$_2$—SO$_2$—CH$_2$CH$_3$)$_2$
Galβ1→4Glc(3CH$_2$OH)O—CH$_2$—C(=CH$_2$)—CH$_2$—S—(CH$_2$)$_2$COOCH$_3$
Galβ1→4Glc(3CH$_2$OH)O—CH$_2$—C(=CH$_2$)—CH$_2$—S—(CH$_2$)$_{10}$—COOCH$_3$
Galα1→4Gal(3CH$_2$OH)O—CH$_2$—CH(CH$_2$—S—(CH$_2$)$_{15}$—CH$_3$)$_2$
Galα1→4Gal(3CH$_2$OH)O—CH$_2$—CH(CH$_2$—SO$_2$—(CH$_2$)$_{15}$CH$_3$)$_2$
Galα1→4Gal(3CH$_2$OH)O—CH$_2$—CH(CH$_2$—SO$_2$—(CH$_2$)$_{10}$—COOCH$_3$)—CH$_2$—SO$_2$—(CH$_2$)$_7$—CH$_3$
Galα1→4Gal(3CH$_2$OH)O—CH$_2$—CH(CH$_2$—SO$_2$—CH$_2$—CH$_3$)$_2$
Galα1→4Gal(3Ch$_2$OH)O—CH$_2$—C(=CH$_2$)—CH$_2$—S—(CH$_2$)$_2$—COOCH$_3$
Galα1→4Gal(3CH$_2$OH)O—CH$_2$—C(=CH$_2$)—$_{10}$—COOCH$_3$
Galα1→4Galβ1→4GlcO—CH$_2$—CH(CH$_2$—S—(CH$_2$)$_{15}$—CH$_3$)$_2$
Galα1→4Galβ1→4GlcO—CH$_2$—CH(CH$_2$—SO$_2$—(CH$_2$)$_{15}$—CH$_3$)$_2$
Galα1→4Galβ1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
Galα1→4Galβ1→4GlcO—CH$_2$—CH(CH$_2$—SO$_2$CH$_2$CH$_3$)$_2$
Galα1→4Gal β1→4GlcO—CH$_2$—C(=CH$_2$)—CH$_2$—S—(CH$_2$)$_2$—COOCH$_3$
Galα1→4Galβ1→4GlcO—CH$_2$—C(=CH$_2$)—CH$_2$—S—(CH$_2$)$_{10}$—COOCH$_3$
Galα1→4Galβ1→4GlcNAcO—CH$_2$—CH(CH$_2$—S—(CH$_2$)$_{15}$—CH$_3$)$_2$
galα1→4Galβ1→4GlcNAcO—CH$_2$—CH(CH$_2$—SO$_2$—(CH$_2$)$_{15}$—CH$_3$)$_2$
Galα1→4Galβ1→4GlcNAcO-CH$_2$—CH(CH$_2$—SO$_2$—(CH$_2$)$_{10}$—COOCH$_3$)—CH$_2$—SO—(CH$_2$)$_7$—CH$_3$
Galα1→4Galβ1→4GlcNAcO—CH$_2$—CH(CH$_2$—SO$_2$—CH$_2$—CH$_3$)$_2$
Galα1→4Galβ1→4GlcNAcO—CH$_2$—C(=CH$_2$)—CH$_2$—S—(CH$_2$)$_2$—COOCH$_3$
Galα1→4Galβ1→4GlcNAcO—CH$_2$—C(=CH$_2$)—CH$_2$—S—(CH$_2$)$_{10}$—COOCH$_3$
Glcα1→6Glcα1→4GlcO—CH$_2$—CH$_2$)—(CH$_2$—S—(CH$_2$)$_{15}$—CH$_3$)$_2$
Glcα1→6Glcα1→4GlcO—CH$_2$—CH(CH$_2$—SO$_2$—(CH$_2$)$_{15}$—CH$_3$)$_2$
Glcα1→6Glcα1→4GlcO—CH$_2$—CH(CH$_2$—SO$_2$—(CH$_2$)$_{10}$—COOCH$_3$)—CH$_2$—SO$_2$—(CH$_2$)$_7$—CH$_3$
Glcα1→6Glcα1→4GlcO—CH$_2$—CH(CH$_2$—SO$_2$—CH$_2$—CH$_3$)$_2$
Glcα1→6Glcα1→4GlcO—CH$_2$—C(=CH$_2$)—CH$_2$—S—(CH$_2$)$_2$—COOCH$_3$
Glcα1→6Glcα1→4GlcO—CH$_2$—C(=CH$_2$)—CH$_2$—S—(CH$_2$)$_{10}$—COOCH$_3$ In the compounds specified, the bond between the carbohydrate moiety in question and the aglycon moiety in question may be either in α- or β-configuration.

In a different class of interesting compounds of the formula I, $R_1$ and $R_3$ are H and $R_2$ is —SO$_2$—R$_4$—R$_5$ wherein $R_4$ and $R_5$ are as defined above. These compounds have a structure comprising a dimethylene group connecting the glycosidic oxygen and the sulphone group. As examples of the carbohydrate moiety in such compounds may be mentioned the carbohydrate moieties listed above.

Compounds whose aglycon moiety terminates in an amino, hydroxy or mercapto group are also interesting. Such compounds include compounds in which $R_3$ is H, and $R_1$ and $R_2$ are groups of the formula II, of the formula III wherein $R_6$ is the group —R$_4$-R$_5$, or the formula IIIa wherein $R_7$ and/or $R_7$ is a group —R$_4$-R$_5$, wherein $R_4$ is as defined above, and $R_5$ is NH$_2$, OH or SH as well as compounds wherein $R_2$ and $R_3$ together form =CH$_2$, and $R_1$ is a group of the formula II, of the formula III, or of the formula IIIa with the same characteristics. Such compounds have the potential of being able to react with compounds of the formula I wherein $R_3$ is H, and $R_1$ and $R_2$ independently are a group —CH$_2$X wherein X is a leaving group, or, in particular, compounds of the formula I in which $R_2$ and $R_3$ together form =CH$_2$, and $R_1$ is a group —CH$_2$X wherein X is a leaving group. Combination of compounds incorporating a free amino, hydroxy or mercapto group with compounds incorporating a leaving group X may result in the formation of bis- or tris-glycosides, thereby incorporating 2 or 3 carbohydrate moieties into the same relatively small molecule. The carbohydrate units may be identical, or they may be different thereby rendering possible the formation of compounds with multiple specificity.

The present invention also relates to a process for preparing an O-glycosidic compound of the formula I defined above.

A process (a) for preparing compounds in which $R_3$ is H, and $R_1$ and $R_2$ are —CH$_2$X, comprises reacting a sugar derivative of the formula V $$(\text{Sugar})_n—Y \qquad\qquad V$$

wherein Sugar and n are as defined above, and Y is acyl, halogen or a group —S—R$_9$, wherein R$_9$ is lower alkyl or aryl or constitutes a link between the anomeric oxygen and an oxygen or nitrogen atom in position 2 of the saccharide unit (id est the latter is an ortho ester or oxazoline derivative), with an alcohol of the formula IX

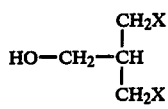

wherein X is as defined above.

The reactions may be carried out in an aprotic, polar or non-polar organic solvent such as methylene chloride, toluene, ether, or nitromethane. The reaction temperature is not critical, and the reaction may be carried out at temperatures ranging from $-78°$ C. to $+150°$ C., normally from $0°$ C. to $50°$ C. such as room temperature. The reaction time may be from 0.1 to 200 hours, normally 1–24 hours such as 16 hours. A particularly useful example of the alcohol IX is a 3-halo-2-halomethyl-propan-1-ol, in particular 3-bromo-2-bromomethyl-propan-1-ol (DlBol). Such alcohols and derivatives thereof are described in Applicant's copending Danish application entitled "Propanol Derivatives", filed on the same date as the present application. The alcohol of formula IX may be prepared by reduction with e.g. $NaBH_4$ of the corresponding acid where the acid is either known or may be prepared by known methods. The preparation of DlBol is exemplified in Preparation 1 below. The alcohol of formula IX may be used in an excess of 1–2 molar equivalents based on the sugar derivative, in particular if Y is acyl such as acetyl. The reaction may be carried out with the use of catalysts such as Lewis acids, e.g. $BF_3.Et_2O$ or $SnCl_4$, or metal salts such as silver oxide, silver carbonate, silver triflate, $HgBr_2$, $Hg(CN)_2$. The metal salts are particularly used if Y is halogen. Groups in the sugar derivative of the formula V that are sensitive to the reaction conditions may be protected. Thus, the hydroxy groups may be protected with acyl groups such as acetyl or benzoyl, with benzyl, or with a benzylidene group wherein the phenyl ring may be substituted with alkoxy in the 4-position. When benzylidene groups are used as protection groups, two hydroxy groups are protected for each benzylidene group. The product formed may be purified by methods known in the art such as extraction, crystallisation or chromatography (preferably on silica gel). The protecting groups may, if desired, then be removed by methods known in the art, optionally followed by further purification.

Another process (b) for preparing compounds in which $R_3$ is H, and $R_1$ and $R_2$ are of the formula II defined above comprises reacting an O-glycoside of the formula VI

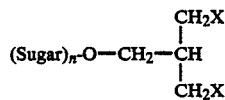

wherein Sugar, X and n are as defined above with a thiol of the formula VII

          VII wherein $R_4$ and $R_5$ are as defined above, and, if desired, reacting the product with an oxidizing agent.

The reaction may be carried out in water or in an aprotic or protic, polar or non-polar organic solvent such as ethyl acetate, methylene chloride, ether and dimethyl sulfoxide. The reaction temperature is not critical, and the reaction may be carried out at temperatures between $-30°$ C. and $+150°$ C., normally from $0°$ C. to $50°$ C. such as room temperature. The reaction time may be from 0.1 to 200 hours, normally from 10 to 72 hours such as 24–48 hours. The reaction is generally carried out with slightly more than 2 equivalents of the thiol of the formula VII per equivalent of the O-glycoside of formula VI. It is generally necessary to add a base to the reaction mixture, although the base should not be too strong. Examples of useful bases are cesium carbonate, potassium carbonate, sodium carbonate, sodium hydroxide, potassium hydroxide, as well as pyridine and substituted pyridines. The base should preferably be added after the thiol in order to avoid elimination reactions in the O-glycoside of the formula VI. Protecting groups in the carbohydrate moiety of the O-glycoside of the formula VI may be the ones described in connection with process (a) above. The product compound may be purified and deprotected by the methods described in connection with process (a). The glycoside starting material of formula VI may be prepared as described in process (a).

The oxidation of the resulting thio compounds may occur in two steps, viz. on the one hand through attachment of one oxygen atom on each sulphur atom resulting in the sulphoxides, or through attachment of two oxygen atoms to each atom resulting in the corresponding sulphones. In order to oxidize only to the sulphoxide compounds, two equivalents of oxidizing agents are used. For oxidation to the sulphones, four equivalents or more of oxidizing agent are used. Examples of useful oxidizing agents are peracids, e.g. m-chloroperbenzoic acid; peroxides, e.g. tert.butyl hydroperoxide; aminooxides, gaseous oxygen, or inorganic oxidizing agents such as potassium permanganate, chromium trioxide, etc. The oxidation reaction may be carried out in the same medium as the preceding thio-ether-forming reaction and without purifying or deprotecting the bis-thio compound. The reaction is carried out at a temperature between $-78°$ C. and $+100°$ C., normally from $0°$ C. to $50°$ C. such as room temperature.

A process (c) for preparing compounds in which $R_2$ and $R_3$ together form $=CH_2$, and $R_1$ is $CH_2X$ comprises reacting an O-glycoside of the formula VI defined above with a base. The reaction may be carried out in water or in an protic or protic, polar or non-polar organic solvent such as ethylacetate, methylene chloride, ether or dimethylsulphoxide. The reactions may be carried out at temperatures between $-30°$ C. and $+150°$ C., normally from $0°$ C. $50°$ C. such as room temperature for a period of 0.1–200 hours, normally 8–24 hours such as 16 hours. The carbohydrate moiety of the O-glycoside of the formula VI may be equipped with protecting groups of the type described in process (a). The base may be of the same type as described in process (b), but may, however, also be a stronger base such as sodium hydride or butyllithium. The product formed (having the formula VIII below) may be purified and deprotected by the methods described in the preceding processes.

In a further process (d), compounds are prepared in which $R_2$ and $R_3$ together form $=CH_2$, and $R_1$ is a group of the formula II defined above. The process comprises reacting an O-glycoside of the formula VIII $$\text{(Sugar)}_n\text{-O-CH}_2\text{-}\overset{\overset{\displaystyle CH_2}{\|}}{C}\text{-CH}_2\text{-X} \qquad \text{VIII}$$

with a thiol of the formula VII defined above, and, if desired, reacting the product with an oxidizing agent. The reaction with the thiol may be carried out under the same conditions as those described for the corresponding thio-ether-forming step in process (b), although in the present process the base may be added before the thiol. The oxidation reaction may be carried out using the same oxidation agents described in process (b) and under the same conditions, with the exception that for the preparation of the sulphoxide, only one equivalent of oxidizing agent is used, and for the preparation of sulphones, two or more equivalents of oxidizing agents are used. The products may be purified as described in the previous processes. The glycoside starting material of formula VIII may be prepared as described in process (c) above.

In a further process (e), compounds are prepared in which $R_2$ and $R_3$ together form $=CH_2$ and $R_1$ is a group of the formula III defined above. The process comprises reacting an O-glycoside of the formula VIII defined above with an alcohol $R_6$—OH wherein $R_6$ is as defined above. The reaction may be carried out under conditions similar to those described for the thio-ether-forming step in process (b) above.

In a further process (f), compounds are prepared in which $R_2$ and $R_3$ together form $=CH_2$ and $R_1$ is of the formula IIIa defined above. The process comprises reacting an O-glycoside of the formula VIII defined above with an amine $R_7R'_7NH$, wherein $R_7$ and $R'_7$ are as defined above. The reaction conditions may be similar to those described in the thio-ether-forming step in process (b) above.

A process (g) for preparing the polymers of the formula XX is contemplated. The process comprises reacting an O-glycoside of the formula VI defined above with a dithiol HS—$R_4$—SH wherein $R_4$ is as defined above. The reaction conditions are similar to those described in the thio-ether-forming step in process (b).

Another process (h) for preparation of the polymers of the formula XXI is also contemplated. The process comprises reacting an O-glycoside of the formula VI defined above with a trithiol of the formula $$\overset{\displaystyle SH}{\underset{}{\text{HS-}R_4\text{-SH}}}$$

wherein $R_4$ is as defined above. As in process (g), the reaction conditions may be similar to those described in the thio-ether-forming step in process (b) above.

In yet another process (i), compounds of the formula I may be prepared by reacting a compound of the formula Ia $$\text{(Sugar)}_r\text{-O-CH}_2\text{-}\overset{\overset{\displaystyle R_2}{|}}{\underset{\underset{\displaystyle R_1}{|}}{C}}\text{-}R_3 \qquad \text{Ia}$$

wherein Sugar, $R_1$, $R_2$ and $R_3$ are as defined above, and r is an integer from 1 to 9 inclusive, with a sugar derivative of the formula Va $$\text{(Sugar)}_{n-r}\text{-Y} \qquad \text{Va}$$

wherein Sugar, Y, n and r are as defined above. The Sugar moiety of the compound of formula Ia is preferably suitably protected, and it is particularly preferred that there is only one unprotected hydroxy group. The reaction may be carried out on conditions similar to those described in process (a) using Lewis acid or metal salt catalysts. By this process, the Sugar moiety of an already prepared O-glycoside of formula I may be modified or converted to obtain a different O-glycoside of the formula I.

In yet another process (j), compounds of the formula I in which $R_3$ is H and $R_1$ and $R_2$ are not —$CH_2X$ may be prepared by reacting a compound of the formula V as defined above with an alcohol of the formula X $$\text{HO-CH}_2\text{-}\overset{\overset{\displaystyle R'}{|}}{\underset{\underset{\displaystyle R''}{|}}{CH}} \qquad \text{X}$$

wherein R' and R'' which may be the same or different have the same meaning as $R_1$ and $R_2$ above except that R' and R'' are not —$CH_2X$. The reaction conditions may be similar to those described in process (a) above.

The compounds of formula I may be used as synthetic receptors for a wide variety of biological entities. The receptor-specific unit of natural receptors is generally a carbohydrate unit although parts of the "spacer-arm" carrying the carbohydrate unit may also form part of the receptor by providing a specific environment and/or overall spatial shape to the receptor unit. In general, in the compounds of the formula I, the carbohydrate moiety is selected according to what type of agent (e.g. microorganism, virus, blood protein, antibody, etc.) for which a receptor is desired. The aglycon moiety of the compound of the formula I will generally determine the physical manner in which the receptor is used. Thus, the aglycon moiety may be a lipid function (with either one or two lipophilic "tails") making it possible to incorporate the compounds into a biological membrane or through a micelle. As a result of the structure of the part of the aglycon moiety close to the carbohydrate unit, the compounds of the formula I are able to mimic natural receptors. This similarity in structure will be evident when comparing the structure of the synthetic glycolipids shown below with the structure of the natural glycolipids shown previously.

A further advantage with the compounds of formula I, wherein $R_3=H$, $R_1=$ —$CH_2$—$S(O)_m(O)_p$—$R_4R_5$ with $R_4=$alkyl chain and $R_5=$COOH and $R_2=$ —$CH_2$—$S(O)_m(O)_p$—$R_4R_5$ with $R_4=$alkyl chain and $R_5=CH_3$ or COOH, is that these compounds are water soluble while at the same time they are "mimics" of natural glycolipids. This is a new physical property of compounds that perform in a way that is similar to natural glycolipids with regard to receptor activity towards e.g. viruses (see below).

Allyl-thio compounds have the advantage of being easily hydrogenated (c.f. A. S. Birch and K. A. M. Walker, Tetrahedron Lett. (1967) p. (1935). This can be applied to the allyl-thio glycosides of the present invention for radioactive labelling with catalytic tritiation.

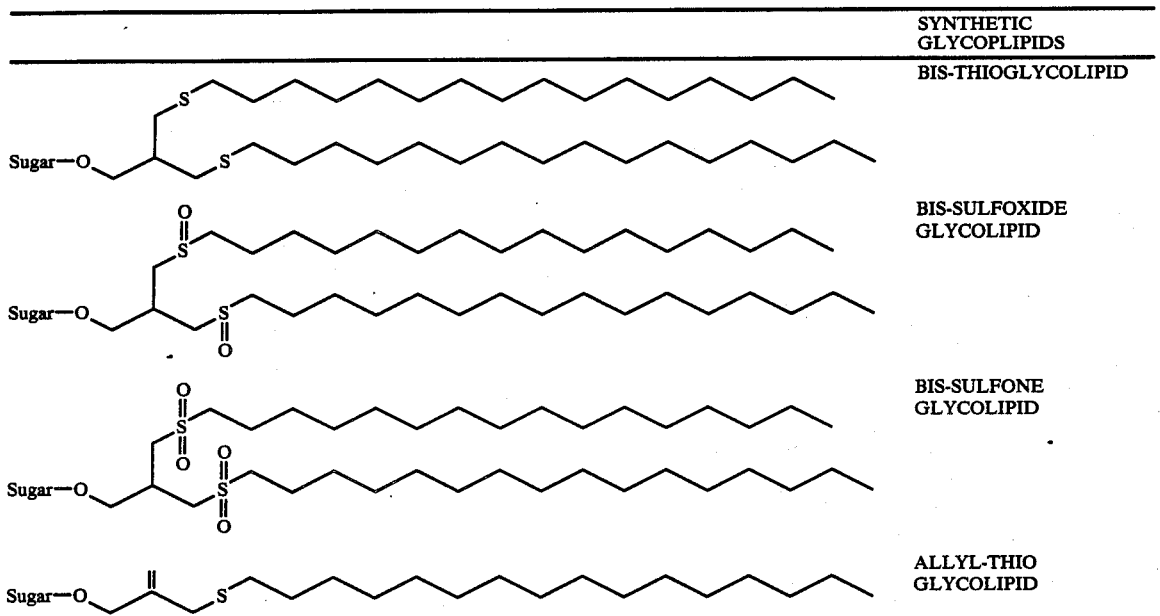

Through the use of sulfoxide or sulfone groups in the molecule, it is possible to "fine-tune" the hydrophilic/-hydrophobic and polar/apolar properties of the aglycon moiety which may be of importance e.g. when attempts are made to mimic natural receptors in which part of the aglycon moiety also defines the receptor such as in the secondary penetration-receptor in certain vira.

The aglycon moiety may also be a "spacer-arm" attached to a carrier of the types suggested above; or the aglycon part may be a unit with a reactive terminal making it possible to incorporate any specific receptor into e.g. a carrier structure of some kind. The activation of the reactive terminal could conceivably be carried out before as well as after the receptor has attached itself to the agent, to which it has been designed. A central feature of the present invention is the possibility of easily incorporating receptors specific for a wide variety of biological agents into a desired structure. The possibilities opened through the invention are multifarious. The compounds of the formula I may form part of or be incorporated in products like pharmaceutical compositions for therapeutic or prophylactic treatment of bacterial or viral diseases (e.g. injectables comprising micelles, liposomes or microscopic beads, implants, tablets, lozenges, or chewing tablets for oral prophylactic use, etc.); diagnostic tools such as in RIA- and ELISA-methods, diagnostic dip-sticks, agglutination kits, immunological test cards or blood test cards (through incorporation of the compounds of formula I on appropriate carrier materials such as plastics); disinfection means such as fluids (for cleaning e.g. surgical wounds) or paper tissues incorporating specific receptors towards certain biological agents (e.g. vira such as common cold, herpes, and other vira, bacteria transmitting various infectious diseases, etc.).

With respect to treatment or prophylaxis against viral or bacterial infectious diseases, one important use aspect is in connection with epithelial cells and at the port-of-entry of various infections. Examples of such port-of-entries are the mucos membranes of the eye, nose, oral cavity, throat, respiratory tract, gastro-intestinal tract, urinary tract and reproductive organs. Treatment or prophylaxis may be obtained by direct application on the mucous membranes of the compounds of the formula I in a pharmaceutically acceptable form such as a suspension, an aerosole, an ointment or a solution. On the mucous membranes, the active compounds will bind to bacteria or, in particular, vira thereby reducing the infecting ability of the organisms in question.

The compounds of the formula I may, however, also be used as systemic agents for intravenous, intramuscular, intraperitoneal or subcutaneous injection. The composition for this use may be in the form of a solution, an emulsion or a suspension of either compounds in a solid form or the compounds incorporated on various of the carriers described above. The compounds of the formula I may furthermore be administered in the form of nasal or oral sprays.

Other uses of the compounds of the formula I include flushing of the urinary tract, intestines, etc.

Another interesting use of the compounds of the formula I is as vaccines. If the carbohydrate moiety is of a type occurring in bacteria and/or vira, such compounds of the formula I may act as antigenes promoting the formation of antibodies in the host animal, e.g. a human. The ability to promote the formation of antibodies may, however, also be exploited in vitro for the production of monoclonal antibodies in cell cultures.

Since the receptor-specific binding between spermatozoa and ova is also based on carbohydrates, the compounds of the formula I may conceivably also be used as a contraceptive agent incorporated in e.g. an intravaginal device such as a sponge or a tampon.

In view of the above, the present invention also relates to pharmaceutical or diagnostic compositions comprising one or more compounds of the formula I, optionally in combination with a pharmaceutically acceptable excipient.

The pharmaceutical composition may be in the form of tablets, capsules, lozenges, sirups, injectable solutions, injectable emulsions, implants, or suppositories.

The excipient may be any of the excipients commonly used within the art. For solid compositions may be used conventional non-toxic solid excipients including e.g. pharmaceutical grades of mannitol, lactose, starch, magnesium stearate, sodium saccharin, talc, cellulose, saccharose, magnesium carbonate or the like. Liquid pharmaceutically administrable compositions may e.g. be prepared by dissolving, dispersing etc. the active compound and an optional pharmaceutical adjuvant in an excipient such as water, salt water, aqueous dextrose, glycerol, ethanol, etc. in order to form a solution or suspension. If desired, the pharmaceutical composition to be administered may also contain minor amounts of non-toxic additives such as wetting or emulsifying agents, pH-buffers etc., e.g. sodium acetate, sorbitan monolaurate, triethanol amine, etc. The active compound may also be formulated as suppositories, using e.g. polyalkylene glycols such as propylene glycol as an excipient. The actual preparation of such dosage forms are well known or will be evident to persons skilled in the art, cf. e.g. Remingtons Pharmaceutical Sciences, Mack Publishing Company, Easton, Pa., 15th Edition, 1975.

For intravenous injections, the compound (optionally bound to a carrier) is dissolved in an aqueous medium buffered to the desired pH and treated in order to control isotonicity.

Since the compounds of the formula I are useful in connection with the mucos membranes, the compounds may also be administered in the form of an aerosol.

When administered as an aerosol, the active compound is preferably given in a finely divided form together with a surfactant and a propellant.

The dosages in which the compounds of the formula I are administered may vary widely depending on the intended use, whether for prophylaxis, including disinfection, or therapy, the type of infection to be combated, the age and condition of the patient, etc., but is expected to be at a milligram level. For rotavirus infection (diarrhoea), a daily dose of 1 µg receptor per human individual has been calculated to agglutinate/inactivate all viruses produced during one day, provided the receptor is bivalent and only one bivalent receptor is used per virus particle. In practice, of course, a far larger dosage is needed to secure an effective binding of all the virus particles present. Contrary to what is the case with most medicaments now in use, the dosage level may not be so essential since the toxic effects of the compounds of formula I are expected to be negligible since, in fact, at least the natural receptors are substances which are present in large amounts in the human or animal system.

Cerain compounds of the formula I such as bis-sulfide glycolipids, i.e. compounds of the formula I in which $R_3$ is H, and $R_1$ and $R_2$ are groups of the formula II wherein m and p both are 0, $R_4$ is an alkyl chain, and $R_5$ is H, have been found to exhibit remarkable properties in that they are able to form liquid crystals in aprotic media such as dimethyl sulphoxide (cf. Example 7). It is contemplated that other similar subgroups of compounds of the formula I have the same properties. To the best of Applicant's knowledge, this is the first time that liquid crystals have been prepared in an aprotic medium, and this particular property may render possible the formation of liquid crystals with higher stability in electrical fields. Such liquid crystals may conceivably be used in e.g. visual displays with lifetimes superior to those possible at the present time.

The invention is further illustrated by the following non-limiting preparation and examples. Preparation 1 describes the preparation of the starting material DlBol, which has been subject to a separate patent application, submitted at the same data as the present application.

PREPARATION 1

3-Bromo-2-bromomethylpropan-1-ol (DlBol)

3-Bromo-2-bromomethylpropanoic acid (15.3 g; 62 mmol) (cf. A. F. Ferris, J. Org. Chem., 20 (1955) p 780) was dissolved in dry dichloromethane (400 ml) and cooled (0°). The reaction mixture was kept under nitrogen. A solution of diborane in tetrahydrofuran (190 ml; 190 mmol; 1M solution of $BH_3$ in THF) was added dropwise with stirring. After 1 hour, the cooling bath was removed and the mixture was left overnight at room temperature. Hydrochloric acid (210 ml; 1M) was added, the organic phase was separated and the aqueous phase was extracted with dichloromethane (3×50 ml). The combined organic phases were dried ($Na_2SO_4$) and concentrated. Flash chromatography of the residue gave pure DlBol (13.8 g; 96%). Bp ca. 45° C. (0.1 mm Hg); $n_D^{23}$ 1.5439;

IR-spectrum: $\nu_{max}$=3340 $cm^1$ $^1$H-NMR ($CDCl_3$, $Me_4Si$) δ(ppm)=3.79 (d, 2 H, J=6.0 Hz, $CH_2$—O), 3.59 (d, 4 H, J=5.7 Hz, $CH_2Br$), 2.27 (heptet, 1 H, J=6 Hz, $CH(CH_2)_3$;

$^{13}$C-NMR ($CDCl_3$, $Me_4Si$): δ(ppm)=62.4 ($CH_2OH$), 44.4 (CH), 32.8 ($CH_2Br$);

Analysis calculated for $C_4H_8Br_2O$ C 20.7, H 3.48
Found: C 21.0, H 3.73

EXAMPLE 1

Preparation of DIB glycosides (a) Borontrifluoride etherate (0.7 ml) was added dropwise with stirring to a solution of a fully acetylated sugar (1 mmol) and DlBol (232 mg; 1 mmol) in dichloromethane (3 ml) at room temperature. After 2–4 h, the mixture was washed with water and sodium hydrogencarbonate solution, dried ($Na_2SO_4$), and concentrated. The residue was subjected to chromatography ($SiO_2$, ethyl acetate: hexane) to give the DIB glycoside in pure form (see Table 1). The following compounds were prepared: 3-Bromo-2-bromomethylprop-1-yl 2,3,4,6-tetra-O-acetyl-β-D-glucopyranoside (DIB-1). From 1,2,3,4,6-penta-O-acetyl-β-D-glucopyranose. Yield: 54%. $[\alpha]_D^{23}=-5°$ (c=0.6 in $CDCl_3$).

NMR-Spectrum ($CDCl_3$, TMS): δ(ppm)=5.22 (t, 1H, $J_{2,3}=J_{3,4}$=9.7 Hz, H-3), 5.1 (t, 1H, $J_{4,5}$=9.4 Hz, H-4), 4.99 (t, 1H, H-2), 4.51 (d, 1H, $J_{1,2}$=7.9 Hz, H-1), 4.27, 4.15 (ABq with further coupling, each 1H, $J_{AB}$=12.6 Hz, $J_{5,6}$=4.0 Hz, H-6,6'), 3.71 (m, 1H, H-5), 2.34 (m, 1 H, $CH(CH_2)_3$).

Analysis: Calculated for $C_{18}H_{26}Br_2O_{10}$: C 38.5, H 4.66
Found: C 38.4, H 4.69

3-Bromo-2-bromomethylprop-1-yl 2,3,4,6-tetra-O-acetyl-β-D-galactopyranoside (DIB-2). From 1,2,3,4,6-penta-O-acetyl-β-D-galactopyranose. Yield: 50%. $[\alpha]_D^{23}=+1°$ (c=0.7 in $CDCl_3$). NMR-Spectrum ($CDCl_3$, TMS): δ(ppm)=5.40 (d, 1H, $j_{3,4}$=3.2 Hz, H-4), 5.19 (dd, 1H, $J_{2,3}$=10.4 Hz, H-2), 5.03 (dd, 1H, H-3), 4.47 (d, 1H, $J_{1,2}$=7.6 Hz, H-1), 4.19, 4.13 (ABq with further coupling, each 1H, $J_{AB}$=11.2 Hz, $J_{5,6}=J_{5,6}$=6.5 Hz, H-6,6'), 3.92 (t, 1H, $J_{4,5}$=0.4 Hz, H-5), 2.35 (septet, 1H, J=5.8 Hz, $CH(CH_2)_3$).

Methyl (3-bromo-2-bromomethylprop-1-yl 2,3,4-tri-O-acetyl-β-D-glucopyranosid)uronate (DIB-3). From methyl (1,2,3,4-tetra-O-acetyl-β-D-glucopyranose)uronate. Yield: 26%. $[\alpha]_D^{23} = +3°$ (c=1.1 in CDCl$_3$). NMR-Spectrum (CDCl$_3$, TMS): δ(ppm)=5.33–5.16 (m, 2H, H-3,4), 5.01 (m, 1H, H-2), 4.55 (d, 1H, $J_{1,2}$=7.6 Hz, H-1), 4.04 (d, 1H, $J_{4,5}$=9.4 Hz, H-5), 3.77 (s, 3H, OCH$_3$), 2.34 (septet, 1H, J=6.1 Hz, CH(CH$_2$)$_3$).

3-Bromo-2-bromomethylprop-1-yl-3,4,6-tri-O-acetyl-2deoxy-2-phthalimido-β-D-glucopyranoside (DIB-4). From 1,3,4,6-tetra-O-acetyl-2-deoxy-2-phthalimido-α/β-D-glucopyranose (α/β ratio 1/1). Yield: 52%. $[\alpha]_D^{23}=20°$ (c=1.0 in CDCl$_3$). NMR-Spectrum (CDCl$_3$, TMS): δ(ppm)=5.82 (t, 1H, $J_{3,4}$=10.1 Hz, H-3), 5.36 (d, 1H, $J_{1,2}$=8.3 Hz, H-1), 5.17 (t, 1H, $J_{4,5}$=10,1 Hz, H-4), 4.32 (dd, 1H, $J_{2,3}$=10.4 Hz, H-2), 4.33, 4.19 (ABq with further coupling, each 1H, $J_{AB}$=12.2 Hz, $J_{5,6}$=5.0 Hz, $J_{5,6}$=2.2 Hz, H-6,6'), 3.89 (m, 1H, H-5), 2.24 (m, 1H, J=5.8 Hz, CH(CH$_2$)$_3$).

3-Bromo-2-bromomethylprop-1yl 2,3,4-tri-O-acetyl-β-D-xylopyranoside (DIB-5). From 1,2,3,4-tetra-O-acetyl-α/β-D-xylopyranose (α/β ratio 1/1). Yield: 50% $[\alpha]_D^{23}=-25°$ (c=0.9 in CDCl$_3$). NMR-Spectrum (CDCl$_3$, TMS): δ(ppm)=5.18 (t, 1H, $J_{2,3}$=$J_{3,4}$=8.3 Hz, H-3), 4.98–4.89 (m, 2H, H-2,4), 4.49 (d, 1H, $J_{1,2}$=6.7 Hz, H-1), 4.14, 3.39 (ABq with further coupling, $J_{AB}$=11.5 Hz, $J_{4,5}$=5.0 Hz. $J_{4,5'}$=9.0 Hz, H-5,5'), 2.34 (septet, J=5.6 Hz, CH(CH$_2$)$_3$).

3-Bromo-2-bromomethylprop-1-yl 2,3,6-tri-O-acetyl-4,0-(2,3,4,6-tetra-O-acetyl-β-D-galactopyranosyl)-β-D-glucopyranoside (DIB-6). From 1,2,3,6-tetra-O-acetyl-4-O-(2,3,4,6-tetra-O-acetyl-β-D-galactopyranosyl)-β-D-glucopyranose. Yield: 60%; $[\alpha]_D^{23}=-6°$ (c=0.7 in CDCl$_3$). NMR-Spectrum (CDCl$_3$, TMS): δ(ppm)=5.35 (d, 1H, $J_{3',4'}$=2.9 Hz, H-4'), 5.20 (t, 1H, $J_{2,3}$=9.0 Hz, H-2), 5.11 (dd, 1H, $J_{1',2'}$=7.9 Hz, $J_{2',3'}$=10.1 Hz, H-2'), 4.95 (dd, 1H, H-3'), 4.89 (t, 1H, $J_{3,4}$=9.0 Hz, H-3), 4.50, 4.47 (two d, each 1H, J=7.9 Hz, H-1,1'), 2.23 (septet, 1H, J=5.8 Hz, CH(CH$_2$)$_3$).

Analysis: Calculated for: C$_{30}$H$_{42}$Br$_2$O$_{18}$: C 42.4 H 4.98 Found: C 42.4 H 4.92

3-Bromo-2-bromomethylprop-1-yl 2,3,6-tri-O-acetyl-4-O-(2,3,4,6-tetra-O-acetyl-α-D-galactopyranosyl)-β-D-galactopyranoside (DIB-7). From 1,2,3,6-tetra-O-acetyl-4-O-(2,3,4,6-tetra-O-acetyl-α-D-galactopyranosyl)-α-D-galactopyranose. Yield: 43%. $[\alpha]_D^{23}=+68.6°$ (c=1.5 in CDCl$_3$). NMR-Spectrum (CDCl$_3$, TMS): δ(ppm)=5.58 (dd, 1H, $J_{4',5'}$=1.0 Hz, H-4'), 5.39 (dd, 1H, $J_{2',3'}$=10.8 Hz, H-2'), 5.20 (dd, 1H, $J_{3',4'}$=3.6 Hz, H-3'), 5.17 (dd, 1H, $J_{2,3}$=10.8 Hz, H-2), 5.01 (d, 1H, $J_{1',2}$=3.2 Hz, H-1'), 4.82 (dd, 1H, $J_{2,4}$=2.9 hz, H-3), 4.47 (d, 1H, $J_{1,2}$=7.6 Hz, H-1), 2.37 (septet, 1H, J=5.8 Hz, CH(CH$_2$)$_3$).

(b) Acetobromolactose (3.15 g; 4.51 mmol) and silver trifluoromethansulfonate (1.93 g; 7.5 mmol) were dried in a two-compartment reaction vessel as described by Nashed & Andersson (1982). DlBol (1.25 g; 5.39 mmol) in dichloromethane (10 ml) and tetramethylurea (1.3 g; 11.3 mmol) in dichloromethane (10 ml) were added and the reaction mixture was stirred overnight. The reaction vessel was protected from light by means of aluminum foil. When the acetobromolactose had been consumed, the reaction mixture was filtered through Celite, concentrated and chromatographed to give the DIB β-lactoside (DIB-6, 2.7 g; 73%); see above and Table 1.

Using the same procedure as above but with 2,3,6-tri-O-acetyl-4-O-(2,3,4,6-tetra-O-acetyl-α-D-galactopyranosyl)-α-D-galacto-pyranosyl bromide (2.65 g, 3.80 mmol) (cf. Dahmen et al. Carbohydr. Res., 116 (1983)) and acetylation of the crude reaction mixture, permitted the isolation of DIB-7 (1.88 g, 39%) and the corresponding α-glycoside (0.24 g, 7%).

(c) DIB 2,3,4,6-tetra-O-acetyl-β-D-glucopyranoside (562 mg; 1 mmol) may be deacetylated as described in Example 2 to give DIB β-D-glucopyranoside which is transformed into DIB 4,6-benzylidene-β-D-glucopyranoside by treatment with dimethoxytoluene under acidic conditions. Treatment with benzyl chloride and sodium hydride in dimethylformamide gives DIB 2,3-di-O-benzyl-4,6-benzylidene-β-D-glucopyranoside which in turn is reduced with sodium cyanoborohydride in ether (cf. Nashed & Andersson (1982) to give 2,3,6-tri-O-benzyl-β-D-gluco pyranoside. Reaction with acetobromogalactose and silver trifluoromethane sulfonate (AgTf), essentially as under (b) above, gives the expected DIB lactoside, which is hydrogenated to cleave off the benzyl groups. Acetylation in the normal way, followed by chromatography, gives the pure DIB lactoside (DIB-6) as shown in Table 1.

TABLE 1

| Compound no. | R'$_1$ | R'$_2$ | R'$_3$ | R'$_4$ | R'$_5$ | R'$_6$ |
|---|---|---|---|---|---|---|
| DIB-1 | DAc[a] | H | OAc | OAc | H | CH$_2$OAc |
| DIB-2 | OAc | H | OAc | H | OAc | CH$_2$OAc |
| DIB-3 | OAc | H | OAc | OAc | H | COOCH$_3$ |
| DIB-4 | NPhth[b] | H | OAc | OAc | H | CH$_2$OAc |
| DIB-5 | OAc | H | OAc | OAc | H | H |
| DIB-6 | OAc | H | OAc | GalAcβ[c] | H | CH$_2$OAc |
| DIB-7 | OAc | H | OAc | H | GalAcα[d] | CH$_2$OAc |

[a] Ac = acetyl;
[b] Phth = phthaloyl;
[c] GalAcβ = 2,3,4,6-tetra-O—acetyl-β-D—galactopyranosyl;
[d] GalAcα = 2,3,4,6-tetra-O—acetyl-α-D—galactopyranosyl.

EXAMPLE 2

Preparation of bis-sulfide glycosides

A fully acetylated DIB glycoside (0.38 mmol), an alkyl thiol (1 mmol), cesium carbonate (338 mg; 1 mmol) and dimethylformamide (2 ml) were stirred at room temperature under nitrogen for 24–48 hours. The reaction was monitored by TLC (SiO$_2$, ethyl acetate: hexane). Dichloromethane (40 ml) was added and the mixture was washed with water (2×5 ml), dried (Na$_2$SO$_4$) and concentrated. Column chromatography (SiO$_2$, ethyl acetate: hexane) gave the pure, fully acetylated glycoside (see Table 2).

The acetylated glycoside (0.2 mmol) was dissolved in dichloromethane (15 ml) and methanolic sodium methoxide (10 ml; prepared by dissolving ca. 1 mg of sodium in methanol) was added. The reaction was monitored by TLC (chloroform:methanol:water, 65:35:10). In some cases, a precipitate was formed towards the end of the reaction. One drop of acetic acid was added and the reaction mixture was concentrated, suspended in water (10 ml) and freeze-dried to give a qunatitative yield of the unprotected glycolipid, contaminated with small amounts of sodium acetate (ca. 1% w/w). The following compounds were prepared:

3-Hexadecylthio-2-hexadecylthiomethylprop-1-yl 2,3,4,6-tetra-O-acetyl-β-D-glycopyranoside (RSC16-1). From DIB-1 and hexadecanethiol. Yield: 70%. $[\alpha]_D^{23} = -1.6°$ (c=1.1 in CDCl$_3$). NMR-Spectrum (CDCl$_3$, TMS): δ (ppm)=5.20 (t, 1H, $J_{2,3}$=9.3 Hz, H-3), 5.06 (t, 1H, $J_{3,4}$=$J_{4,5}$=9.5 Hz, H-4), 4.98 (dd, 1H, H-2), 4.48 (d, 1 H, $J_{1,2}$=7.9 Hz, H-1), 4.26, 4.11 (ABq with further coupling, each 1 H, $J_{AB}$=12.4 Hz, $J_{5,6}$=4.8 Hz, $J_{5,6'}$=2.5 Hz, H-6,6'), 2.6-2.4 (m, 8 H, CH$_2$-S).

Analysis: Calculated for C$_{50}$H$_{92}$O$_{10}$S$_2$: C 65.5 H 10.1 Found: C 65.7 H 10.2

3-Hexadecylthio-2-hexadecylthiomethylprop-1-yl 2,3,4,6-tetra-O-acetyl-β-D-galactopyranoside (RSC16-2). From DIB-2 and hexadecanethiol. Yield: 79%. $[\alpha]_D^{23} = +1°$ (c=1.6 in CDCl$_3$). NMR-Spectrum (CDCl$_3$, TMS): δ (ppm)=5.37 (dd, 1 H, $J_{4,5}$=0.8 Hz, H-4), 5.17 (dd, 1 H, $J_{2,3}$=10.3 Hz, H-2), 4.99 (dd, 1 H, $J_{3,4}$=3.4 Hz, H-3), 4.44 (d, 1H, $J_{1,2}$=7.8 Hz, H-1), 2.7-2.4 (m, 8 H, CH$_2$-S).

Analysis: Calculated for C$_{50}$H$_{92}$O$_{10}$S$_2$: C 65.5 H 10.1 Found: C 65.3 H 10.2

Methyl (3-hexadecylthio-2-hexadecylthiomethylprop-1-yl 2,3,4-tri-O-acetyl-β-D-glucopyranosyl)-uronate (RSC16-3). From DIB-3 and hexadecanethiol. Yield: 68%. $[\alpha]_D^{23} = 1.7°$ (c=0.9 in CDCl$_3$. NMR-Spectrum (CDCl$_3$, TMS): δ (ppm)=5.25 (t, 1 H, $J_{3,4}$=9.0 Hz, H-3), 5.20 (t, 1 H, $J_{4,5}$=9.4 Hz, H-4), 5.01 (dd, 1 H, $J_{2,3}$=9.0 Hz, H-2), 4.54 (d, 1 H, $J_{1,2}$=7.6 Hz, H-1), 4.03 (d, 1 H, H-5), 3.76 (s, 3 H, O-CH$_3$), 2.60-2.45 (m, 8 H, CH$_2$-S).

Analysis: Calculated for C$_{49}$H$_{90}$O$_{10}$S$_2$: C 64.7 H 10.2 Found: C 64.9 H 10.2

3-Hexadecylthio-2-hexadecylthiomethylprop-1-yl 3,4,6-tri-O-acetyl-2-deoxy-2-phthalimido-β-D-glucopyranoside (RSC16-4). From DIB-4 and hexadecanethiol. Yield: 81%. $[\alpha]_D^{23} = +11.6°$ (c=1.1 in CDCl$_3$). NMR-Spectrum (CDCl$_3$, TMS): δ (ppm)=5.80 (dd, $J_{2,3}$=10.7 Hz, H-3), 5.32 (d, 1 H, $J_{1,2}$=8.5 Hz, H-1), 5.16 (t, 1 H, $J_{3,4}$=$J_{4,5}$=9.2 Hz, H-4), 2.5-2.2 (m, 8 H, CH$_2$-S).

Analysis: Calculated for C$_{55}$H$_{93}$NO$_{10}$S$_2$: C 67.0 H 9.33 N 1.39 Found: C 67.0 H 9.52 N 1.39

3-Hexadecylthio-2-hexadecylthiomethylprop-1-yl 2,3,4-tri-O-acetyl-β-D-xylopyranoside (RSC16-5). From DIB-5 and hexadecanethiol. Yield: 61%. $[\alpha]_D^{23} = -17.6°$ (c=1.1 in CDCl$_3$).

NMR-Spectrum (CDCl$_3$, TMS): δ (ppm)=5.15 (t, 1 H, $J_{2,3}$=$J_{3,4}$=8.5 Hz, H-3), 4.98-4.85 (m, 2 H, H-2,4), 4.45 (d, 1 H, $J_{1,2}$=6.7 Hz, H-1), 4.10, 3.34 (ABq with further coupling, each 1 H, $J_{AB}$=12.0 Hz, $J_{45}$=5.0 Hz, $J_{4,5'}$=8.8 Hz, H-5,5'), 2.7-2.4 (m, 8 H, CH$_2$-S).

Analysis: Calculated for C$_{47}$H$_{88}$OHD 8S$_2$: C 66.8 H 10.5 Found: C 66.7 H 10.6

3-Hexadecylthio-2-hexadecylthiomethylprop-1-yl 2,3,6-tri-O-acetyl-4-O-(2,3,4,6-tetra-O-acetyl-β-D-galactopyranosyl)-β-D-glucopyranoside (RSC16-6). From DIB-6 and hexadecanethiol. Yield 88%. $[\alpha]_D^{23} = -4.1°$ (c=0.8 in CDCl$_3$).

NMR-Spectrum (CDCl$_3$, TMS): δ (ppm)=5.34 (d, 1 H, H-4'), 5.19 (t, 1 H, $J_{2,3}$=9.0 Hz, H-2), 5.10 (dd, 1H, $J_{2',3'}$=10.4 Hz, H-2'), 4.95 (dd, 1H, $J_{3',4'}$=3.6 Hz, H-3'), 4.89 (dd, 1 H, $J_{3,4}$=7.9 Hz, H-3), 4.47 4.46 (two d, each 1 H, J=7.6 Hz and 7.9 Hz, H-1,1'), 2.6-2.45 (m, 8 H, S-CH$_2$).

Analysis: Calculated for C$_{26}$H$_{108}$O$_{18}$S$_2$: C 61.8 H 9.03 Found: C 62.0 H 9.32

3-Hexadecylthio-2-hexadecylthiomethylprop-1-yl 2,3,6-tri-O-acetyl-4-O-(2,3,4,6-tetra-O-acetyl-α-D-galactopyranosyl)-β-D-galactopyranoside (RSC16-7). From DIB-7 and hexadecanethiol. Yield: 51%. $[\alpha]_D^{23} = +52°$ (c=0.6 in CDCl$_3$).

NMR-Spectrum (CDCl$_3$, TMS): δ (ppm)=5.57 (dd, 1 H, $J_{4',5'}$=0.8 Hz, H-4'), 5.38 (dd, 1 H, $J_{2',3'}$=11.0 Hz, H-2'), 5.18 (dd, 1 H, $J_{3',4'}$=3.7 Hz, H-3'), 5.16 (dd, 1 H, $J_{2,3}$=11.0 Hz, H-2), 4.99 (d, 1H, $J_{1',2'}$=3.3 Hz, H-1'), 4.79 (dd, 1 H, $J_{3,4}$=2.8 Hz, H-3), 4.44 (d, 1 H, $J_{1,2}$=7.7 Hz, H-1), 2.7-2.45 (m, 8 H, S-CH$_2$).

Analysis: Calculated for C$_{62}$H$_{108}$O$_{18}$S$_2$: C 61.8 H 9.03 Found C 60.7 H 9.00

3-Octadecylthio-2-octadecylthiomethylprop-1-yl 2,3,6-tri-O-acetyl-4-O-(2,3,4,6-tetra-O-acetyl-β-D-galactopyranosyl)-β-D-glucopyranoside (RSC18-1). From DIB-6 and octadecanethiol. Yield: 67%. $[\alpha]_D^{23} = -3.4°$ (c=0.8 in CDCl$_3$). NMR-Spectrum (CDCl$_3$, TMS): practically identical with the spectra of RSC16-6 and RSC8-1.

3-Octylthio-2-octylthiomethylprop-1-yl 2,3,6-tri-O-acetyl-4-O-(2,3,4,-6-tetra-O-acetyl-β-D-galactopyranosyl)-β-D-glucopyranoside (RSC8-1). From DIB-6 and octanethiol. Yield: 73%. $[\alpha]_D^{23} = -4.9°$ (c=0.8 in CDCl$_3$). NMR-Spectrum (CDCl$_3$, TMS): practically identical with the spectra of RSC16-6 and RSC18-1.

3-Hexadecylthio-2-hexadecylthiomethylprop-1-yl β-D-glucopyranoside (RSC16-8). From RSC16-1. $[\alpha]_D^{23} = -7°$ (c=0.9 in CMD(CDCl$_3$/-CD$_3$OD/-D$_2$O, 65:35:10). NMR-Spectrum (CMD, TMS, 50°): δ (ppm)=4.29 (d, 1 H, $J_{1,2}$=7.6 Hz, H-1), 2.70 (d, 4 H, J=6.4 Hz, CH—(CH$_2$—S)$_2$), 2.53 (t, 4 H, J=7.3 Hz, S—CH$_2$—CH$_2$).

3-Hexadecylthio-2-hexadecylthiomethylprop-1-yl β-D-galactopyranoside (RSC16-9). From RSC16-2. $[\alpha]_D^{23} = -3°$ (c=0.5 in CMD). NMR-Sepctrum (CMD, TMS, 20°): δ (ppm)=4.24 (virtual coupling, $J_{1,2}$=7.6 Hz, H-1), 2.71 (d, 4 H, J=6.7 Hz, CH—(CH$_2$—S)$_2$), 2.53 (t, 4H, J=7.2 Hz, S—CH$_2$—CH$_2$).

3-Hexadecylthio-2-hexadecylthiomethylprop-1-yl β-D-xylopyranoside (RSC16-12). From RSC16-5. $[\alpha]_D^{23} = -6°$ (c=0.5 in CMD). NMR-Spectrum (CMD, TMS, 50°): δ (ppm)=4.25 (d, 1 H, J=7.1 Hz, H-1), 2.69 (d, 4 H, J=6.4 Hz, CH—(CH$_2$—S)$_2$), 2.53 (t, 4 H, J=7.5 Hz, S—CH$_2$—CH$_2$).

3-Hexadecylthio-2-hexadecylthiomethylprop-1-yl 4-O-β-D-galactopyranosyl-β-D-glucopyranoside (RSC16-13). From RSC16-6. $[\alpha]_D^{23} = -3.5°$ (c=1.6 in CMD). NMR-Spectrum (CMD, TMS, 40°): δ (ppm)=4.31 (d, 2 H, J=7.8 Hz, H-1,1'), 2.71 (d, 4 H, J=6.6 Hz, CH—CH$_2$—5), 2.53 (t, 4 H, J=7.3 Hz, S—CH$_2$—CH$_2$).

3-Hexadecylthio-2-hexadecylthiomethylprop-1-yl 4-O-α-D-galactopyranosyl-β-D-galactopyranoside (RSC16-14). From RSC16-7. $[\alpha]_D^{23} = +28°$ (c=0.6 in CMD). NMR-Spectrum (CMD, TMS, 50°): δ (ppm)=5.01 (d, 1 H, $J_{1',2'}$=2.5 Hz, H-1'), 4.27 (d, 1 H, $J_{1,2}$=7.2 Hz, H-1), 2.72 (d, 4 H, J=6.3 Hz, CH—(CH$_2$—S)$_2$), 2.53 (t, 4 H, J=7.4 Hz, S—CH$_2$—CH$_2$).

3-(10-Methoxycarbonyldecylthio)-2-(octylthiomethyl)-prop-1-yl 2,3,6-tri-O-acetyl-4-O-acetyl-4-O-(2,3,4,6-tetra-O-acetyl-β-D-galactopyranosyl)-β-D-glucopyranoside (RSC10EC8).

DIB-6 (291 mg, 0.34 mmol was dissolved in dry dimethylformamid (1 ml). Octylthiol (50 mg, 0.34 mmol) in dimethylformamid (1 ml) was added, followed by cesium carbonate (112 mg), 0.34 mmol). After stirring for 70 h at 20°, water (15 ml) was added and the mixture was extracted with dichloromethane (2×10 ml). The extract was dried (Na$_2$SO$_4$) and concentrated by several additions of toluene to remove remaining dimethylformamide. The residue was submitted to chromatography (SiO$_2$, heptane/ethyl acetate 2:1) to give the following: RSC8-1 (76 mg; 22%), 2-bromomethyl-3-octylthioprop-1-yl 2,3,6-tri-O-acetyl-4-O-(2,3,4,6-tetra-O-acetyl-β-D-galactopyranosyl)-β-D-glucopyranoside (72 mg; 24%) having [α]$_D$−7° (c 0.6, CHCl$_3$) and the starting material DIB-6 (34 mg).

The 2-bromomethyl compound above (57 mg, 0.062 mmol) was dissolved in dimethylformamide (1.5 ml) and methyl 11-mercaptoundecanoate (22 mg, 0.093 mmol) and cesium carbonate (30 mg) were added at room temperature. The mixture was stirred for 15 h, worked up with dichloromethane and water and the organic phase was dried (Na$_2$SO$_4$) and concentrated. The residue was chromatographed (SiO$_2$, hexane:ethyl acetate) to give RSC10EC8 (59 mg) which had [α]$_D^{25}$−4° (c 1.8, CDCl$_3$).

NMR-Spectrum (CDCl$_3$, Me$_4$Si): δ (ppm)=5.37 (dd, 1H, J3.5=1.0 Hz, H-4′), 5.22 (t, 1H, J$_{2,3}$=9.3 Hz, H-2), 5.13 (dd, 1H, J$_{2′,3′}$=10.5 Hz, H-2′), 4.97 (dd, 1H, J$_{3′,4′}$=3.3 Hz, H-3′), 4.91 (dd, 1H, J$_{3,4}$=7.7 Hz, H-3), 4.50, 4.48 (two d, each 1H, J$_{1,2}$=7.8 Hz, J$_{1,2}$=7.8 Hz, H-1,1′), 3.69 (s, 3H, OMe), 0.91 (t, 3H, J=6.6 Hz, —CH$_2$—CH$_3$).

TABLE 2

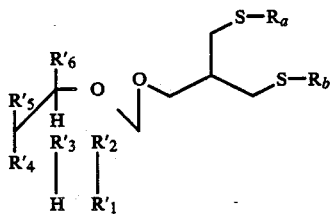

| Compound no. | R′$_1$ | R′$_2$ | R′$_3$ | R′$_4$ | R′$_5$ | R′$_6$ |
|---|---|---|---|---|---|---|
| | R$_a$ = R$_b$ = (CH$_2$)$_{15}$CH$_3$ | | | | | |
| RSC16-1 | OAc$^a$ | H | OAc | OAc | H | CH$_2$OAc |
| RSC16-2 | OAc | H | OAc | H | OAc | CH$_2$OAc |
| RSC16-3 | OAc | H | OAc | OAc | H | COOCH$_3$ |
| RSC16-4 | NPhth$^b$ | H | OAc | OAc | H | CH$_2$OAc |
| RSC16-5 | OAc | H | OAc | OAc | H | H |
| RSC16-6 | OAc | H | OAc | GalAcβ$^c$ | H | CH$_2$OAc |
| RSC16-7 | OAc | H | OAc | H | GalAcα$^d$ | CH$_2$OAc |
| RSC16-8 | OH | H | OH | OH | H | CH$_2$OH |
| RSC16-9 | OH | H | OH | H | OH | CH$_2$OH |
| RSC16-10 | OH | H | OH | OH | H | COOH |
| RSC16-11 | NHAc | H | OH | OH | H | CH$_2$OH |
| RSC16-12 | OH | H | OH | OH | H | H |
| RSC16-13 | OH | H | OH | GalOHβ$^e$ | H | CH$_2$OH |
| RSC16-14 | OH | H | OH | H | GalOHα$^f$ | CH$_2$OH |
| | R$_a$ = R$_b$ = (CH$_2$)$_{17}$—CH$_3$ | | | | | |
| RSC18-1 | OAc | H | OAc | GalAcβ | H | CH$_2$OAc |
| RSC18-2 | OH | H | OH | GalOHβ | H | CH$_2$OH |
| | R$_a$ = R$_b$ = (CH$_2$)$_7$—CH$_3$ | | | | | |
| RSC8-1 | OAc | H | OAc | GalAcβ | H | CH$_2$OAc |
| RSC8-2 | OH | H | OH | GalOHβ | H | CH$_2$OH |
| | R$_a$ = R$_b$ = (CH$_2$)$_{10}$—COOCH$_3$ | | | | | |
| RSC10E-1 | OAc | H | OAc | GalAcβ | H | CH$_2$OAc |
| RSC10E-2 | OH | H | OH | GalOHβ | H | CH$_2$OH |
| | R$_a$ = (CH$_2$)$_{10}$—COOCH$_3$, R$_b$ = (CH$_2$)$_7$—CH$_3$ | | | | | |

TABLE 2-continued

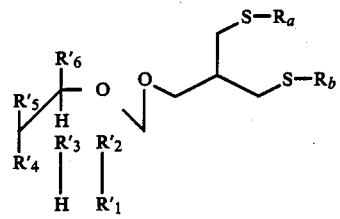

| Compound no. | R′$_1$ | R′$_2$ | R′$_3$ | R′$_4$ | R′$_5$ | R′$_6$ |
|---|---|---|---|---|---|---|
| RSC10EC8 | OAc | H | OAc | GalAcβ | H | CH$_2$OAc |

$^a$Ac = acetyl;
$^b$Phth = phthaloyl;
$^c$GalAcβ = 2,3,4,6-tetra-O—acetyl-β-D—galactopyranosyl;
$^d$GalAcα = 2,3,4,6-tetra-O—acetyl-α-galactopyranosyl;
$^e$GalOHβ = β-D—galactopyranosyl;
$^f$GalOHα = α-D—galactopyranosyl.

EXAMPLE 3

Preparation of bis-sulfoxide and bis-sulfone glycosides (a) A fully acetylated bis-sulfide glycoside (0.5 mmol) was dissolved in ethyl acetate (20 ml) and cooled (−25°). m-Chloroperbenzoic acid (2 mmol) was added and the mixture was stirred until the starting material had been consumed (30–60 min; checked by TLC). The bis-sulfone formed (see Table 4) was purified on a small column of alumina and then isolated by chromatography. Deacetylation was performed as in Example 2. Using the same procedure as above, but with 1 mmol of m-chloroperbenzoic acid, permits the isolation of the corresponding bis-sulfoxide (see Table 3). The following compounds may be prepared:

3-Hexadecylsulfoxy-2-hexadecylsulfoxymethyl-prop-1-yl 2,3,4,6-tetra-acetyl-β-D-glucopyranoside (RSOC161). From RSC166. Yield: 38%. [α]$_D^{25}$−11° (c 1, CDCl$_3$). IR λ1755, 1050 cm$^{-1}$.

NMR-spectrum (CDCl$_3$, Me$_4$Si): δ (ppm)=complete agreement with a diastereomeric mixture as expected of sulfoxides. Sharp signals were: 1.26 (bs, 56H, CH$_2$), 0.88 (t, 3H, J 6.3 Hz, CH$_3$)

Analysis: Calculated for C$_{50}$H$_{92}$O$_{12}$S$_2$ C 63.3 H 9.77 Found: C 62.9 H 9.86

3-Hexadecylsulfonyl-2-hexadecylsulfonylmethyl-prop-1-yl 2,3,4,6-tetra-O-acetyl-β-D-glycopyranoside (RSO$_2$C16-1). From RSC16-1. Yield: 80%. [α]$_D^{23}$=−5.6° (c=0.7 in CDCl$_3$). NMR-Spectrum (CDCl$_3$, TMS): δ (ppm)=5.21 (t, 1 H, J$_{2,3}$=9.5 Hz, H-3), 5.05 (t, 1 H, J$_{3,4}$=J$_{4,5}$=10.0 Hz, H-4), 4.97 (dd, 1 H, H-2), 4.54 (d, 1 H, J$_{1,2}$=8.1 Hz, H-1), 4.27, 4.13 (ABq with further coupling, each 1 H, J$_{AB}$=12.5 Hz, J$_{5,6}$=4.9 Hz, J$_{5′,6′}$=2.4 Hz, H-6,6′), 3.70 (m, 1 H, H-5).

3-Hexadecylsulfonyl-2-hexadecylsulfonylmethyl-prop-1-yl 2,3,4,6-tetra-O-acetyl-β-D-galactopyranoside (RSO$_2$C16-2). From RSC16-2. NMR-Spectrum (CDCl$_3$, TMS): δ (ppm)=5.39 (dd, 1 H, J$_{4,5}$=1.0 Hz, H-4), 5.15 (dd, 1 H, J$_{2,3}$=10.5 Hz, H-2), 5.01 (dd, 1 H, J$_{3,4}$=3.4 Hz, H-3), 4.50 (d, 1H, J$_{1,2}$=7.7 Hz, H-1).

3-Hexadecylsulfonyl-2-hexadecylsulfonylmethyl-prop-1-yl 2,3,6-tri-O-acetyl-4-O-(2,3,4,6-tetra-O-acetyl-β-D-galactopyranosyl-β-D-glucopyranoside (RSO$_2$C16-6). From RSC16-6. Yield: 69%. [α]$_D^{23}$=−6.7° c) =0.8 in CDCl$_3$). NMR-Spectrum (CDCl$_3$, TMS): δ (ppm)=5.35 (dd, 1 H, J$_{4′,5′}$=1 Hz, H-4′), 5.19 (t, 1 H, J$_{2,3}$=9.4 Hz, H-2), 5.11 (dd, 1 H, $J_{2',3'}=10.1$ Hz, H-2'), 4.96 (dd, 1 H, $J_{3',4'}=3.2$ Hz, H-3'), 4.88 (dd, 1 H, $J_{3,4}=7.9$ Hz, H-3), 4.50, 4.48 (two d, each 1 H, $J_{1,2}=J_{1',2'}=7.6$ Hz, H-1 and H-1').

3-Hexadecylsulfonyl-2-hexadecylsulfonylmethyl-prop-1-yl 2,3,6-tri-O-acetyl-4-O-(2,3,4,6-tetra-O-acetyl-α-D-galactopyranosyl)-β-D-galactopyranoside (RSO$_2$C16-7). From RSC16-7. Yield: 99%. $[α]_D^{23}=+47.2°$ (c=0.6 in CDCl$_3$). NMR-Spectrum (CDCl$_3$, TMS): δ (ppm)=5.58 (dd, 1 H, $J_{4',5'}=1$ Hz, H-4'), 5.39 (dd, 1 H, $J_{2',3'}=11$ Hz, H-2'), 5.21 (dd, 1 H, $J_{3',4'}=3.4$ Hz, H-3'), 5.15 (dd, 1 H, $J_{2,3}=11$ Hz, H-2), 4.97 (d, 1 H, $J_{1',2'}=3.9$ Hz, H-1'), 4.79 (dd, 1 H, $J_{3,4}=2.7$ Hz, H-3), 4.51 (d, 1 H, $J_{1,2}=7.8$ Hz, H-1).

3-Hexadecylsulfonyl-2-hexadecylsulfonylmethyl-prop-1-yl β-D-glucopyranoside (RSO$_2$C16-8). From RSO$_2$C16-1. $[α]_D^{23}=+3.9°$ (c=0.9 in CMD). NMR-Spectrum (CMD, TMS): δ (ppm)=4.34 (d, 1 H, $J_{1,2}=7.3$ Hz, H-1), 0.89 (t, 6 H, J=6.8 Hz, CH$_2$—CH$_3$), 3-Hexadecylsulfonyl-2-hexadecylsulfonylmethyl-prop-1-yl β-D-galactopyranoside (RSO$_2$C16-9). From RSO$_2$C16-2.

3-Hexadecylsulfonyl-2-hexadecylsulfonylmethyl-prop-1-yl 4-O-β-D-galactopyranosyl-β-D-glucopyranoside (RSO$_2$C16-13). From RSO$_2$C16-6. $[α]_D^{23}=-1°$ (c=0.5 in CMD). NMR-Spectrum (TMS): δ (ppm)=4.39, 4.31 (d, each 1 H, J=7.6 and 7.8 Hz, H-1,1'), 2.71 (d, 4H, J=6.6 Hz, CH—CH$_2$—SO$_2$), 2.53 (t, 4H, J=7.3 Hz, SO$_2$—CH$_2$—CH$_2$).

3-Hexadecylsulfonyl-2-hexadecylsulfonylmethyl-prop-1-yl 4-O-α-D-galactopyranosyl-β-D-galactopyranoside (RSO$_2$C16-14). From RSO$_2$C16-7. $[α]_D^{23}=+27.4°$ (c=0.8 in CMD). $^{13}$C-NMR-Spectrum (CMD, TMS: δ (ppm)=4.34, (d, 1 H, $J_{1,2}=7.3$ Hz, H-1), 0.89 (t, 1 H, J=6.8 Hz, CH$_2$—CH$_3$). 3-(10-Methoxycarbonyldecylsulfonyl)2-(10-methoxycarbonyldecyl sulfonylmethyl)-prop-1-yl 2,3,6-tri-O-acetyl-4-O-(2,3,4,6-tetra-O-acetyl-β-D-galactopyranosyl)-β-D-glucopyranoside (RSO$_2$C10E-1) and 3-(10-methoxycarbonyldecylsulfonyl)-2-octylsulfonylmethyl-prop-1yl 2,3,6-tri-O-acetyl-4-O-(2,3,4,6-tetra-O-acetyl-β-D-galactopyranosyl)-β-D-glucopyranoside (RSO$_2$C10EC8-1). DIB-6 (2.6 g, 3 mmol) was dissolved in dry dimethylformamide (29 ml) and methyl 11-mercaptoundecanoate (2 ml) was added, followed by cesium carbonate (1.5 g). The reaction was monitored by TLC. After 40 h at 20°, water was added and the mixture was extracted with dichloromethane. Drying and evaporation of the solvents left a residue that was dissolved in ethyl actate (80 ml) and m-chloroperbenzoic acid (12.15 mmol) was added. After 18 h, the mixture was filtered through a column of aluminum oxide (70 g) with dichloromethane (300 ml). The solvents were removed and 10% of the residue was chromatographed (SiO$_2$; hexane/ethyl acetate, 2:3) to give 2-bromomethyl-3-(10-methoxycarbonyldecylsulfonyl)-prop-1-yl 2,3,6-tri-O-acetyl-4-O-(2,3,4,6-tetra-O-acetyl-β-D-galactopyranosyl)-β-D-glucopyranoside (1.00 g, 36%) with $[α]_D-6°$ (c 0.7, CHCl$_3$), followed by RSO$_2$C10E-1 (1.01 g, 31%) with $[α]_D-7°$ (c 1.1, CHCl$_3$)

NMR spectrum (CDCL$_3$, TMS): δ (ppm)=4.48, 4.50 (d, 1H each, J 7.6 and 7.8 Hz, H-1, H-1'), 3.66 (s, 3H, OCH$_3$).

The 2-bromomethyl compound above (820 mg, 0.79 mmol was dissolved in dimethyl formamide (20 ml) and octanethiol (174 mg, 1.19 mmol) was added, followed by cesium carbonate (240 mg). After 20 h, the mixture was partitioned between dichloromethane (120 ml) and water (100 ml) and the aqueous phase was extracted with dichloromethane (50 ml). The combined organic phases were dried (Na$_2$SO$_4$) and concentrated and the residue was submitted to chromatography (SiO$_2$, hexane/ethyl acetate 1:1) to give pure 3-(10-methoxycarbonyldecylsulfonyl)-2-octylthiomethyl-prop-1-yl 2,3,6-tri-O-acetyl-4-O-(2,3,4,6-tetra-O-acetyl-β-D-galactopyranosyl)-β-D-glucopyranoside (830 mg, 96%) with $[α]_D-5°$ (c 0.9, CHCl$_3$) NMR-spectrum (CDCl$_3$, TMS): δ (ppm)=4.48, 4.46 ( m, 1H each, H1, H-1'), 3.67 (s, 3H, OCH$_3$), 0.88 (t, 3H, J6.9 Hz, CH$_2$—CH$_3$)

This sulfone-sulfide (800 mg, 0.74 mmol) was dissolved in ethyl acetate (25 ml) and m-chloroperbenzoic acid (1.85 mmol) was added. After 18 h, the mixture was concentrated and then dissolved in dichloromethane and filtered through a column of alumina (15 mg). Evaporation of the solvents gave pure RSO$_2$C10EC8-1 (667 mg, 80%) with $[α]_D-14°$ (c 0.8, CHCl$_3$).

NMR-spectrum (CDCl$_3$, TMS): δ (ppm)=4.49, 4.47 (d, 1H each, J 7.8 and 7.8 Hz, H-1, H1'), 3.66 (s, 3H, OCH$_3$), 0.87 (t, 3H, J 6.4 Hz, CH$_2$—CH$_3$)

3-(10-Methoxycarbonyldecylsulfonyl)-2-(10-methoxycarbonyldecylsulfonylmethyl)-prop-1-yl 4-O-β-D-galactopyranosyl-β-D-glucopyranoside (RSO$_2$C10E-2). RSO$_2$C10E-1 was conventionally deacetylated (MeOH/MeONa) to give RSO$_2$C10E-2 with $[α]_D-3°$ (c 0.8, CMH).

3-(10-Methoxycarbonyldecylsulfonyl)-2-octylsulfonylmethyl-prop-1-yl 4-O-β-D-galactopyranosyl-β-D-glucopyranoside (RSO$_2$C10EC8-2). RSO$_2$C10EC8-1 was conventionally deacetylated (MeOH/MeONa) to give RSO$_2$C10EC8-2 with $[α]_D-1°$ (c 0.9, CMH). 3-(10-Carboxydecylsulfonyl)-2-(10-carboxydecylsulfonylmethyl)-prop-1-yl 4-O-β-D-galactopyranosyl-β-D-glucopyranoside (RSO$_2$C10A).

RSO$_2$C10E-2 (13 mg, 0.014 mmol) was added to sodium hydroxide solution (0.01M, 10 ml) and heated at 100° for 30 min. The mixture was cooled and acetic acid (1 drop) was added. The solvent was removed to give RSO$_2$C10A, contaminated with sodium acetate.

3-(10-Carboxydecylsulfonyl)-2-octylsulfonylmethyl-prop-1-yl 4-O-β-D-galactopyranosyl-β-D-glucopyranoside (RSO$_2$C10AC8). RSO$_2$C10EC8-2 was treated with sodium hydroxide solution as above to give RSO$_2$C10AC8, contaminated with sodium acetate.

(b) 2-(Hexadecylsulfonyl)ethyl 2,3,4,6-tetra-O-acetyl-β-D-glucopyranoside. 2-Bromoethyl 2,3,4,6-tetra-O-acetyl-β-D-glucopyranoside (Dahmen et al. Carbohydr. Res., 116 (1983)) (540 mg, 1.19 mmol), hexadecanethiol (383 mg, 1.49 mmol), cesium carbonate (292 mg, 0.89 mmol) and dimethylformamide (5 ml) was stirred overnight. Dichloromethane (75 ml) and water (40 ml) were added. The aqueous phase was extracted with dichloromethane (2×25 ml), the combined organic phases were dried (Na$_2$SO$_4$) and concentrated. Chromatography (SiO$_2$; ethylacetate: hexane) gave pure 2-(hexadecylthio)ethyl 2,3,4,6-tetra-O-acetyl-β-D-glucopyranoside (480 mg, 0.76 mmol, 64%), which was dissolved in ethyl acetate (12 ml) and treated with m-chloroperbenzoic acid (1.71 mmol). After 4 hours the solvents were removed and the residue was dissolved in dichloromethane and filtered through alumina (10 g) to give the pure sulfone lipid (495 mg, 98%). $[α]_D^{23}=-8.7°$ (c=0.9 in CDCl$_3$).

NMR-Spectrum (CDCl$_3$, TMS): δ (ppm)=5.21 (t, 1 H, $J_{3,4}=9.5$ Hz, H-3), 5.07 (t, 1 H, $J_{4,5}=9.7$ Hz, H-4), 5.00 (dd, 1 H, $J_{2,3}$=9.5 Hz, H-2), 4.57 (d, 1 H, $J_{1,2}$=8.1 Hz, H-1), 4.28, 4.14 (ABq with further coupling, each 1 H, $J_{AB}$=12.5 Hz, $J_{5,6'}$=4.88 Hz, $J_{5,6'}$=2.44 Hz, H-6,6'), 3.72 (m, 1 H, H-5). 2-(Hexadecylsulfonyl)ethyl β-D-glucopyranoside. The sulfone lipid above (440 mg) was dissolved in dichloromethane (45 ml), and methanolic sodium methoxide (30 ml; from 1 mg Na) was added. After 24 hours (TLC showed complete deacetylation), acetic acid (1 drop) was added and the solvents were removed, finally at <0.1 Torr, to give the deacetylated material (320 mg, 97%), contaminated with a small amount of sodium acetate. $[\alpha]_D^{23}$=−10,5° (c=1,0 in CMD). NMR-Spectrum (CMD, TMS): δ (ppm)=4.36 (d, 1 H, $J_{1,2}$=7.8 Hz, H-1), 0.89 (t, 3 H, J=6.8 Hz, $CH_2$-$CH_3$).

TABLE 3

| Compound no. | $R'_1$ | $R'_2$ | $R'_3$ | $R'_4$ | $R'_5$ | $R'_6$ |
|---|---|---|---|---|---|---|
| R = $(CH_2)_{15}CH_3$ | | | | | | |
| RSOC16-1 | OAc[a] | H | OAc | OAc | H | $CH_2OAc$ |
| RSOC16-2 | OAc | H | OAc | H | OAc | $CH_2OAc$ |
| RSOC16-3 | OAc | H | OAc | OAc | H | $COOCH_3$ |
| RSOC16-4 | NPhth[b] | H | OAc | OAc | H | $CH_2OAc$ |
| RSOC16-5 | OAc | H | OAc | OAc | H | H |
| RCOC16-6 | OAc | H | OAc | GalAcβ[c] | H | $CH_2OAc$ |
| RSOC16-7 | OAc | H | OAc | H | GalAcα[d] | $CH_2OAc$ |
| RSOC16-8 | OH | H | OH | OH | H | $CH_2OH$ |
| RSOC16-9 | OH | H | OH | H | OH | $CH_2OH$ |
| RSOC16-10 | OH | H | OH | OH | H | COOH |
| RSOC16-11 | NHAc | H | OH | OH | H | $CH_2OH$ |
| RSOC16-12 | OH | H | OH | OH | H | H |
| RSOC16-13 | OH | H | OH | GalOHβ[e] | H | $CH_2OH$ |
| RSOC16-14 | OH | H | OH | H | GalOHα[f] | $CH_2OH$ |
| R = $(CH_2)_{17}$—$CH_3$ | | | | | | |
| RSOC18-1 | OAc | H | OAc | GalAcβ | H | $CH_2OAc$ |
| RSOC18-2 | OH | H | OH | GalOHβ | H | $CH_2OH$ |
| R = $(CH_2)_7$—$CH_3$ | | | | | | |
| RSOC8-1 | OAc | H | OAc | GalAcβ | H | $CH_2OAc$ |
| RSOC8-2 | OH | H | OH | GalOHβ | H | $CH_2OH$ |
| R = $(CH_2)_{10}$—$COOCH_3$ | | | | | | |
| RSOC10E-1 | OAc | H | OAc | GalAcβ | H | $CH_2OAc$ |
| RSOC10E-2 | OH | H | OH | GalOHβ | H | $CH_2OH$ |

[a]Ac = acetyl;
[b]Phth = phthaloyl;
[c]GalAcβ = 2,3,4,6-tetra-O—acetyl-β-D-galactopyranosyl;
[d]GalAcα = 2,3,4,6-tetra-O—acetyl-α-D-galactopyranosyl;
[e]GalOHβ = β-D-galactopyranosyl;
[f]GalOHα = α-D-glactopyranosyl.

TABLE 4

| Compound no. | $R'_1$ | $R'_2$ | $R'_3$ | $R'_4$ | $R'_5$ | $R'_6$ |
|---|---|---|---|---|---|---|
| $R_a = R_b = (CH_2)_{15}CH_3$ | | | | | | |
| $RSO_2C16$-1 | OAc[a] | H | OAc | OAc | H | $CH_2OAc$ |
| $RSO_2C16$-2 | OAc | H | OAc | H | OAc | $CH_2OAc$ |
| $RSO_2C16$-3 | OAc | H | OAc | OAc | H | $COOCH_3$ |
| $RSO_2C16$-4 | NPhth[b] | H | OAc | OAc | H | $CH_2OAc$ |
| $RSO_2C16$-5 | OAc | H | OAc | OAc | H | H |
| $RSO_2C16$-6 | OAc | H | OAc | GalAcβ[c] | H | $CH_2OAc$ |
| $RSO_2C16$-7 | OAc | H | OAc | H | GalAcα[d] | $CH_2OAc$ |
| $RSO_2C16$-8 | OH | H | OH | OH | H | $CH_2OH$ |
| $RSO_2C16$-9 | OH | H | OH | H | OH | $CH_2OH$ |
| $RSO_2C16$-10 | OH | H | OH | OH | H | COOH |

TABLE 4-continued

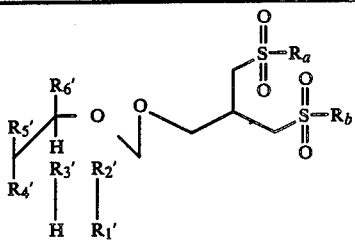

| Compound no. | R'$_1$ | R'$_2$ | R'$_3$ | R'$_4$ | R'$_5$ | R'$_6$ |
|---|---|---|---|---|---|---|
| RSO$_2$C16-11 | NHAc | H | OH | OH | H | CH$_2$OH |
| RSO$_2$C16-12 | OH | H | OH | OH | H | H |
| RSO$_2$C16-13 | OH | H | OH | GalOHβ$^e$ | H | CH$_2$OH |
| RSO$_2$C16-14 | OH | H | OH | H | GalOHα$^f$ | CH$_2$OH |
| R$_a$ = R$_b$ = (CH$_2$)$_{17}$—CH$_3$ | | | | | | |
| RSO$_2$C18-1 | OAc | H | OAc | GalAcβ | H | CH$_2$OAc |
| RSO$_2$C18-2 | OH | H | OH | GalOHβ | H | CH$_2$OH |
| R$_a$ = R$_b$ = (CH$_2$)$_7$—CH$_3$ | | | | | | |
| RSO$_2$C8-1 | OAc | H | OAc | GalAcβ | H | CH$_2$OAc |
| RSO$_2$C8-2 | OH | H | OH | GalOHβ | H | CH$_2$OH |
| R$_a$ = R$_b$ = (CH$_2$)$_{10}$—COOCH$_3$ | | | | | | |
| RSO$_2$C10E-1 | OAc | H | OAc | GalAcβ | H | CH$_2$OAc |
| RSO$_2$C10E-2 | OH | H | OH | GalOHβ | H | CH$_2$OH |
| R$_a$ = R$_b$ = (CH$_2$)$_{10}$COOH | | | | | | |
| RSO$_2$C10A | OH | H | OH | GalOHβ | H | CH$_2$OH |
| R$_a$ = (CH$_2$)$_{10}$COOCH$_3$, R$_b$ = (CH$_2$)$_7$CH$_3$ | | | | | | |
| RSO$_2$—C10EC8-1 | OAc | H | OAc | GalAcβ | H | CH$_2$OAc |
| RSO$_2$C10EC8-2 | OH | H | OH | GalOHβ | H | CH$_2$OH |
| R$_a$ = (CH$_2$)$_{10}$COOH, R$_b$ = (CH$_2$)$_7$CH$_3$ | | | | | | |
| RSO$_2$C10AC8 | OH | H | OH | GalOHβ | H | CH$_2$OH |

$^a$Ac = acetyl;
$^b$Phth = phthaloyl;
$^c$GalAcβ = 2,3,4,6-tetra-O—acetyl-β-D-galactopyranosyl;
$^d$GalAcα = 2,3,4,6-tetra-O—acetyl-α-D-galactopyranosyl;
$^e$GalOHβ = β-D-galactopyranosyl;
$^f$GalOHα = α-D-galactopyranosyl.

EXAMPLE 4

The use of 2-bromomethylallyl glycosides with sulfur, nitrogen and oxygen nucleophiles A DIB glycoside (1 mmol) was dissolved in ethyl acetate (10 ml) and diazabicycloundecane (DBU; 2 mmol) was added dropwise. After ca. 5 h (crystalline DBU-hydrobromide had been formed), 1 mmol of an appropriate thiol was added. Alternatively, an equivalent amount of an appropriate amine or alcohol may be added. The reaction was monitored by TLC, which showed that the intermediate allylic bromide glycoside was consumed and that a new product was formed. The solid material was removed and the residue was subjected to chromatography, which gave the pure product. Deacetylation was performed as in Example 2. The following compounds may be prepared:

2-(2-Methoxycarbonylethylthiomethyl)prop-2-en-1-yl 2,3,4,6-tetra-O-acetyl-β-D-glucopyranoside (ARSC2E-1). From DIB-1.

2-(2-Methoxycarbonylethylthiomethyl)prop-2-en-1-yl β-D-glucopyranoside (ARSC2E-2). From ARSC2E-1.

2-(2-Methoxycarbonylethylthiomethyl)prop-2-en-1-yl 2,3,4,6-tetra-O-acetyl-β-D-galactopyranoside (ARSC2E-3). From DIB-2.

2-(2-Methoxycarbonylethylthiomethyl)prop-2-en-1-yl β-D-galactopyranoside (ARSC2E-4). From ARSC2E-3.

2-(2-Methoxycarbonylethylthiomethyl)prop-2-en-1-yl 2,3,6-tri-O-acetyl-4-O-(2,3,4,6-tetra-O-acetyl-β-D-galactopyranosyl)-β-D-glucopyranoside (ARSC2E-5). From DIB-6. Yield: 43%. [α]$_D^{23}$= −11.5° (c=0.8 in CDCl$_3$). NMR-Spectrum (CDCl$_3$, TMS): β (ppm)=5.35 (dd, 1 H, J$_{4',5'}$=0.7 Hz, H-4'), 5.20 (t, 1 H, J$_{2,3}$=9.3 Hz, H-2), 5.12, 5.07 (bs, each 1 H, =CH$_2$), 5.11 (dd, 1 H, J$_{2',3'}$=9.8 Hz, H-2'), 4.95 (dd, 1 H, J$_{3',4'}$=3.4 Hz, H-3'), 4.93 (t, 1 H, J$_{3,4}$=8.1 Hz, H-3), 4.51, 4.48 (d, each 1 H, J$_{1,2}$=7.8 Hz, H-1,1'), 4.37, 4.17 (ABq, each 1 H, J$_{Ab}$=12.0 Hz, O—CH$_2$—C=), 3.70 (s, 3 H, OCH$_3$), 3.17, 3.14 (ABq, each 1 H, =C—CH$_2$—S).

2-(2-methoxycarbonylethylthiomethyl)prop-2-en-1-yl 4-O-β-D-galactopyranosyl-β-D-glycopyranoside (ARSC2E-6). From ARSC2E-5.

2-(2-Methoxycarbonylethylthiomethyl)prop-2-en-1-yl 2,3,6-tri-O-acetyl-4-O-(2,3,4,6-tetra-O-acetyl-α-D-galactopyranosyl)-β-D-galactopyranoside (ARSC2E-7). From DIB-7. Yield: 44%. [α]$_d$= +53° (c=0.8 in CDCl$_3$). NMR-Spectrum (CDCl$_3$, TMS): δ (ppm)=5.57 (dd, 1 H, J$_{4',5'}$=1.2 Hz, H-4'), 5.38 (dd, 1 H, J$_{2',3'}$=11.0 Hz, H-2'), 5.21 (dd, 1 H, J$_{2,3}$=10.8 Hz, H-2), 5.20 (dd, 1 H, J$_{3',4'}$=3.4 Hz, H-3'), 5.16, 5.07 (bs, each 1 H, =CH$_2$), 5.00 (d, 1 H, J$_{1',2'}$=3.7 Hz, H-1'), 4.82 (dd, 1 H, J$_{3,4}$=2.9 Hz, H-3), 4.51 (d, 1 H, J;hd 1,2=7.6 Hz, H-1), 4.41, 4.20 (ABq, each 1 H, J$_{AB}$=12.3 Hz, O—CH$_2$—C=), 3.70 (s, 3 H, OCH$_3$), 3.21, 3.17 (ABq, each 1 H, J$_{AB}$=14.1 Hz, =C—CH$_2$—S).

2-(2-Methoxycarbonylethylthiomethyl)prop-2-en-1-yl 4-O-α-D-galactopyranosyl-β-D-galactopyranoside (ARSC2E-8). From ARSC2E-7.

2-(Hexadecylthiomethyl)prop-2-en-1-yl 2,3,4-tri-O-acetyl-β-D-xylopyranoside (ARSC16-1). From DIB-5. Yield: 42%. NMR-Spectrum (CDCl$_3$, TMS): δ (ppm)=5.20–4.88 (m, 3 H, H-3,2,4), 5.09, 5.01 (bs, each 1 H, =CH$_2$), 4.51, (d, 1 H, J$_{1,2}$=6.9 Hz, H-1), 4.37 4.13 (ABq, each 1 H, J$_{AB}$=12.4 Hz, C—CH$_2$—O), 4.16–4.08 (m, 1 H, H-5), 3.35 (dd, 1 H, J$_{4,5'}$=8.6 Hz, J$_{5,5'}$=11.8 Hz, H-5'), 3.13 (s, 2 H, =C—CH$_2$—S), 2.35 (t, 2 H, J=7 Hz, CH$_2$—CH$_2$—S).

2-(Hexacedylthiomethyl)prop-2-en-1-yl β-D-xylopyranoside (ARSC16-2). From ARSC16-1.

2-Hexadecylthiomethyl)prop-2-en-1-yl 2,3,4,6-tetra-O-acetyl-β-D-galactopyranoside (ARSC16-3). From DIB-2.

2-(Hexadecylthiomethyl)prop-2-en-1-yl β-D-galactopyranoside (ARSC16-4). From ARSC16-3.

2-(Hexadecylthiomethyl)prop-2-en-1-yl 2,3,4,6-tetra-O-acetyl-β-D-glucopyranoside (ARSC16-5). From DIB-1. Yield: 50%. [α]$_D^{23}$ = −14.7° (c=1.4 in CDCl$_3$).

NMR-Spectrum (CDCl$_3$, TMS): δ (ppm)=5.21 (t, 1 H, J$_{2,3}$=J$_{3,4}$=9.4 Hz, H-3), 5.10 (t, 1 H, J$_{4,5}$=9.8 Hz, H-4), 5.097, 5.03 (s, each 1 H, =CH$_2$), 5.04 (t, 1 H, H-2), 4.54 (d, 1 H, J$_{1,2}$=8.0 Hz, H-1), 4.41, 4.20 (ABq, each 1 H, J$_{AB}$=15.0 Hz, O—CH$_2$—C=), 4.27, 4.15 (ABq with further coupling, each 1 H, J$_{AB}$=12.0 Hz, J$_{5,6}$=4.6 Hz, J$_{5,6'}$=2.4 Hz, H-6,6'), 3.69 (octet, 1 H, H-5), 3.15, 3.11 (ABq, each 1 H, J$_{AB}$=13.9 Hz, =C—CH$_2$—S), 2.36 (t, 2 H, J=7 Hz, S—CH$_2$—CH$_2$).

2-(Hexadecylthiomethyl)prop-2-en-1-yl β-D-glucopyranoside (ARSC16-6). From ARSC16-5.

2-(Hexadecylthiomethyl)prop-2-en-1-yl 2,3,6-tri-O-acetyl-4-O-(2,3,4,6-tetra-O-acetyl-β-D-galactopyranosyl)-α-D-glucopyranoside (ARSC16-7). From DIB-6. Yield: 46%. [α]$_D^{23}$ = −11.0° (c=1.4 in CDCl$_3$). NMR-Spectrum (CDCl$_3$, TMS): δ (ppm)=5.34 (dd, 1 H, J$_{4',5'}$=1.0 Hz, H-4'), 5.20 (t, 1 H, J$_{2,3}$=9.0 Hz, H-2), 5.11 (dd, 1 H, J$_{2',2'}$=−10.1 Hz, H-2'), 5.08, 5.02 (bs, each 1 H, =CH$_2$), 4.95 (dd, 1 H, J$_{3',4'}$=3.7 Hz, H-3'), 4.93 (t, 1 H, J$_{3,4}$=8.1 Hz, H-3), 4.51, 4.48 (d, each 1 H, J$_{1,2}$=7.8 Hz, H-1,1), 4.38, 4.16 (ABq, each 1 H, J$_{AB}$=12.0 Hz, O—CH$_2$—C=), 3.14, 3.10 (ABq, each 1 H, J$_{AB}$=14.3 Hz, =C—CH$_2$—S), 2.37 (t, 1 H, J=7.4 Hz, S—CH$_2$—CH$_2$).

2-(Hexadecylthiomethyl)prop-2-en-1-yl 4-O-β-D-galactopyranosyl-β-D-glucopyranoside (ARSC16-8). From ARSC16-7.

2-(Hexadecylthiomethyl)prop-2-en-1-yl 2,3,6-tri-O-acetyl-4-O-(2,3,4,6-tetra-O-acetyl-α-D-galactopyranosyl)-β-D-galactopyranoside (ARSC16-9). From DIB-7. Yield 50%. [α]$_D^{23}$ = +56,4° (c=0.5 in CDCl$_3$). NMR-Spectrum (CDCl$_3$, TMS): δ (ppm)=5.57 (dd, 1 H, J$_{4',5'}$=1 Hz, H-4'), 5.38 (dd, 1 H, J$_{2',3'}$=11.0 Hz, H-2'), 5.21 (dd, 1 H, J$_{2,3}$=10.7 Hz, H-2), 5.20 (dd, 1 H, J$_{3',4'}$=3.2 Hz, H-3'), 5.12, 5.03 (bs, each 1 H, =CH$_2$), 5.00 (d, 1 H, J$_{1',2'}$=3.7 Hz, H-1'), 4.82 (dd, 1 H, J$_{3,4}$=2.7 Hz, H-3), 4.51 (d, 1 H, J$_{1,2}$=7.8 Hz, H-1), 4.42, 4.20 (ABq, each 1 H, J$_{AB}$=12.3 Hz, O—CH$_2$—C=), 3.17, 3.14 (ABq, each 1 H, J$_{AB}$=14.2 Hz, =C—CH$_2$—S), 2.39 (t, 2 H, J=7.3 Hz, S—CH$_2$—CH$_2$). 2-(Hexadecylthiomethyl)prop-2-en-1-yl 4-O-α-D-galactopyransoyl-β-D-galactopyranoside (ARSC16-10). From ARSC16-9.

2-(10-Methoxycarbonyldecylthiomethyl)prop-2-en-1-yl 2,3,6-tri-O-acetyl-4-O-(2,3,4,6-tetra-O-acetyl-β-D-galactopyranosyl)-β-D-glucopyranoside (ARSC10E-1). From DIB-6. Yield: 52%. [α]$_D^{23}$= −8.9° (c=CDCl$_3$). NMR-Spectrum (CDCl$_3$, TMS): δ (ppm)=5.35 (dd, 1 H, J$_{4',5'}$=0.7 Hz, H-4'), 5.20 (t, 1 H, J$_{2,3}$=9.0 Hz, H-2), 5.11 (dd, 1 H, J$_{2',3'}$=−10.5 Hz, H-2'), 5.08, 5.02 (bs, each 1 H, =CH$_2$), 4.95 (dd, 1 H, J$_{3',4'}$=3.5 Hz, H-3'), 4.94 (t, 1 H, J$_{3,4}$=8,5 Hz, H-3), 4.50, 4.48 (d, each 1 H, J$_{1,2}$=J$_{1',2'}$=7,8 Hz, h-1,1'), 4.38, 4.16 (ABq, each 1 H, J$_{AB}$=12.0 Hz, O—CH$_2$—C=), 3.67 (s, 3 H, OCH$_3$), 3.14, 3.10 (ABq, each 1 H, J$_{AB}$=14.5 Hz, =C—CH$_2$—S), 2.37 (t, 2 H, J=7.5 Hz, S—CH$_2$—CH$_2$), 2.30 (t, 2 H, J=7.5 Hz, CH$_2$—COO).

2-(10-Methoxycarbonyldecylthiomethyl)prop-2-en-1-yl 4-O-β-D-galactopyranosyl-β-D-glucopyranoside (ARSC10E-2). From ARSC10E-1.

2-(10-Methoxycarbonyldecylthiomethyl)prop-2-en-1-yl 2,3,6-tri-O-acetyl-4-O-(2,3,4,6-tetra-O-acetyl-α-D-galactopyranosyl)-β-D-galactopyranoside (ARSC10E-3). From DIB-7. Yield: 51%. [α]$_D^{23}$= +55° (c=1.1 in CDCl$_3$). NMR-Spectrum (CDCl$_3$, TMS): δ (ppm)=5.57 (dd, 1 H, J$_{4',5'}$=1.2 Hz, H-4'), 5.38 (dd, 1 H, J$_{2',3'}$=11.0 Hz, H-2'), 5.21 (dd, 1 H, J$_{2,3}$=10.5 Hz, H-2), 5.20 (dd, 1 H, J$_{3',4'}$=3.2 Hz, H-3'), 5.12, 5.03 (bs, each 1 H, =CH$_2$), 5.00 (d, 1 H, J$_{1',2'}$=3.7 Hz, H-1'), 4.82 (dd, 1 H, J$_{3,4}$=2.9 Hz, H-3), 4.51 (d, 1 H, J$_{1,2}$=7.8 Hz, H-1), 4.42 4.20 (ABq, each 1 H, J$_{AB}$=12.7 Hz, O—CH$_2$—C=), 3.67 (s, 3 H, OCH$_3$), 3.17, 3.14 (ABq, each 1 H, J$_{AB}$=14.2 Hz, =C—CH$_2$—S), 2.39 (t, 2 H, J$_{7,3}$ Hz, S—CH$_2$CH$_2$), 2.30 (t, 2 H, J=7.8 Hz, CH$_2$COO).

EXAMPLE 5

Preparation of neo-glycoconjugates (a) Glycosides with one or two terminal ester groups (RSO$_2$C10E-2, RSO$_2$C10EC8-2, and ARSC2E-3) were transformed into the corresponding acyl azides, essentially as described by Dahmén et al. (Carbohydr. res. 129 (1984) in their preparation of neo-glycoconjugates. The reaction mixture containing the acyl azide in methylsulfoxide was added dropwise to the amino-group-containing carrier in Na$_2$B$_4$O$_7$-RHCO$_3$ buffer (see Dahmén et al.) at pH 9.0–9.3 and the resulting mixture was stirred over night. The following conjugates were prepared. RSO$_2$C10EC8-2.BSA. From RSO$_2$C10EC8-2 (50 mg, 0.07 mmol) and bovine serum albumin (BSA, 65 mg). The reaction mixture was dialyzed (4×5 l distilled water) and the residue was freeze-dried to give the neo-glycoprotein. The degree of binding (number of sugar units per protein molecule) was 21 as determined by differential sulfur combustion analysis. ARSC2E-3.BSA. ARSC2E-2 was conventionally deacetylated to give ARSC2E-3 (36 mg, 0.07 mmol) which was coupled to BSA (65 mg) as above. Freeze-drying gave the neo-glycoprotein which had a degree of binding of 18 as determined by differential sulfur combustion analysis.

RSO$_2$C10EC8-2. spermidine. From RSO$_2$C10EC8-2 (94 mg, 0.13 mmol) and spermidinium trichloride (12,1 mg, 0.067 mmol). The crude product separated as a gel and was isolated by filtration of the reaction mixture and then chromatographed (SiO$_2$, CMH, 65/35/10) to give the pure conjugate. RSO$_2$C10E-2.SiO$_2$. From RSO$_2$C10E-2 (50 mg, 0.054 mmol) and aminated silica gel (166 mg, Sperisorb 5 μm, 0.6 mmol amino groups/g; Phase Sep, Deeside Ind. Est., Queensferry, Clwyd, UK). The resulting glycoconjugate was washed twice with water, methanol and dichloromethane by centrifugation. Drying under vacuum gave 154 mg of the pure glycoconjugate. The degree of binding was 0.13 mmol of the sugar hapten/per g of the conjugate as determined by sulfur combustion analysis.

ARSC2E-3.SiO$_2$ was conventionally deacetylated to give ARSC2E-3 (46 mg, 0.09 mmol) which was coupled to the aminated silica gel (95 mg), worked up and purified as above to give 88 mg of the pure glycoconjugate. The degree of binding was 0.19 mmol of the sugar hapten/per g of the conjugate as determined by sulfur combustion analysis.

(b) ARSC3-SiO$_2$. A fully acetylated DIB glycoside (DIB-6, 85 mg, 0.1 mmol) was dissolved in dry ethyl acetate (1.5 ml) and diazabicycloundecane (46 mg, 0.3 mmol, 45 μl) was added. The mixture was stirred for 3 h and thiolated silica gel (114 mg, prepared by treating Lichrosorb, Merck, 10 μm, ~300 m$^2$/g, 3-trimethoxysilylpropan-1-thiol; ~0.9 mmol thiol/g of product) was added. After 2 h, the sugar was consumed (according to TLC analysis) and the conjugate was washed with dichloromethane, water and methanol on a glass filter. The conjugate was deacetylated with methanolic sodium methoxide (0.02M, 1 ml) over night, washed with water, methanol, dichloromethane and ether, and dried. The degree of binding was 0.23 mmol of the sugar hapten/per g of the conjugate as determined by carbon combustion analysis. This means that ~25% of the available thiol groups had reacted.

EXAMPLE 6

Preparation of multi-dentate glycosides

A fully acetylated DIB glycoside (1 mmol), an alkyldithiol (1 mmol), cesium carbonate (1 mmol) and dimethyl-formamide (2 mmol) is stirred at room temperature under nitrogen for 24–48 hours. The reaction mixture is worked-up as in Example 3 to give a mixture of multidentate glycosides. Deacetylation as in Example 2 gives the polymer with sugar units attached to the alkyl polysulfide backbone. The degree of polymerization is determined by chromatography on Sephadex gel.

TABLE 5

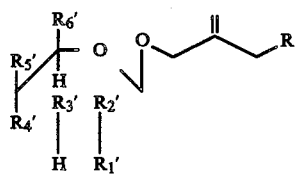

| Compound no. | R'$_1$ | R'$_2$ | R'$_3$ | R'$_4$ | R'$_5$ | R'$_6$ |
|---|---|---|---|---|---|---|
| R = S—(CH$_2$)$_{15}$CH$_3$ | | | | | | |
| ARSC16-1 | OAc | H | OAc | OAc | H | H |
| ARSC16-2 | OAc | H | OAc | H | H | CH$_2$OAc |
| ARSC16-3 | OAc | H | OAc | GalAcβ | H | CH$_2$OAc |
| ARSC16-4 | OAc | H | OAc | H | GalAcα | CH$_2$OAc |
| R = S—(CH$_2$)$_2$COOCH$_3$ | | | | | | |
| ARSC2E-1 | OAc | H | OAc | GalAcβ | H | CH$_2$OAc |
| ARSC2E-2 | OAc | H | OAc | H | GalAcα | CH$_2$OAc |
| ARSC2E-3 | OH | H | OH | H | GalAcα | CH$_2$OH |
| R = S—(CH$_2$)$_{10}$COOCH$_3$ | | | | | | |
| ARSC10E-1 | OAc | H | OAc | GalAcβ | H | CH$_2$OAc |
| ARSC10E-2 | OAc | H | OAc | H | GalAcα | CH$_2$OAc |
| R = S—(CH$_2$)$_3$—SiO$_2$ | | | | | | |
| ARSC3-SiO$_2$ | OH | H | OH | GalOHβ | H | CH$_2$OH |

EXAMPLE 7

Formation of liquid crystals in dimethylsulfoxide

A bis-sulfide glycolipid (RSC16-8, RSC16-9, or RSC16-12; 5–10 mg) was dissolved by gentle heating in dimethylsulfoxide (1 ml). When the temperature had dropped to 30°–35° C., the still transparent mixture became semi-solid. Inspection of the mixture with a polarising microscope revealed that liquid crystals had formed, preferentially in the vicinity of entrapped bubbles of air. When the mixture was left for several hours, more stable aggregates (probably crystals) were formed as a precipitate and the remaining liquid became fluid.

EXAMPLE 8

Assay for virus binding specificity and estimation of relative binding strength (a) Thin-layer plate method The assay for the detection of virus binding to glycolipids and for testing of detailed specificity of binding is of decisive importance (cf. (Hansson et al., FEBS Lett. 170, 1984, pp. 15–18). In principle, the virus to be assayed is layered on a chromatogram with separated glycolipids from target cells or other sources and allowed to interact with potential receptor substances. After careful washings, bound virus is detected by anti-virus antibody and radiolabelled anti-antibody followed by autoradiography. In some cases, the virus particle was directly labelled before binding. The detailed procedure is as follows: Mixtures of total lipids (up to 100 μg in each lane) or total glycolipids (20–40 μg in each lane) or pure glycolipids (0.01–1 μg) were separated on aluminium sheets, about 5×5 cm, coated with silica gel 60 (Merck), usually with chloroform/methanol/water (60:35:8, by volume) as the solvent for non-acid glycolipids, and with chloroform/methanol/2.5M ammonia for non-acid glycolipids, and with chloroform/methanol/2.5M ammonia (60:40:9, by volume) as the solvent for acid glycolipids. For purposes of comparison, a parallel plate is detected chemically by spraying and heating with anisaldehyde solution. For virus binding, the dried chromatogram with separated substances is dipped for 1 minute in 200 ml of diethylether containing 0.5% (w/v) of polyisobutylmethacrylate (Plexigum P28, Röhm GmbH, Darmstadt) and dried for 2 minutes. The plate is then sprayed with phosphate-buffered saline (PBS) of pH 7.3 containing 2% bovine serum albumin (BSA) and 0.1% NaN$_3$ (solution A) and then immersed in solution A and placed in a Petri dish for 2 hours. After tipping off solution A, the virus suspension is added (about 25 μg per ml with about 2 ml for a plate of the dimensions given above) to the chromatogram placed horizontally in the humidified atmosphere of a Petri dish. After incubation for 2 hours, the virus suspension is tipped off and the plate is washed six times with PBS, 1 minute each time. In a typical case of antibody, monoclonal antibody 817 directed against Sendai virus produced in ascitic fluid is diluted 1:100 with solution A, using about 2 ml per plate, with incubation for 2 hours. After washing five times with PBS, about 2 ml of rabbit anti-mouse Fab is incubated for 2 hours (4×10$^5$ cpm/ml of $^{125}$I-labelled F(ab')$_2$, the Radiochemical Centre, Amersham). After six washings in PBS, the plate is dried and exposed to XAR-5 X-ray film (Eastman), usually for 2–3 days, using an intensifying screen.

The treatment with plastic produces a hydrophobic surface. Separated glycolipid or other bands are thus induced to be exposed on the hydrophobic solid surface similar to the way lipids are exposed in the biological membrane. This means that the test substance is densely anchored with its paraffin chains in the plastic surface with the polar head groups exposed and accessible to the invironment. This mimics the surface monolayer of the living cell. This plastic treatment is highly critical for specificity and reproducibility and explains the advantage of this solid-phase method over traditional inhibition assays based on "solubilized" aggregates or micelles.

The detection limit varies with the avidity of the ligand but is in the range of 5-50 ng of receptor, or in about the same picomole range. For a receptor candidate to be considered negative, there should be no darkening at a one or more microgram level. Good binders give saturating black bands at 10 ng. An obvious advantage of this assay is that mixtures or substances are first separated into substance species, avoiding the risk of shielding of minor components, or false negative binding due to contaminating substance. Also, the coating with albumin blocks unspecific hydrophobic sites, which otherwise may cause false positive results. Finally, the extensive washings remove or detach unspecific associations. By comparison, traditional inhibition assays usually incubate virus with target cells in suspension in the absence or presence of sonicated micelles. In case of hemolysis assay, simple photometry is done on the mixture after centrifugation (cf. Huang, Lipids 18, 1983, pp. 489-492 ). Thus, no albumin is present, and there are no washing steps analogous to the present assay.

(b) Quantitation of virus binding by autoradiography of microtiter wells.

For quantification of virus binding, a technique was adopted from the analogous solid-phase binding of antibodies to microtiter wells (Brockhaus et al., J. Biol. Chem. 256, 1981, pp. 13223-13225). A dilution series of glycolipid or other substances in 50 $\mu$l of methanol is allowed to evaporate in the microtiter well overnight at room temperature. 100 $\mu$l of 2% BSA in PBS are then incubated for 2 hours after which the well is rinsed once with the same volume of solution. 50 $\mu$l of a suspension of 1.5 $\mu$g of virus in BSA-PBS is incubated for 4 hours, followed by four washings with 100 $\mu$l each of BSA-PBS. In case of Sendai virus, 50 $\mu$l of ascitic fluid-produced antibody 817 diluted 1:100 in solution A is incubated for 4 hours followed by four washings. Finally, 50 $\mu$l of rabbit anti-mouse Fab (2.5$\times$10$^4$ cpm $^{125}$I-labelled F(ab')$_2$, the Radiochemical Centre, Amersham) is incubated overnight at 4° C. followed by five 100 $\mu$l washings with BSA-PBS. The wells are cut from the plate and assayed individually for $^{125}$I in a spectrometer. The procedure above was used to study the binding of Sendai virus to the synthetic glycolipid analogues of the present invention. The compounds of the invention studied were Glc$\beta$→OCH$_2$CH(CH$_2$SO$_2$(CH$_2$)$_{15}$CH$_3$)$_2$ (compound A) and Gal$\beta$1→4Glc$\beta$→OCH$_2$CH(CH$_2$SO$_2$(CH$_2$)$_{15}$CH$_3$)$_2$ (compound B) in comparison with two natural receptors, viz. Gal$\beta$→Ceramide and Glc$\beta$→Ceramide.

Semiquantitatively, compound A and compound B both showed excellent ability to bind the virus. More quantitatively, compound b showed approximately the same binding capacity as the natural comparison receptors. See also Table 6 below.

TABLE 6

| Binding of Sendai virus to natural and synthetic glycolipids | | |
|---|---|---|
| Glycolipid | Method | Result |
| Glc$\beta$O—CH$_2$CH(CH$_2$S(CH$_2$)$_{15}$CH$_3$)$_2$ | TLC (Ex. 8a) | (+) |
| Glc$\beta$O—CH$_2$CH(CH$_2$SO$_2$(CH$_2$)$_{15}$CH$_3$)$_2$ | TLC (Ex. 8a) | + |
| Glc$\beta$O—(CH$_2$)$_2$SO$_2$SO$_2$(CH$_2$)$_{15}$CH$_3$ | TLC (Ex. 8a) | + |
| Gal$\beta$O-ceramide | Autorad. MT-wells (Ex. 8b) | + |
| Glc$\beta$O-ceramide | Autorad. MT-wells (Ex. 8b) | + |
| Glc$\beta$O—CH$_2$CH(CH$_2$SO$_2$(CH$_2$)$_{15}$CH$_3$)$_2$ | Autorad. MT-wells (Ex. 8b) | + |
| Gal$\beta$1 → 4Glc$\beta$O—CH$_2$CH(CH$_2$SO$_2$(CH$_2$)$_{15}$CH$_3$)$_2$ | Autorad. MT-wells (Ex. 8b) | + |

(c) Quantitation of virus binding by ELISA method

Microtiter plates type Cooks M29 were used throughout this investigation. Coating of the plates with natural glycolipids, synthetic glycolipids, and rabbit anti-Sendai virus-serum was performed in the following manner:

Natural globotetraosyl-$\beta$-ceramide and galactosyl-$\beta$-ceramide were dissolved in analtical grade methanol to the following concentrations: 20, 10, 5, 2.5, 1.5, 0.75, 0.375, 0.185, 0.092 and 0.046 $\mu$g/ml. Synthetic Gal$\beta$1→4Glc$\beta$O-CH$_2$CH(CH$_2$SO$_2$(CH$_2$)$_{15}$CH$_3$)$_2$, Glc$\beta$O-CH$_2$CH(CH$_2$SO$_2$(CH$_2$)$_{15}$CH$_3$)$_2$, Gal$\beta$1→4Glc$\beta$1→4Glc$\beta$O-CH$_2$CH(CH$_2$S-(CH$_2$)$_{15}$CH$_3$)$_2$, and Glc$\beta$O-CH$_2$CH(CH$_2$S(CH$_2$)$_{15}$CH$_3$)$_2$ were dissolved in analytical grade methanol to the following concentrations: 100, 50, 25, 6.25, and 1.56 $\mu$g/ml. Each of the above solutions (50 $\mu$l) were added to a microtiter well and the methanol was allowed to evaporate over night.

Rabbit anti-Sendai virus-serum was diluted to 50 $\mu$g of protein/ml in sodium carbonate/sodium hydrogen carbonate buffer to pH 9.6. The serum solution (100 $\mu$l) was added to a series of microtiter wells and incubated at room temperature over night and the buffer solution was removed. A solution of BSA (100 $\mu$l, 2%) in Tris-HCl (5 mM)-NaCl (0.15M) solution (pH 8.5) was added. The plates were incubated at 37° C. for 2 h and then washed twice with an excess of BSA-solution (1%) in Tris-HCl (50 mM)-NaCl (0.15M) having pH 8.5.

Sendai virus was diluted to a protein concentration of 15 $\mu$g/ml in a solution of BSA (1%) in Tris-HCl (50 mM)-NaCl (0.15M), pH 8.5. The virus solution (100 $\mu$l) was added to each coated well of the above mentioned microtiter plates. The plates were incubated at 37° C. for 2 h and then washed four times with an excess of BSA-solution (1%) in Tris-HCl-NaCl (concentration as above). Mouse monoclonal anti-Sendai virus antibody in BSA-solution (100 $\mu$l, 1% of BSA, Tris-HCl-NaCl as above), was added to each well. The plates were incubated at 37° C. for 90 min. and then washed four times with an excess of BSA-solution (1% of BSA in Tris-HCl-NaCl as above). Horseradish peroxidase-conjugated rabbit anti-mouse antibody (Dakopatts) was diluted to 20 μg/ml in BSA-solution (1% of BSA, Tris-HCl-NaCl as above). Aliquots (100 μl) were added to the microtiter wells above and the plates were incubated at 37° C. for 90 min. and then washed four times with an excess of BSA-solution (1% of BSA, Tris-HCl-NaCl as above). Orthophenylenediamine (OPD) solution (100 μl; 4 mg OPD and 4 μl 30 % $H_2O_2$ in 10 ml of 0.1M citrate phosphate buffer; pH 5.0) was added to each well and the plates were incubated at room temperature for 15 min. Sulfuric acid (50 μl, 0.5M) was added to each well and the absorption was measured at 492 nm (see FIG. 1).

(d) Inhibition of virus binding; ELISA method

This assay was performed as described above (c) with the following exceptions:

(1) Only one concentration (10 μg/ml) of globotetraosyl-β-ceramide and galactosyl-β-ceramide was used.

(2) Before addition of virus suspension to the microtiter wells, the virus was incubated with varying amounts of the neo-glycoprotein [Galβ1→4GlcβO-$CH_2CH(CH_2SO_2(CH_2)_7CH_3)CH_2SO_2(CH_2)_{10}COONH]_{\sim 20}$-BSA. The noe-glycoprotein was dissolve in Tris-HCl (50 mM)-NaCl (0.15M), pH 8.5 to the following concentrations: 4.4, 1.1, 0.275, 0.069, 0.017, 0.004, and 0.001 mg/ml. Sendai virus suspension (4 μl) was added to each of the neo-glycoprotein solutions (265 μl) so that the final virus concentration was 45 μg/ml. The mixture was incubated at 37° C. for 2 h and the resulting virusneoglycoprotein-suspension (50 μl) was used in the virus assay as described above (c). The results are shown in FIG. 2. Globotetraosyl-β-ceramide was used as a negative control since it has been shown earlier to lack binding capacity of Sendai virus.

(e) Inhibition of virus binding; thin-layer plate method

Sendai virus (60 μg) was incubated at room temperature for 1 h with Galβ1→4GlcβO-$CH_2CH(CH_2SO_2$-$(CH_2)_{10}COONa)_2$ (2 mg), Galβ1→4Glcβ-O-$CH_2CH(CH_2SO_2(CH_2)_7CH_3(CH_2SO_2(CH_2)_{h1-9}COONa$ (2 mg), and Galβ1→4GlcβO-$CH_2CH(CH_2SO_2(CH_2)_7CH_3)CH_2SO_2(CH_2)_{10}CONH$-BSA (1 mg), each dissolved in 2 ml of PBS. The mixtures were overalid on thin layer plates containing several natural glycolipids known as second step receptors for Sendai virus (see Karl-Anders Karlsson, Antiviral agents; Danish patent application No. 178/85 filed on the priority date of the present application). The plates were incubated and worked up as described above (Ex. 8a). A positive inhibition was registered as a significant weakening of the darkness of receptor spots on the autoradiogram. The results are shown in Table 7 below.

TABLE 7

Inhibition of Sendai virus binding to natural glycolipids by synthetic neo-glycoconjugates.

| Neo-glycoconjugate | Inhibition |
|---|---|
| Galβ1 → 4GlcβO—$CH_2CH(CH_2SO_2(CH_2)_{10}COONa)_2$ | − |
| Galβ1 → 4GlcβO—$CH_2CH(CH_2SO_2(CH_2)_7CH_3)CH_2SO_2(CH_2)_{10}COONa$ | − |
| Galβ1 → 4GlcβO—$CH_2CH(CH_2SO_2(CH_2)_7CH_3)CH_2SO_2(CH_2)_{10}CONHBSA$ | + |

EXAMPLE 9

Assay for bacterial binding specificity; thin layer plate method

The method has been described in detail (Hansson et al., Anal. Biochem. 146, 1985, pp. 158–163). Bacteria were externally radiolabelled using Iodogen and $Na^{125}I$ (Hansson et al. above). E. Coli was the strain characterized in detail elsewhere for Galα→Gal binding specificity (Bock et al. J. Biol. Chem. 260, 1985, pp 8545–8551). Propionibacterium freudenreichii has been reported earlier to bind lactosylceramid (Hansson et al., Glycoconjugates, M. A. Chester, D. Heinegård, A. Lundblad and S. Svensson, eds. 1983, pp 631–632, Rahms in Lund, Lund, Sweden). The radiolabelled bacteria were overlayed on plates that contained the neo-glycolipids shown in Table 8 below. Work-up and detection was performed as described in the references above (essentially as for virus binding as described in Example 8a). The results are shown in Table 8 below.

TABLE 8

Binding of bacteria to synthetic glycolipids

| Glycolipid | Bacterium | Binding |
|---|---|---|
| Galβ1 → 4GlcβO—$CH_2CH(CH_2$—S—$(CH_2)_{15}CH_2)_2$ | Propionibacterium freudenreichii | (+) |
| Galβ1 → 4GlcβO—$CH_2CH(CH$—S—$(CH_2)_{17}CH_3)_2$ | " | (+) |
| Galβ1 → 4GlcβO—$CH_2CH(CH_2$—$SO_2$—$(CH_2)_{15}CH_3)_2$ | " | + |
| Galα1 → 4GalβO—$CH_2CH(CH_2$—S—$(CH_2)_{15}CH_3)_2$ | E. coli | + |
| Galα1 → 4GalβO—$CH_2CH(CH_2$—$SO_2$—$(CH_2)_{15}CH_3)_2$ | " | + |

REFERENCES CITED

S. Hakomori, Ann. Rev. Biochem., 50, (1981), p 733.

N. Sharon and H. Lis, Chem. Eng. News, (Mar. 30, 1981), p 21.

R. U. Lemieux, Chem. Soc. Rev., (1978), p 423.

N. Sharon and H. Lis, Science, 177, (1972), p 949.

E. A. Kabat, Methods Enz., 70, (1972), p 3.

E. H. Beachey, J. Infect. Diseases, 143, (1981), p 325.

J. S. Slama and R. R. Rando, Biochemistry, 19, (1980), p 4595.

J. Dahmen, T. Frejd, G. Magnusson, G. Noori, and A. -S. Carlström, Carbohydr. Res., 127, (1984), p 27.

R. U. Lemieux, D. R. Bundle, and D. A. Baker, J. Am. Chem. Soc, 97, (1975), p 4076.

J. Dahmen, T. Frejd, G. Magnusson, G. Noori, and A. -S. Carlström, Carbohydr. Res., 129, (1984), p 63.

J. N. Israelachvili, S. Marcelja, and R. G. Horn, Quarterly Reviews of Biophysics, 13, (1980), p 121.

J. Dahmen, T. Frejd, G. Grönberg, T. Lave, G. Magnusson, G. Noori, Carbohydr. Res., 116, (1983), p 303.

M. A. Nashed and L. Anderson, J. Am. Chem. Soc., 104, (1982), p 7282.

We claim:

1. An O-glycosidic compound of the formula (sugar)$_n$-1-O-CH$_2$-A where A is

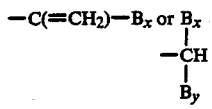

B$_x$ and B$_y$, which may be the same or different, are groups of the formula II,

n is an integer from 1 to 10, inclusive, and sugar is selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galactose, D-glucuronic acid, D-galacturonic acid, D-mannuronic acid, 2-deoxy-2-phthalimido-D-glucose, 2-deoxy-2-phthalimido-D-galactose and sialic acid, and derivatives thereof, where, when n>1, the sugar units may be the same or different, where m and p independently are 0 or 1 and m+p is 0, 1, or 2, R$_4$ is a saturated or unsaturated, branched or unbranched chain of 1-25 carbon atoms, aryl or a steroid group, R$_5$ is H, CHO, NO$_2$, NH$_2$, OH, SH, COOH, COOR$_{10}$, CONHNH$_2$, CON$_3$, CH(OR$_{10}$)$_2$, or a carrier, and R$_{10}$ is C$_{1-4}$ alkyl or a carrier.

2. The compound of claim 1 where A is —C(=CH$_2$)-B$_x$.

3. The compound of claim 2 wherein m=0 and p=0.

4. The compound of claim 1 where A is:

$$-\underset{\underset{B_y}{|}}{\overset{\overset{B_x}{|}}{CH}}$$

5. The compound of claim 4 wherein m=0 and p=0.
6. The compound of claim 4 wherein m=1 and p=0.
7. The compound of claim 4 wherein m=1 and p=1.
8. The compound of claim 1 wherein the compound binds preferentially to a virus.
9. The compound of claim 8 wherein the compounds binds to Sendai virus.
10. The compound of claim 1 wherein the compound competitively inhibits the binding of a virus to a natural glycolipid membrane receptor.
11. The compound of claim 1 wherein the compound binds preferentially to a bacterium.
12. The compound of claim 1 wherein the compound binds to *Proprionibacterium freudenreichii* or *Esherichia coli*.
13. The compound of claim 1 in which R$_4$ is an unbranched alkyl chain of 2-17 carbon atoms and R$_5$ is H, COOR$_{10}$ wherein R$_{10}$ is CH$_3$ or a carrier.
14. The compound of claim 1 in which m=0 and p=0.
15. The compound of claim 1 in which m=1 and p=0.

16. The compound of claim 1 in which m=1 and p=1.
17. The compound of claim 5 wherein the compound is selected from the group consisting of RSC16-1, RSC16-2, RSC16-3, RSC16-4, RSC16-5, RSC16-6, RSC16-7, RSC16-8, RSC16-9, RSC16-10, RSC16-11, RSC16-12, RSC16-13, RSC16-14, RSC18-1, RSC8-1, RSC8-2, RSC10E-1, RSC10E-2, and RSC10EC8 as defined in Table 2.
18. The compound of claim 6 wherein the compound is selected from the group consisting of RSOC16-1, RSOC16-2, RSOC16-3, RSOC16-4, RSOC16-5, RSOC16-6, RSOC16-7, RSOC16-8, RSOC16-9, RSOC16-10, RSOC16-11, RSOC16-12, RSOC16-13, RSOC16-14, ROSC18-1, RSOC18-2, RSOC8-1, ROSC8-2, RSOC10E-1, and RSOC10E-2 as defined in Table 3.
19. The compound of claim 7 wherein the compound is selected from the group consisting of RSO$_2$C16-1, RSO$_2$C16-2, RSO$_2$C16-3, RSO$_2$C16-4, RSO$_2$C16-5, RSO$_2$C16-6, RSO$_2$C16-7, RSO$_2$C16-8, RSO$_2$C16-9, RSO$_2$C16-10, RSO$_2$C16-11, RSO$_2$C16-12, RSO$_2$C16-13, RSO$_2$C16-14, RSO$_2$C18-1, RSO$_2$C18-2, RSO$_2$C8-1, ROS$_2$C8-2, RSO$_2$C10E-1, RSO$_2$C10E-2, RSO$_2$C10A, RSO$_2$C10EC8-1, RSO$_2$C10EC8-2 and RSO$_2$C10AC8 as defined in Table 4.
20. The compound of claim 3 wherein the compound is selected from the group consisting of ARSC16-1, ARSC16-2, .
21. A polymeric compound having the formula XX $$\left[ \begin{array}{c} \phantom{CH_2}\text{CH}_2-\text{S}-\text{R}_4-\text{S} \\ | \\ (\text{sugar})_n\text{-1-O}-\text{CH} \\ | \\ \phantom{(sugar)_n\text{-1-O}-}\text{CH}_2 \end{array} \right]_k$$

where k is an integer from 2-1000, n is 1-10, and sugar is selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galactose, D-glucuronic acid, D-galacturonic acid, D-mannuronic acid, 2-deoxy-2-phthalimido-D-glucose, 2-deoxy-2-phthalimido-D-galactose and sialic acid, and derivatives thereof, where, when n>1, the sugar units may be the same or different, and R$_4$ is a saturated or unsaturated, branched or unbranched chain of 1-25 carbon atoms, aryl or a steroid group.

22. A polymeric compound comprising a three-dimensional network of 2-1000 units of the formula XXIa $$\begin{array}{c} \text{CH}_2- \\ | \\ (\text{sugar})_n\text{-1-O}-\text{CH}_2-\text{CH} \\ | \\ \text{CH}_2- \end{array}$$

and 2-1000 units of the formula XXIb, $$\begin{array}{c} \text{S}- \\ | \\ -\text{S}-\text{R}_4-\text{S}- \end{array}$$

wherein a unit of Formula XXIa is never bonded directly to another unit of Formula XXIa and a unit of Formula XXIb is never bonded directly to another unit of Formula XXIb, $R_4$ is a saturated or unsaturated, branched or unbranched chain of 1–25 carbon atoms, aryl or a steroid group, n=1 to 10, and sugar is selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galatose, D-glucuronic acid, D-galacturonic acid, D-mannuronic acid, 2-deoxy-2-phthalimido-D-glucose, 2-deoxy-2-phthalimido-D-galactose and sialic acid, and derivatives thereof, where, when n>1, the sugar units may be the same or different.

23. The compound of claim 1 wherein the steroid is cholesterol or lanosterol.

24. The compound of claim 1 wherein n>1.

25. The compound of claim 1 in which (a) $R_5$ is a carrier, or (b) $R_5$ is —COOR$_{10}$ or —CH(OR$_{10}$)$_2$, and $R_{10}$ is a carrier.

26. An O-glycosidic compound of the formula (sugar)$_n$-1-O-CH$_2$-A, where A is

and $R_1$ is a group of the Formula II,

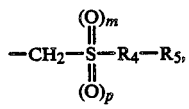  (II)

and $R_2$ is a group of formula II, a group -CH$_2$X wherein X is a leaving group, a group -CH$_2$OR$_6$ (wherein $R_6$ is -H or -R$_4$-R$_5$), or a group

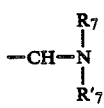

wherein $R_7$ and $R'_7$ which may be same or different, are the same as $R_6$ defined above, n is an integer from 1 to 10, inclusive, and sugar is selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galactose, D-glucuronic acid, D-galacturonic acid, D-mannuronic acid, 2-deoxy-2-phthalimido-D-glucose, 2-deoxy-2-phthalimido-D-galactose and sialic acid, and derivatives thereof, where, when n>1, the sugar units may be the same or different, where m and p independently are 0 or 1 and m+p is 0, 1, or 2, $R_4$ is saturated or unsaturated, branched or unbranched chain of 1–25 carbon atoms, aryl or a steroid group, $R_5$ is H, CHO, NO$_2$, NH$_2$, OH, SH, COOH, COO$_{R10}$, CONHNH$_2$, CON$_3$, CH(OR$_{10}$)$_2$, or a carrier, and $R_{10}$ is $C_{1-4}$ alkyl or a carrier.

27. An O-glycosidic compounds of the formula I(b), (sugar)$_n$-1-O-C(=CH$_2$)-CH$_2$X, where X is a halogen, n=1 to 10 inclusive, and sugar is selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galactose, D-glucuronic acid, D-galacturonic acid, D-mannuronic acid, 2-deoxy-2-phthalimido-D-glucose, 2-deoxy-2-phthalimido-D-galactose and sialic acid, and derivatives thereof, where, when n>1, the sugar units may be the same or different.

* * * * *

UNITED STATES PATENT AND TRADEMARK OFFICE
CERTIFICATE OF CORRECTION

PATENT NO. : 4,868,289

DATED : September 19, 1989

INVENTOR(S) : Magnusson et al.

It is certified that error appears in the above-identified patent and that said Letters Patent is hereby corrected as shown below:

In column 24, line 36, "$R_7$" should read --$R'_7$--.

In column 39, line 33, "$^{13}C$-NMR" should read --'H-NMR--.

In column 48, line 33-34, the following should be deleted "and with chloroform/methanol/2.5 M ammonia for non-acid glycolipids".

In column 50, line 38, "Glcβ1" should be deleted.

UNITED STATES PATENT AND TRADEMARK OFFICE
CERTIFICATE OF CORRECTION

PATENT NO. :   4,868,289

DATED      :   September 19, 1989

INVENTOR(S):   Magnusson et al.

It is certified that error appears in the above-identified patent and that said Letters Patent is hereby corrected as shown below:

The lower line in the figures of Table 1, column 34 has not been drawn. Please delete the following:

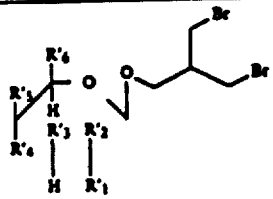

and substitute therefor the following:

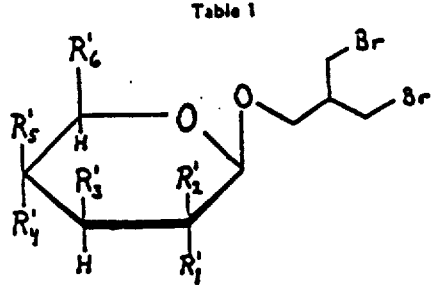

UNITED STATES PATENT AND TRADEMARK OFFICE
CERTIFICATE OF CORRECTION

PATENT NO. : 4,868,289

DATED : September 19, 1989

INVENTOR(S) : Magnusson et al.

It is certified that error appears in the above-identified patent and that said Letters Patent is hereby corrected as shown below:

In Table 1, column 34, line 38, second word, "DAc$^a$" should read --OAc$^a$--.

The lower line in the figures of Table 2, columns 37 and 38 has not been drawn. Please delete the following:

TABLE 2

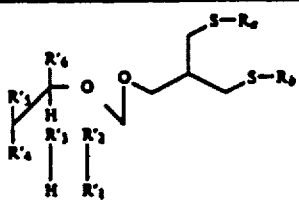

and substitute therefor the following:

Table 2

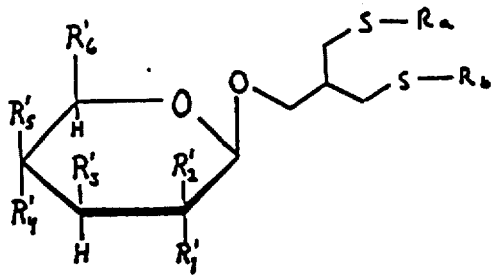

UNITED STATES PATENT AND TRADEMARK OFFICE
CERTIFICATE OF CORRECTION

PATENT NO. : 4,868,289

DATED : September 19, 1989

INVENTOR(S) : Magnusson et al.

It is certified that error appears in the above-identified patent and that said Letters Patent is hereby corrected as shown below:

In Table 2, column 38, line 18, last word "α-galactopyranosyl" should read --α-D-galactopyranosyl--.

The lower line in the figures of Table 3, column 42 has not been drawn. Please delete the following:

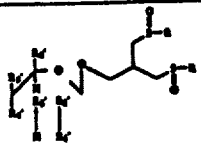

and substitute therefor the following:

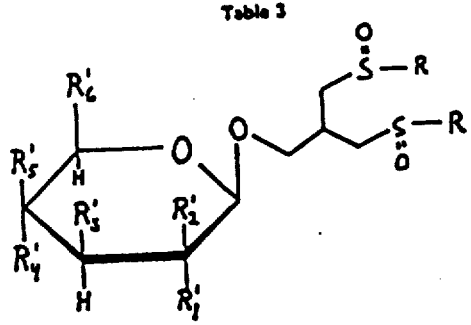

UNITED STATES PATENT AND TRADEMARK OFFICE
CERTIFICATE OF CORRECTION

PATENT NO. : 4,868,289

DATED : September 19, 1989

INVENTOR(S) : Magnusson et al.

It is certified that error appears in the above-identified patent and that said Letters Patent is hereby corrected as shown below:

In Table 3, column 42, "R = $(CH_2)_{15}CHS$" should read --R = $(CH_2)_{15}CH_3$--.

The lower line in the figures of Table 4, columns 42 and 43 has not been drawn. Please delete the following:

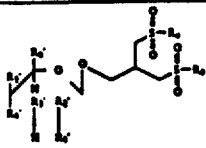

and substitute therefor the following:

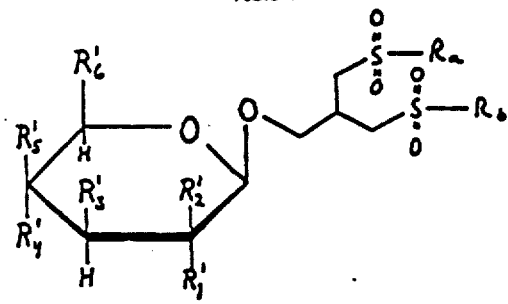

UNITED STATES PATENT AND TRADEMARK OFFICE
CERTIFICATE OF CORRECTION

PATENT NO.    : 4,868,289

DATED         : September 19, 1989

INVENTOR(S)   : Magnusson et al.

It is certified that error appears in the above-identified patent and that said Letters Patent is hereby corrected as shown below:

In Table 4, column 43, third line from the bottom, "RSO$_2$-C10EC8-1" should read --RSO$_2$C10EC8-1--.

The lower line in the figures of Table 5, column 47 has not been drawn. Please delete the following:

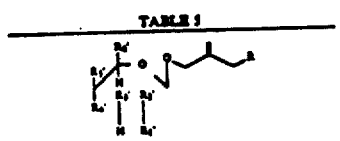

and substitute therefor the following:

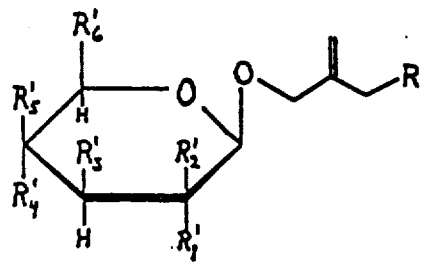

UNITED STATES PATENT AND TRADEMARK OFFICE
CERTIFICATE OF CORRECTION

PATENT NO. : 4,868,289

DATED : September 19, 1989

INVENTOR(S) : Magnusson et al.

It is certified that error appears in the above-identified patent and that said Letters Patent is hereby corrected as shown below:

In Table 6, column 50, third line "$SO_2$" should be deleted as it is mentioned twice.

In Table 8, column 52, first line, last word "$(CH_2)_{15}CH_2)_2$" should read --$(CH_2)_{15}CH_3)_2$--.

Signed and Sealed this

Twenty-fifth Day of June, 1991

Attest:

HARRY F. MANBECK, JR.

Attesting Officer

Commissioner of Patents and Trademarks